US008105347B2

(12) United States Patent
Schraga

(10) Patent No.: US 8,105,347 B2
(45) Date of Patent: Jan. 31, 2012

(54) ADJUSTABLE DISPOSABLE/SINGLE-USE BLADE LANCET DEVICE AND METHOD

(75) Inventor: Steven Schraga, Surfside, FL (US)

(73) Assignee: Stat Medical Devices, Inc., Miami, FL (US)

( * ) Notice: Subject to any disclaimer, the term of this patent is extended or adjusted under 35 U.S.C. 154(b) by 1965 days.

(21) Appl. No.: 10/988,636

(22) Filed: Nov. 16, 2004

(65) Prior Publication Data

US 2006/0106411 A1 May 18, 2006

(51) Int. Cl.
A61B 17/14 (2006.01)

(52) U.S. Cl. ........................................ 606/181; 600/583

(58) Field of Classification Search .................. 606/181, 606/182, 184, 185; 600/573, 583
See application file for complete search history.

(56) References Cited

U.S. PATENT DOCUMENTS

| 676,678 | A | 6/1901 | Ellifrits |
| 1,135,465 | A | 4/1915 | Pollock |
| 2,848,809 | A | 2/1956 | Crowder |
| 2,823,677 | A | 2/1958 | Hein, Jr. |
| 3,589,213 | A | 6/1971 | Gourley |
| 3,760,809 | A | 9/1973 | Campbell, Jr. |
| 4,064,871 | A | 12/1977 | Reno |
| 4,139,011 | A | 2/1979 | Benoit et al. |
| 4,157,086 | A | 6/1979 | Maiorano et al. |
| 4,203,446 | A | 5/1980 | Höfert et al. |
| 4,257,561 | A | 3/1981 | McKinney |
| 4,388,925 | A | 6/1983 | Burns |
| 4,426,105 | A | 1/1984 | Plaquin et al. |
| 4,438,770 | A | 3/1984 | Unger et al. |
| 4,449,529 | A | 5/1984 | Burns et al. |
| 4,469,110 | A | 9/1984 | Slama |
| 4,517,978 | A | 5/1985 | Levin et al. |
| 4,527,561 | A | 7/1985 | Burns |
| 4,539,988 | A | 9/1985 | Shirley et al. |
| 4,553,541 | A | 11/1985 | Burns |

(Continued)

FOREIGN PATENT DOCUMENTS

CA 523078 3/1956

(Continued)

OTHER PUBLICATIONS

U.S. Appl. No. 11/052,738 in the name of Schraga entitled "A Single Use Lancet Device", filed on Feb. 7, 2005.

(Continued)

Primary Examiner — Victor Nguyen
(74) Attorney, Agent, or Firm — Greenblum & Bernstein, P.L.C.

(57) ABSTRACT

Single-use blade lancet device includes a body having a rear end and a front end that includes a blade tip opening. A trigger is mounted to the body. A blade member is movably mounted within the body and includes a front end and a rear end. The blade member is movable between a first retracted position, an extended position, and a second retracted position. A biasing arrangement biases the blade member from the first retracted position towards the extended position and then towards the second retracted position. A guiding arrangement guides the blade member while the blade member moves from the first retracted position towards the extended position and then towards the second retracted position. During movement of the blade member, the guiding arrangement ensures that blade member maintains substantially the same orientation with respect to the body. This Abstract is not intended to define the invention disclosed in the specification, nor intended to limit the scope of the invention in any way.

51 Claims, 44 Drawing Sheets

U.S. PATENT DOCUMENTS

| | | | |
|---|---|---|---|
| 4,628,929 A | 12/1986 | Intengan et al. | |
| 4,643,189 A | 2/1987 | Mintz | |
| 4,688,570 A * | 8/1987 | Kramer et al. | 606/166 |
| 4,785,858 A | 11/1988 | Valentini et al. | |
| RE32,922 E | 5/1989 | Levin et al. | |
| 4,834,667 A | 5/1989 | Fowler et al. | |
| 4,858,607 A | 8/1989 | Jordan et al. | |
| 4,869,249 A | 9/1989 | Crossman et al. | |
| 4,895,147 A | 1/1990 | Bodicky et al. | |
| 4,924,879 A | 5/1990 | O'Brien | |
| 4,976,724 A | 12/1990 | Nieto et al. | |
| 4,990,154 A | 2/1991 | Brown et al. | |
| 5,074,872 A | 12/1991 | Brown et al. | |
| 5,133,730 A | 7/1992 | Biro et al. | |
| 5,147,375 A | 9/1992 | Sullivan et al. | |
| 5,212,879 A | 5/1993 | Biro et al. | |
| 5,269,799 A | 12/1993 | Daniel | |
| 5,282,822 A | 2/1994 | Macors et al. | |
| 5,304,193 A | 4/1994 | Zhadanov | |
| 5,314,441 A | 5/1994 | Cusack et al. | |
| 5,318,584 A | 6/1994 | Lange et al. | |
| 5,324,303 A | 6/1994 | Strong et al. | |
| 5,350,392 A | 9/1994 | Purcell et al. | |
| 5,356,420 A | 10/1994 | Czernecki et al. | |
| 5,366,470 A | 11/1994 | Ramel | |
| 5,395,388 A | 3/1995 | Schraga | |
| 5,423,847 A | 6/1995 | Strong et al. | |
| 5,439,473 A | 8/1995 | Jorgensen | |
| 5,454,828 A | 10/1995 | Schraga | |
| 5,464,418 A | 11/1995 | Schraga | |
| 5,476,101 A | 12/1995 | Schramm et al. | |
| 5,509,345 A | 4/1996 | Cyktich | |
| 5,518,004 A | 5/1996 | Schraga | |
| 5,527,333 A | 6/1996 | Nikkels et al. | |
| 5,527,334 A | 6/1996 | Kanner et al. | |
| 5,529,581 A | 6/1996 | Cusack | |
| 5,545,174 A | 8/1996 | Schenk et al. | |
| 5,554,166 A | 9/1996 | Lange et al. | |
| 5,569,286 A | 10/1996 | Peckham et al. | |
| 5,569,287 A | 10/1996 | Tezuka et al. | |
| 5,571,132 A | 11/1996 | Mawhirt et al. | |
| D376,203 S | 12/1996 | Schraga | |
| 5,613,978 A | 3/1997 | Harding | |
| 5,628,764 A | 5/1997 | Schraga | |
| 5,628,765 A | 5/1997 | Morita | |
| 5,643,306 A | 7/1997 | Schraga | |
| 5,662,672 A | 9/1997 | Pambianchi et al. | |
| 5,730,753 A | 3/1998 | Morita | |
| 5,733,300 A | 3/1998 | Pambianchi et al. | |
| 5,741,288 A * | 4/1998 | Rife | 606/181 |
| RE35,803 E | 5/1998 | Lange et al. | |
| 5,772,677 A | 6/1998 | Mawhirt et al. | |
| 5,782,852 A * | 7/1998 | Foggia et al. | 606/182 |
| 5,797,940 A | 8/1998 | Mawhirt et al. | |
| 5,797,942 A | 8/1998 | Schraga | |
| 5,873,887 A | 2/1999 | King et al. | |
| 5,879,367 A | 3/1999 | Latterell et al. | |
| 5,908,434 A | 6/1999 | Schraga | |
| 5,916,230 A | 6/1999 | Brenneman et al. | |
| 5,984,940 A | 11/1999 | Davis et al. | |
| 6,010,519 A | 1/2000 | Mawhirt et al. | |
| 6,022,366 A | 2/2000 | Schraga | |
| 6,042,595 A | 3/2000 | Morita | |
| 6,045,567 A | 4/2000 | Taylor et al. | |
| 6,056,765 A | 5/2000 | Bajaj et al. | |
| 6,071,294 A | 6/2000 | Simons et al. | |
| D428,150 S | 7/2000 | Ruf et al. | |
| 6,136,013 A | 10/2000 | Marshall et al. | |
| 6,152,942 A | 11/2000 | Brenneman et al. | |
| 6,156,050 A | 12/2000 | Davis et al. | |
| 6,156,051 A | 12/2000 | Schraga | |
| 6,168,606 B1 | 1/2001 | Levin et al. | |
| 6,183,489 B1 | 2/2001 | Douglas et al. | |
| 6,190,398 B1 | 2/2001 | Schraga | |
| 6,192,891 B1 | 2/2001 | Gravel et al. | |
| 6,197,040 B1 | 3/2001 | Le Vaughn et al. | |
| 6,210,420 B1 | 4/2001 | Mauze et al. | |
| 6,221,089 B1 | 4/2001 | Mawhirt | |
| 6,228,100 B1 | 5/2001 | Schraga | |
| 6,258,112 B1 | 7/2001 | Schraga | |
| 6,283,982 B1 | 9/2001 | Levaughn et al. | |
| 6,306,152 B1 | 10/2001 | Verdonk et al. | |
| 6,322,574 B1 | 11/2001 | Lloyd et al. | |
| 6,322,575 B1 | 11/2001 | Schraga | |
| 6,332,871 B1 | 12/2001 | Douglas et al. | |
| 6,346,114 B1 | 2/2002 | Schraga | |
| 6,358,265 B1 | 3/2002 | Thorne, Jr. et al. | |
| 6,364,889 B1 | 4/2002 | Kheiri et al. | |
| 6,379,317 B1 | 4/2002 | Kintzig et al. | |
| 6,395,495 B1 | 5/2002 | Montagnier et al. | |
| 6,409,740 B1 | 6/2002 | Kuhr et al. | |
| 6,419,661 B1 | 7/2002 | Kuhr et al. | |
| 6,451,040 B1 | 9/2002 | Purcell | |
| 6,464,649 B1 | 10/2002 | Duchon et al. | |
| 6,506,168 B1 | 1/2003 | Fathallah et al. | |
| 6,514,270 B1 * | 2/2003 | Schraga | 606/182 |
| 6,540,762 B1 | 4/2003 | Bertling | |
| 6,558,402 B1 * | 5/2003 | Chelak et al. | 606/182 |

FOREIGN PATENT DOCUMENTS

| | | |
|---|---|---|
| EP | 0061102 | 9/1982 |
| EP | 0137975 | 4/1985 |
| EP | 0189117 | 7/1986 |
| EP | 0885590 | 12/1998 |
| EP | 0904731 | 3/1999 |
| EP | 1074219 | 2/2001 |
| FR | 1126718 | 11/1956 |

OTHER PUBLICATIONS

U.S. Appl. No. 10/998,636 in the name of Schraga entitled "Disposable or Single-Use Lancet Device and Method", filed Nov. 30, 2004.

Sutor et al., "Bleeding from Standardized Skin Punctures: Automated Technic for Recording Time, Intensity, and Pattern of Bleeding", *A.J.C.P.*, vol. 55, pp. 541-549 (May 1971).

\* cited by examiner

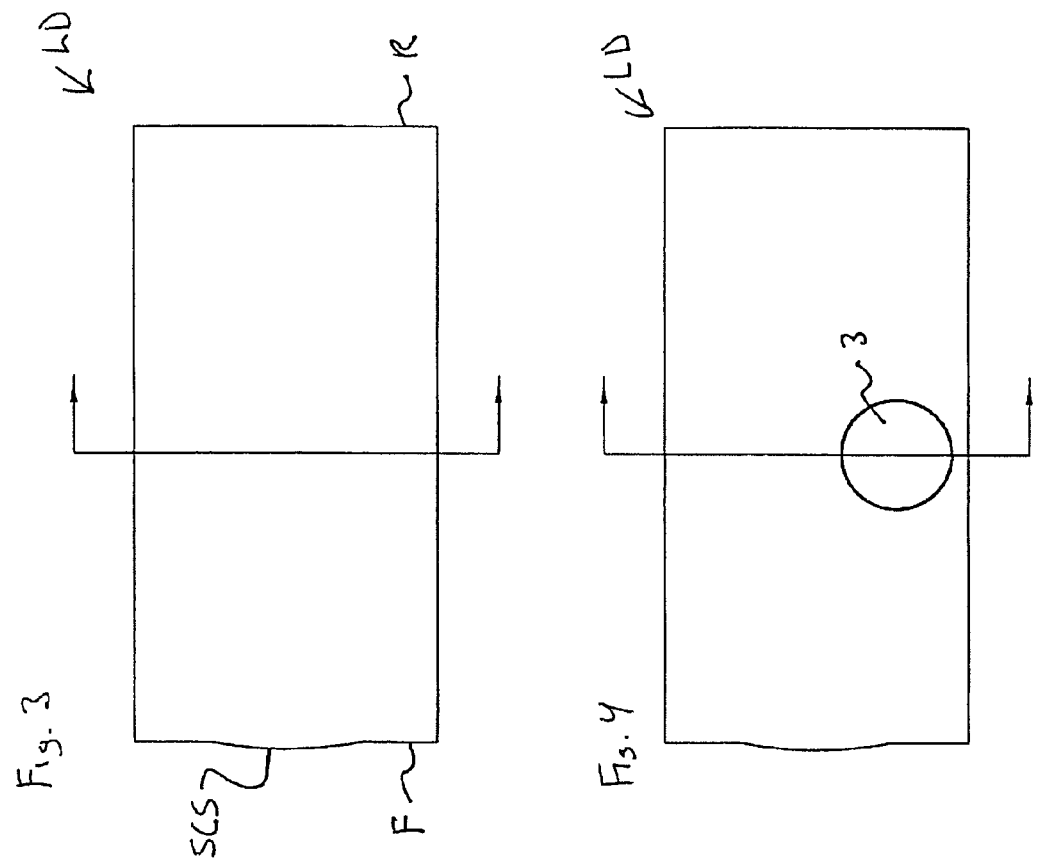

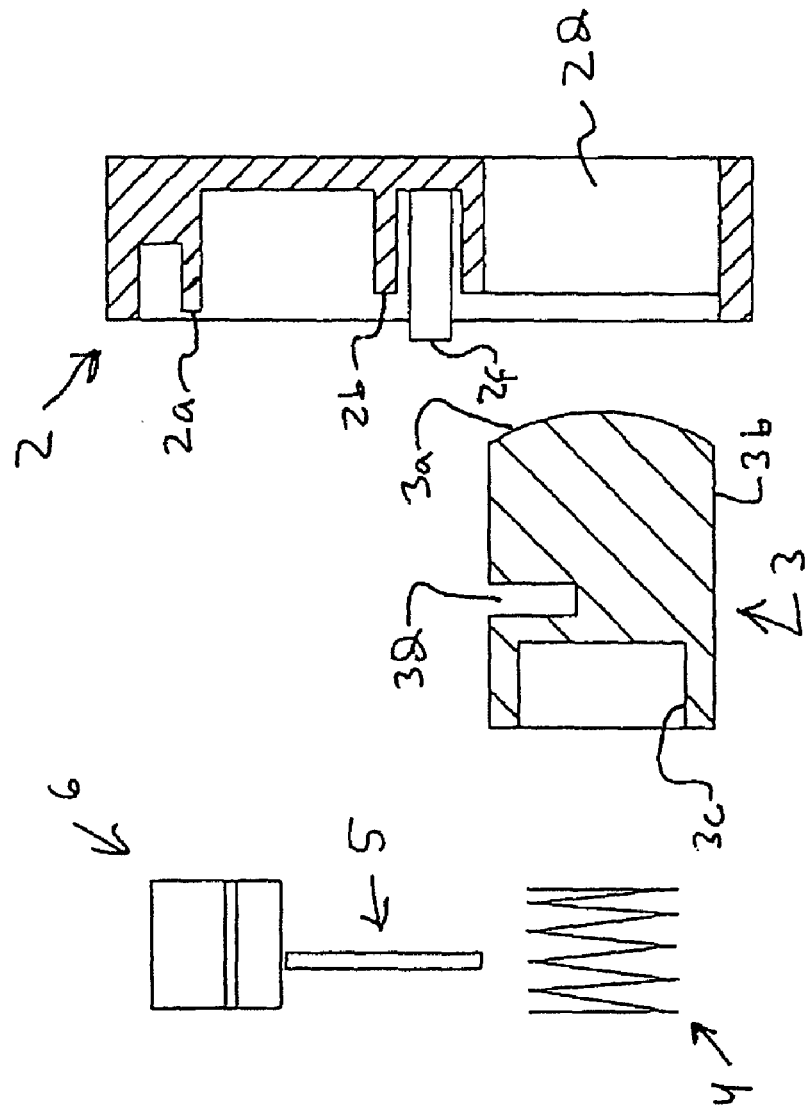
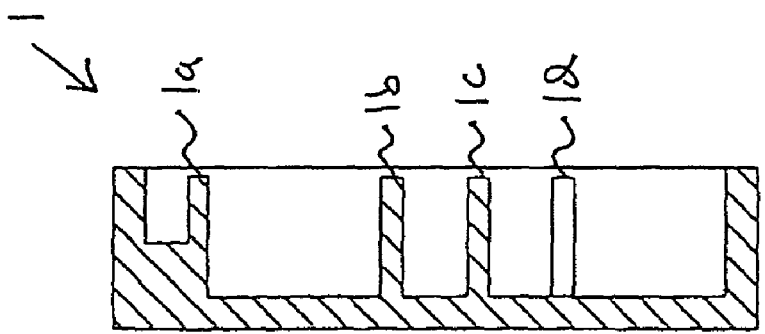
Fig. 7

← LD

← LD

← LD

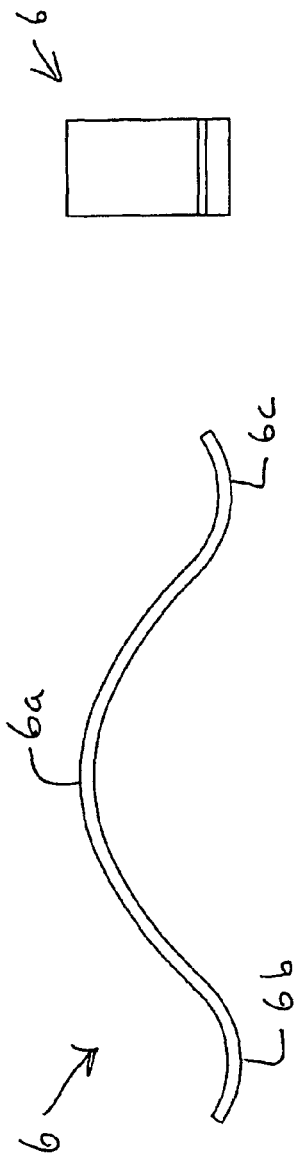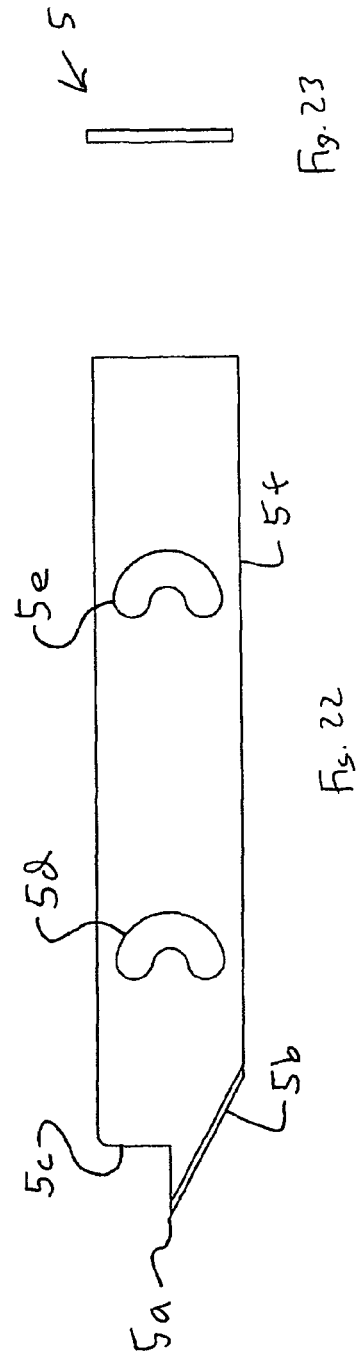

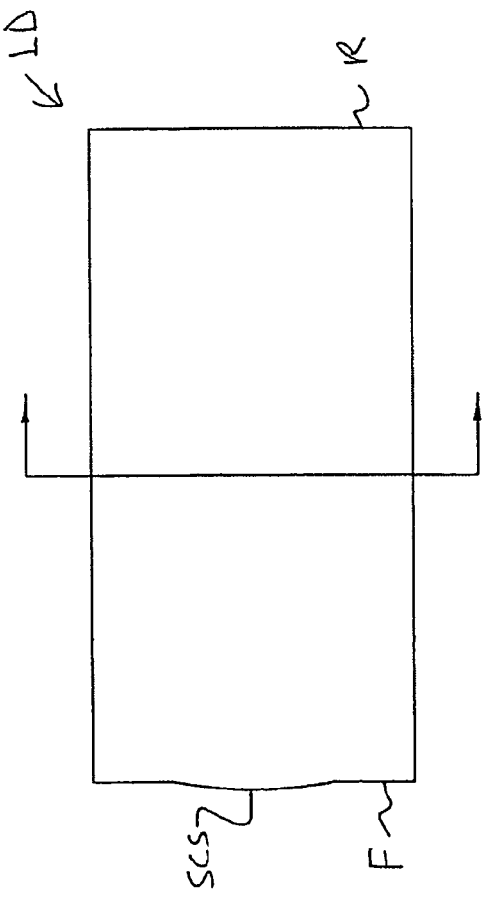
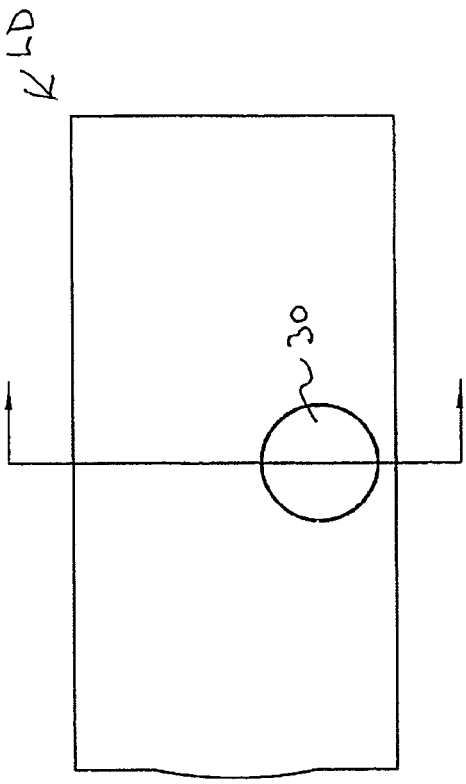
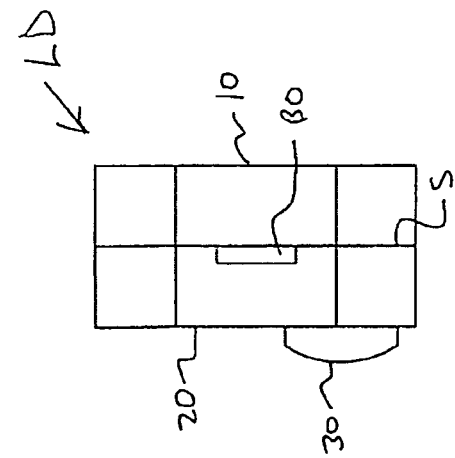
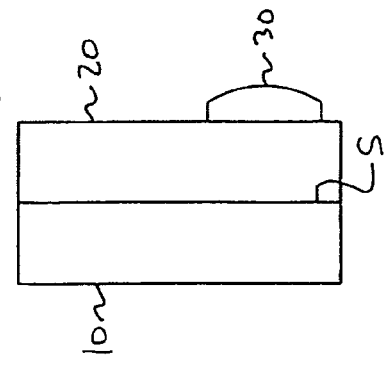

← LD

← LD

← LD

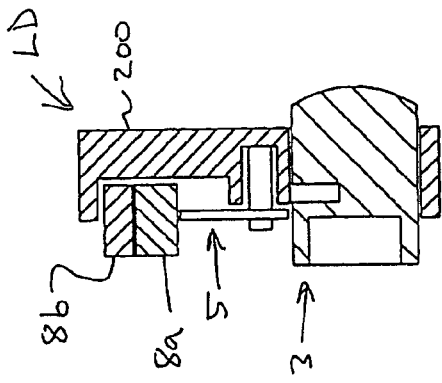
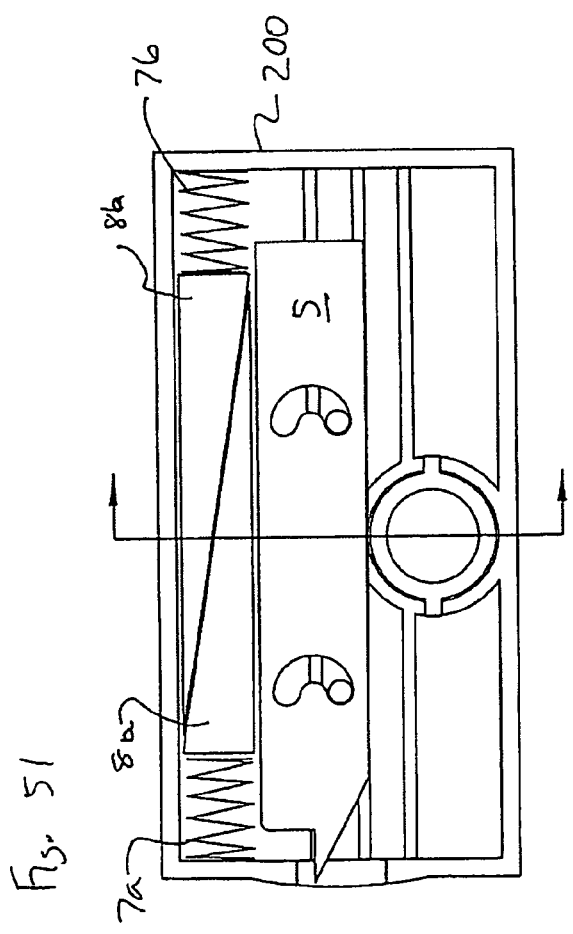
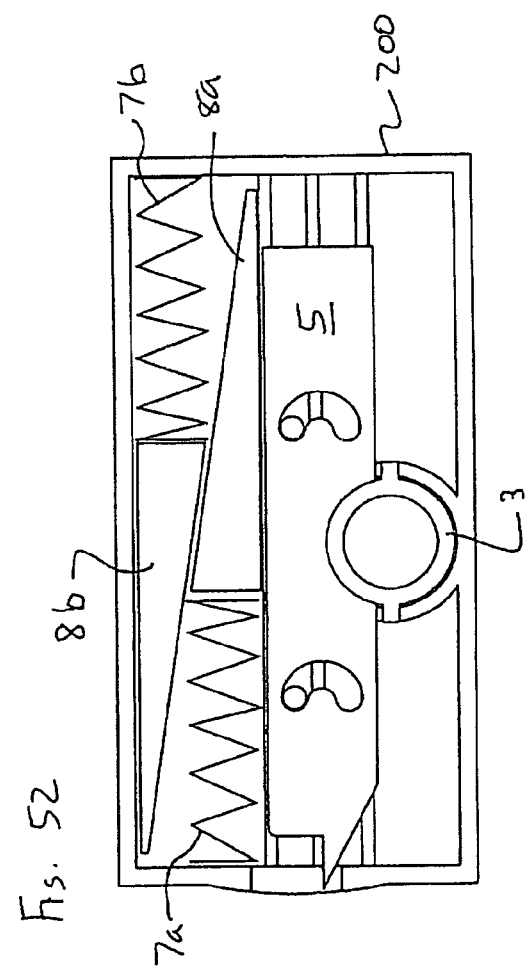

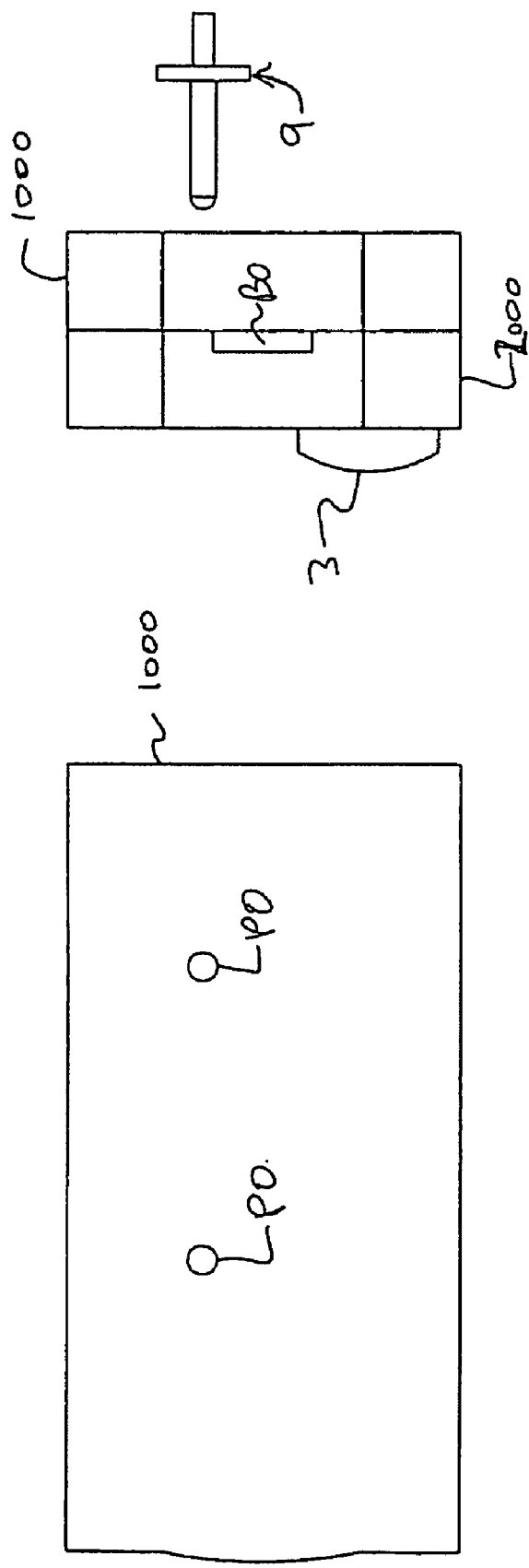

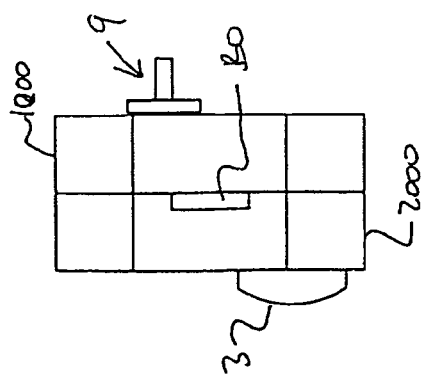
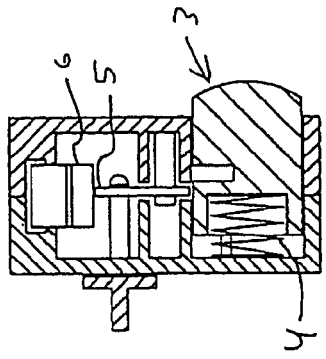
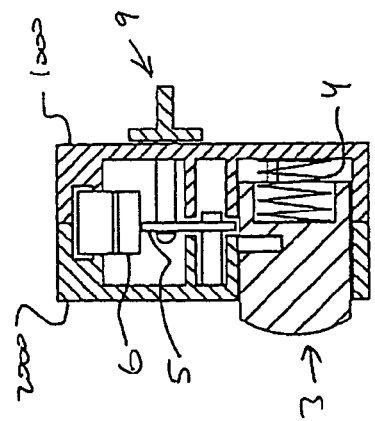
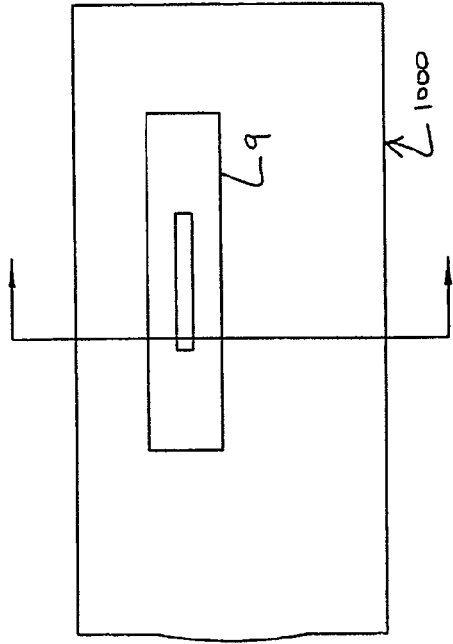
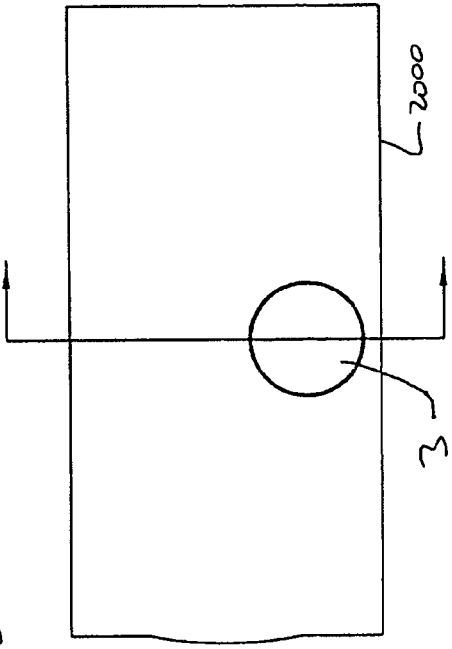

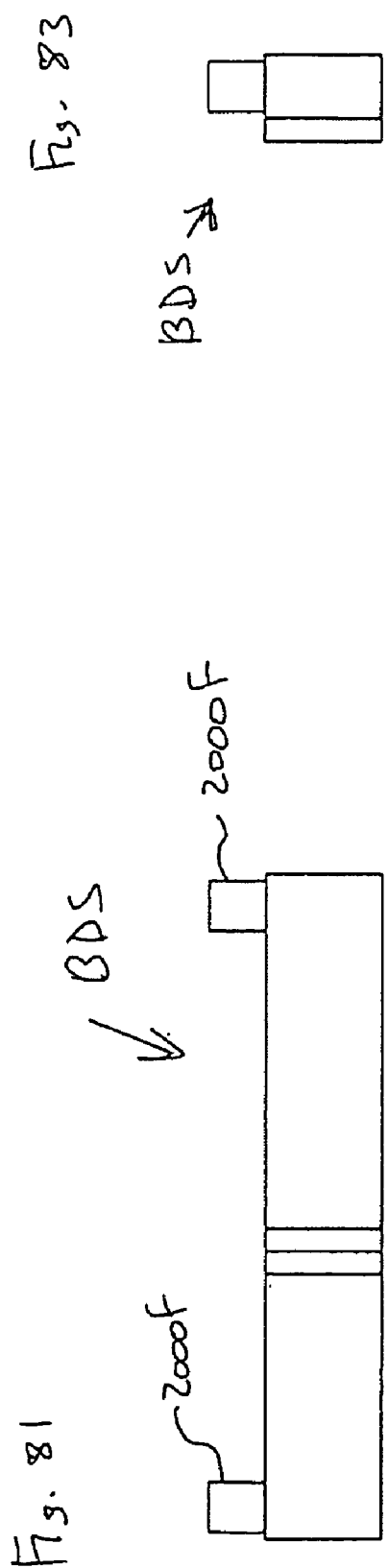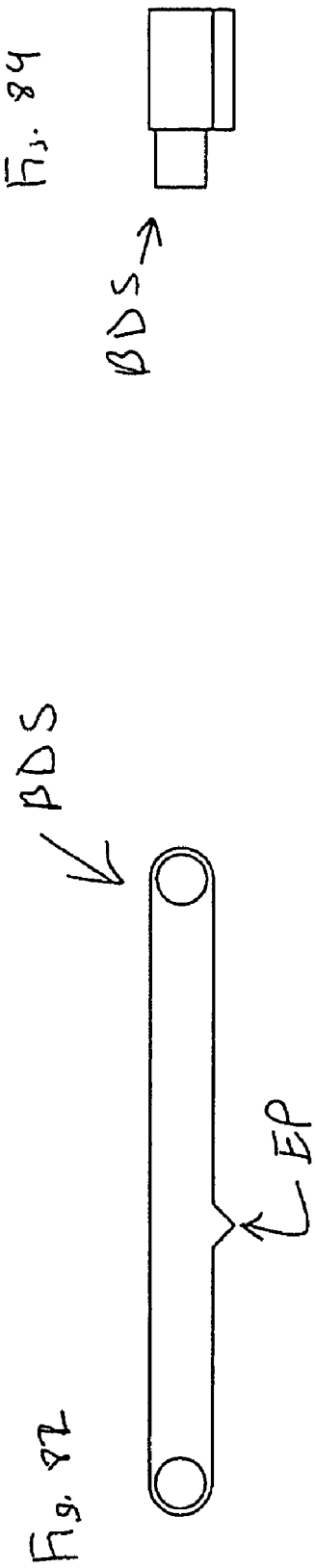

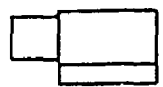
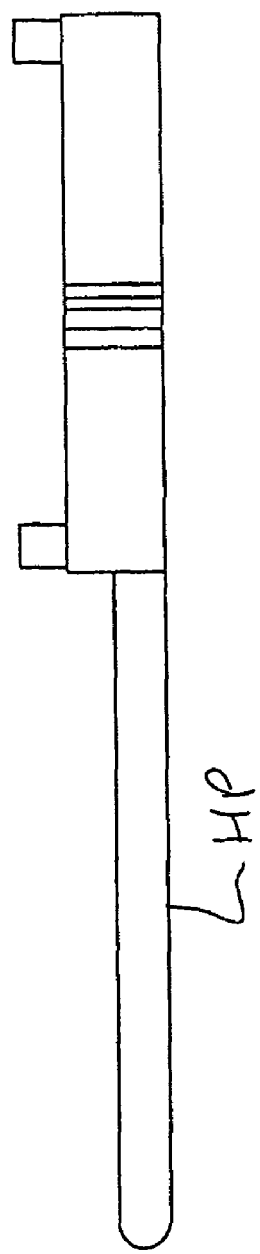
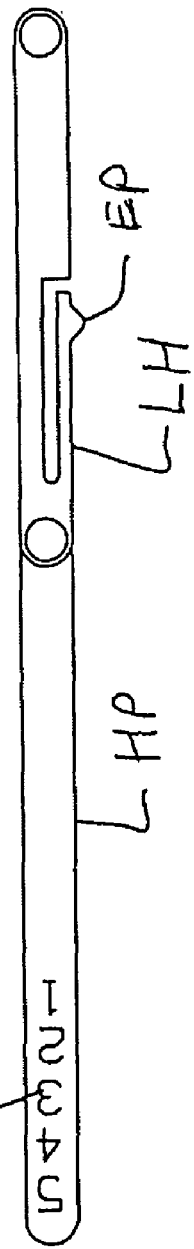

ADJUSTABLE DISPOSABLE/SINGLE-USE BLADE LANCET DEVICE AND METHOD

BACKGROUND OF THE INVENTION

1. Field of the Invention

The invention relates to a disposable and/or single-use blade lancet device having an adjusting capability, and to a method of using a disposable and/or single-use blade lancet device. In particular, the invention relates to a blade lancet device which may be both disposable and/or made for single use, i.e., can be used once and discarded. The invention also relates to such a blade lancet device which utilizes an adjustable depth of penetration. The blade lancet device has particular application in a medical service environment (e.g., doctor's office, nurse's station, or hospital) in taking a blood sample from an infant by, e.g., pricking the infant's heel, in order to diagnose and/or check for, e.g., bilirubin.

2. Discussion of Background Information

Lancet needle devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Incision devices are used to create a small incision in the skin of a user for various purposes such as for determining a bleeding time and for taking a blood sample. However, such devices typically utilize a plunging blade movement which can be painful. Other devices utilize a slicing movement which can also be painful. Still other devices provide for a controlled blade path such that the blade depth increases and decreases between a point of maximum depth. However, such devices are complex and utilize may parts. Such known devices typically do not utilize cutting-depth adjustment.

An improved device would allow the user to easily, safely, smoothly, and in a less painful manner, form a small incision in the skin. Such a device would also be disposable and inexpensive to use. Finally, such a device would allow a user to adjust the depth of penetration of a single-use blade lancet and would overcome some of the disadvantages described above.

Thus, while advances have been made, there is a continuing need for a blade lancet device which provides for convenient, reliable and easy use and/or which allows for adjustment of penetration depth. The device should also be inexpensively made (i.e., by utilizing fewer parts or components) so that it can be economically used a single time and thereafter disposed of.

SUMMARY OF THE INVENTION

According to one aspect of the invention there is provided a disposable and/or single-use blade lancet device that includes a body. A trigger is preferably mounted to the body. A front end of the body includes a skin engaging end that includes a blade tip opening through which a lancet blade extends and/or moves. A blade member is movably mounted within the body and comprises a front end and a rear end. The blade member is movable between a first retracted position, an extended position, and a second retracted position. A biasing arrangement biases the blade member from the first retracted position towards the extended position and then towards the second retracted position. A guiding arrangement guides the blade member while the blade member moves from the first retracted position towards the extended position and then towards the second retracted position. During movement of the blade member, the guiding arrangement ensures that blade member maintains an orientation which is substantially parallel to an axis extending from the blade tip opening to the rear end of the body.

According to one aspect of the invention, the biasing arrangement preferably comprises a spring.

According to one aspect of the invention, the biasing arrangement preferably comprises at least one compression spring.

According to one aspect of the invention, the biasing arrangement preferably comprises a leaf spring.

According to one aspect of the invention, the biasing member preferably comprises two spaced apart compression springs.

According to one aspect of the invention, the trigger is preferably movably mounted to the body.

According to one aspect of the invention, the body preferably comprises a first housing part connected to a second housing part.

According to one aspect of the invention, the blade member preferably comprises a body portion made of one material and a blade tip portion made of a different material.

According to one aspect of the invention, the guiding arrangement preferably comprises two projections coupled to the blade member and two generally C-shaped cam recesses arranged within the body.

According to one aspect of the invention, the guiding arrangement preferably comprises two projections coupled to the body and two generally C-shaped cam recesses arranged on the blade member.

According to one aspect of the invention, the guiding arrangement preferably comprises two projections and two generally C-shaped cam recesses formed in the blade member.

According to one aspect of the invention, the guiding arrangement preferably comprises a plurality of projections extending from one side of the blade member and a plurality of generally C-shaped cam recesses.

According to one aspect of the invention, the guiding arrangement preferably comprises a plurality of non-movable projections and a corresponding plurality of generally C-shaped cam recesses, each generally C-shaped cam recess receiving therein one of the non-movable projections.

According to one aspect of the invention, the device preferably further comprises a trigger spring biasing the trigger towards an extended position.

According to one aspect of the invention, the trigger preferably comprises a slot which receives therein a portion of the blade member when the blade member is in the second retracted position.

According to one aspect of the invention, the trigger preferably comprises a slot which receives therein a portion of the blade member when the trigger moves from an extended position to a triggered position.

According to one aspect of the invention, the trigger preferably comprises a cam surface which engages with the blade member when the blade member is in the first retracted position.

According to one aspect of the invention, the device further preferably comprises an adjusting system that adjusts a depth of penetration.

According to one aspect of the invention, the adjusting system preferably comprises an engaging projection and a plurality of engaging recesses which are each configured to receive the engaging projection.

According to one aspect of the invention, the device further preferably comprises a removable safety device configured to prevent movement of the blade member.

According to one aspect of the invention, the body preferably comprises a generally rectangular shape.

According to one aspect of the invention, the blade member preferably comprises generally rectangular-shaped metal plate with a pointed blade tip defined by a tapered sharpened edge and a straight blunt edge.

According to one aspect of the invention, the guiding arrangement preferably guides a blade tip of the blade member along a curved path.

According to one aspect of the invention, the guiding arrangement preferably guides a blade tip of the blade member along a partially circular path.

According to one aspect of the invention, the body preferably comprises oppositely arranged projecting ribs which movably guide the blade member.

According to one aspect of the invention, the blade member preferably comprises at least one straight edge which remains substantially parallel to the axis throughout movement of the blade member.

According to one aspect of the invention, the blade member preferably comprises a width, a thickness and a length, wherein the width is less than the length, and wherein the width is greater than the thickness by a factor of at least five.

According to one aspect of the invention, the blade member preferably comprises a width, a thickness and a length, wherein the width is less than the length, and wherein the width is greater than the thickness by a factor of at least ten.

According to one aspect of the invention, the guiding arrangement preferably comprises two spaced apart circular projections extending from an inner surface of the body and two spaced apart C-shaped cam recesses formed in or on the blade member.

According to one aspect of the invention, the body preferably comprises at least one side opening through which a portion of the trigger protrudes.

According to one aspect of the invention, the body preferably comprises an ergonomic shape to facilitate gripping.

According to one aspect of the invention, the front end of the body preferably comprises an outwardly curved skin engaging surface.

According to one aspect of the invention, the body preferably comprises a two-piece plastic body.

According to one aspect of the invention, the body preferably comprises internal projecting fins which guide the movement of the blade member within the body.

According to one aspect of the invention, the blade tip opening preferably is a rectangular-shaped opening.

According to one aspect of the invention, the blade tip opening preferably is a rectangular-shaped slot.

The invention also provides for a method of puncturing a surface of skin using any of the devices described above, wherein the method comprises disposing the front end of the device against a user's skin, triggering the trigger to cause a blade tip of the blade member to penetrate the user's skin, and preventing the user from moving the blade member to the extended position and to the first retracted position.

The invention also provides for a method of puncturing a surface of skin using any of the devices described above, wherein the method comprises adjusting a set depth of penetration, disposing the front end of the device against a user's skin, triggering the trigger to cause a blade tip of the blade member to penetrate the user's skin, and preventing the user from moving the blade member to the extended position and to the first retracted position.

The invention also provides for a method of puncturing a surface of skin using any of the devices described above, wherein the method comprises adjusting a set depth of penetration, disposing the front end of the device against a user's skin, triggering the trigger to cause a blade tip of the blade member to penetrate the user's skin, and ensuring that the trigger remains in a triggered position.

The invention also provides for a method of puncturing a surface of skin using any of the devices described above, wherein the method comprises disposing the front end of the device against a user's skin, triggering the trigger to cause a blade tip of the blade member to penetrate the user's skin, and preventing the user from moving the trigger to an original armed or extended position.

The invention also provides for a method of puncturing a surface of skin using any of the devices described above, wherein the method comprises removing a removable safety device from the body, disposing the front end of the device against a user's skin, and triggering the trigger to cause movement of the blade member.

The invention also provides for a method of puncturing a surface of skin using any of the devices described above, wherein the method comprises moving an adjusting mechanism to a desired set position, removing a removable safety device from the body, disposing the front end of the device against a user's skin, and triggering the trigger to cause movement of the blade member.

The invention also provides for a method of puncturing a surface of skin using any of the devices described above, wherein the method comprises removing a removable safety device from engagement with the blade member, disposing the front end of the device against a user's skin, and triggering the trigger to cause movement of the blade member.

The invention also provides for a method of puncturing a surface of skin using any of the devices described above, wherein the method comprises moving an adjusting mechanism to a desired set position, removing a removable safety device from engagement with the blade member, disposing the front end of the device against a user's skin, and triggering the trigger to cause movement of the blade member.

The invention also provides for a single-use blade lancet device, wherein the device comprises a body comprising a rear end and a front end that includes a blade tip opening. A trigger is mounted to the body. A blade member is movably mounted within the body and comprises a front end and a rear end. The blade member is movable between a first retracted position, an extended position, and a second retracted position. A biasing arrangement biases the blade member from the first retracted position towards the extended position and then towards the second retracted position. A guiding arrangement comprises at least two projections which movably engage with at least two cam recesses. The guiding arrangement guides the blade member while the blade member moves from the first retracted position towards the extended position and then towards the second retracted position.

According to one aspect of the invention, each of the at least two cam recesses are preferably C-shaped.

According to one aspect of the invention, each of the at least two cam recesses are preferably at least partially circular.

According to one aspect of the invention, the guiding arrangement preferably guides the blade member along a curved path while the blade member moves from the first retracted position towards the extended position and then towards the second retracted position.

According to one aspect of the invention, the at least two projections are preferably connected to the body and the at least two cam recesses are arranged on the blade member.

According to one aspect of the invention, the at least two projections are preferably connected to the blade member and the at least two cam recesses are connected to the body.

The invention also provides for a single-use blade lancet device, wherein the device comprises a body comprising a rear end and a front end that includes a blade tip opening. A trigger is mounted to the body. A blade member is movably mounted within the body and comprising a front end and a rear end. The blade member is movable between a first retracted position, an extended position, and a second retracted position. A biasing arrangement biases the blade member from the first retracted position towards the extended position and then towards the second retracted position. A guiding arrangement guides the blade member while the blade member moves from the first retracted position towards the extended position and then towards the second retracted position. During movement of the blade member, the guiding arrangement ensures that blade member maintains substantially the same orientation with respect to the body.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 1 shows a front view of one embodiment of the single-use blade lancet device;

FIG. 2 shows a rear view of the embodiment of FIG. 1;

FIG. 3 shows a side view of the embodiment shown in FIG. 1;

FIG. 4 shows an opposite side view of the embodiment shown in FIG. 1 with the trigger button being visible;

FIG. 7 shows a cross-section view through the arrows in FIG. 4 in a dis-assembled arrangement;

FIG. 20 shows a side view of the spring member used in the embodiment of FIG. 1;

FIG. 21 shows an end view of the spring member of FIG. 20;

FIG. 22 shows a side view of the blade member used in the embodiment of FIG. 1;

FIG. 23 shows a rear end view of the blade member of FIG. 22;

FIG. 24 shows a front view of another embodiment of the single-use blade lancet device;

FIG. 25 shows a side view of the embodiment shown in FIG. 24;

FIG. 26 shows a rear view of the embodiment of FIG. 24;

FIG. 27 shows an opposite side view of the embodiment shown in FIG. 24 with the trigger button being visible;

Figure 34:
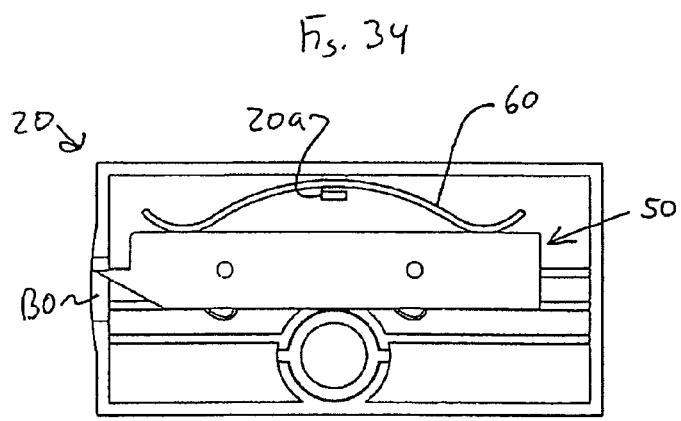
FIG. 34 shows the lancet device of FIG. 24 with the rear cover portion removed. The figure thus shows an inside view of the front cover portion of the embodiment shown in FIG.
Figure 35:
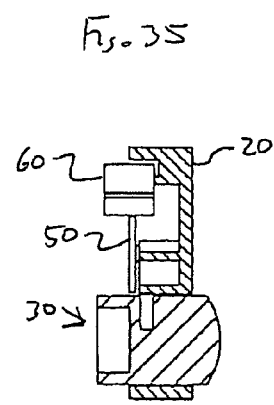
Figure 36:
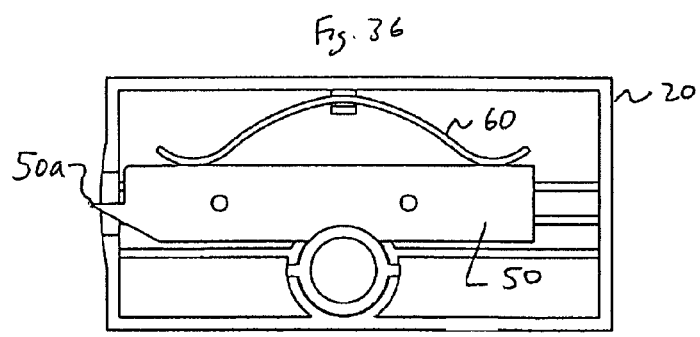
Figure 37:
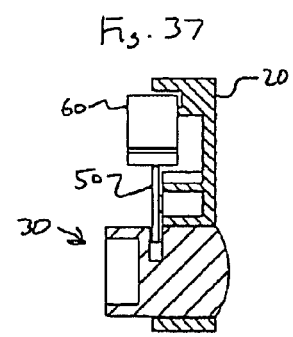
Figure 38:
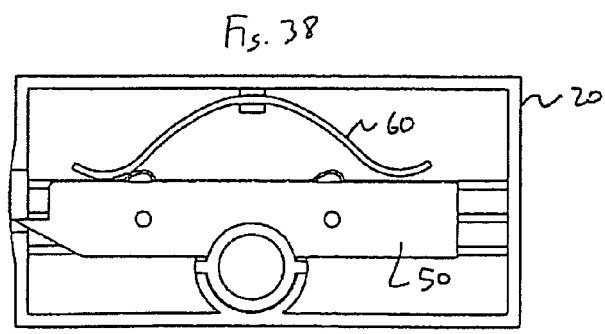
Figure 39:
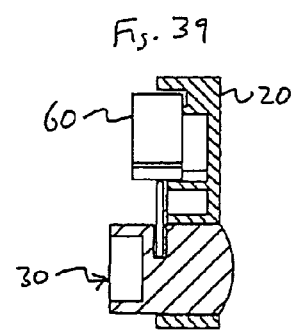
Figure 40:
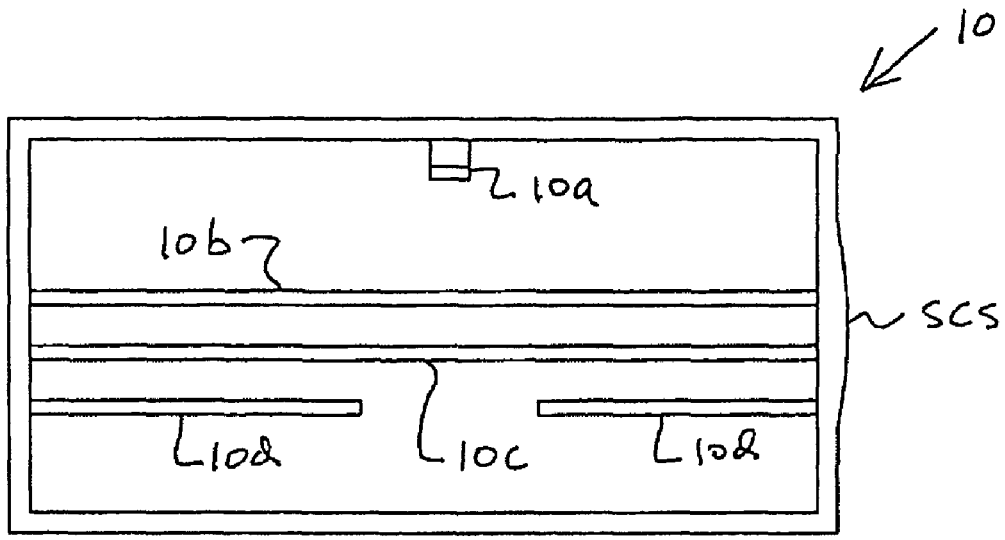
Figure 41:
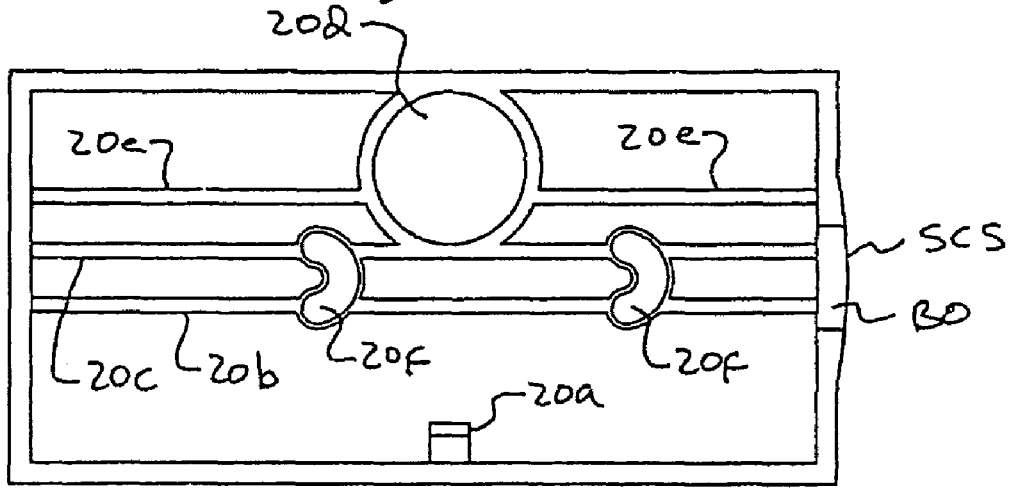
Figure 43:
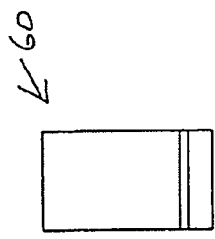
Figure 42:
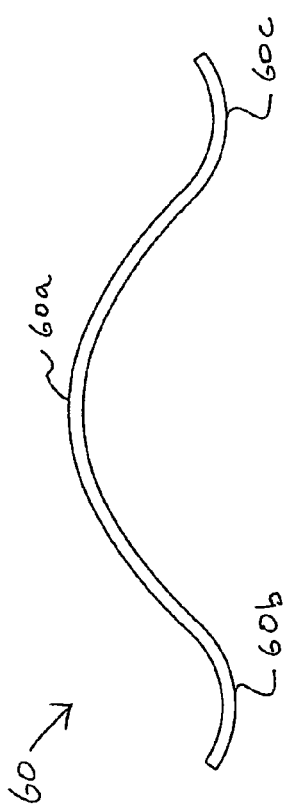
Figure 45:
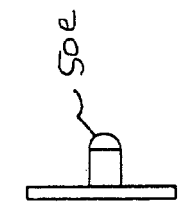
Figure 44:
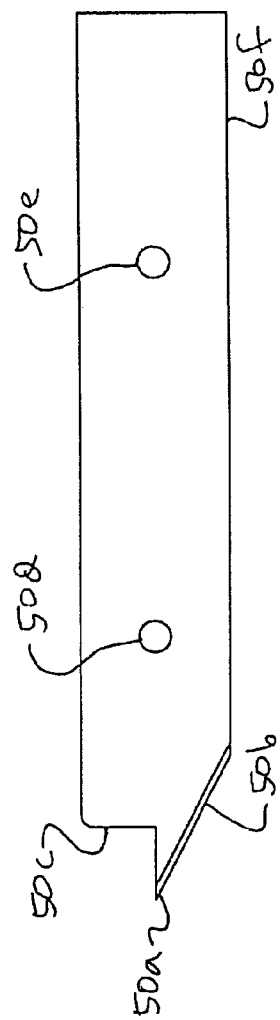
Figure 47:
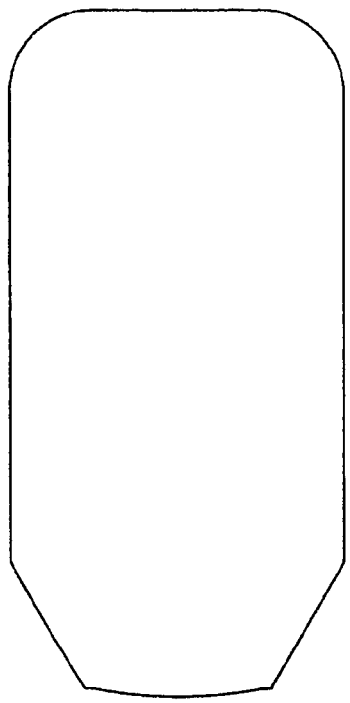
Figure 48:
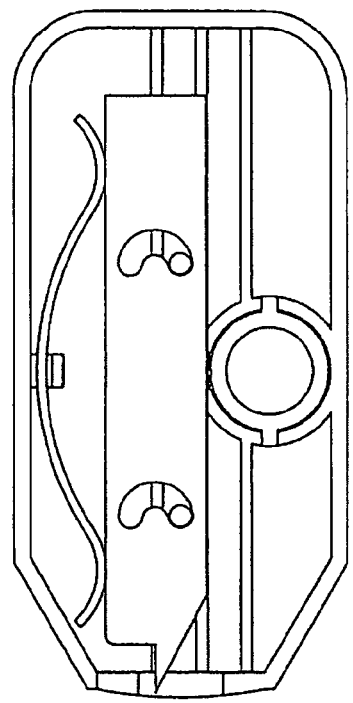
Figure 46:
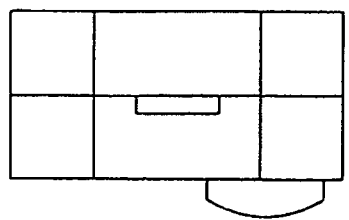
Figure 49:
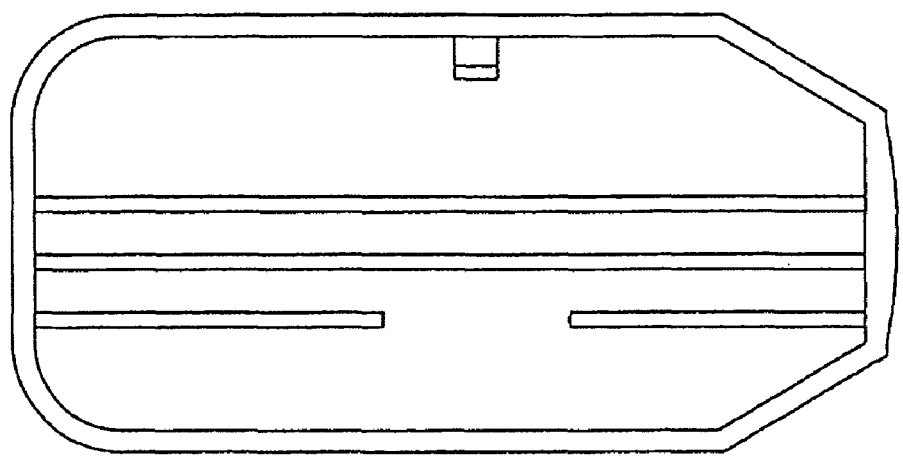
Figure 50:
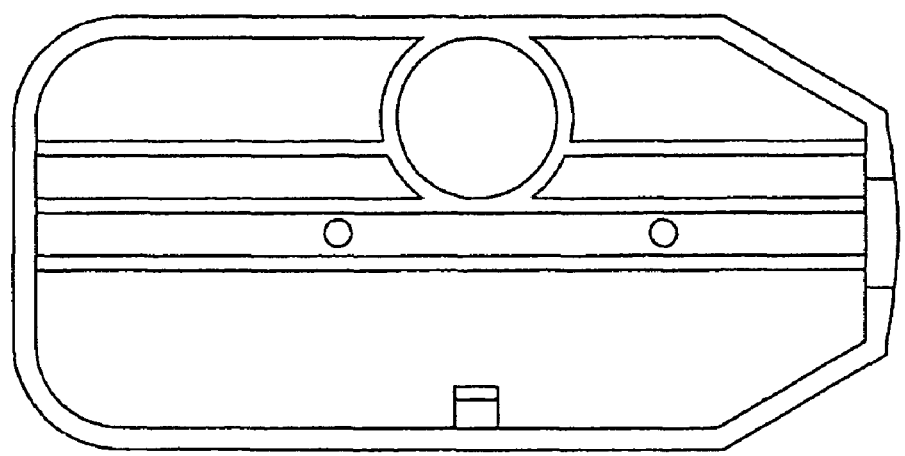
Figure 54:
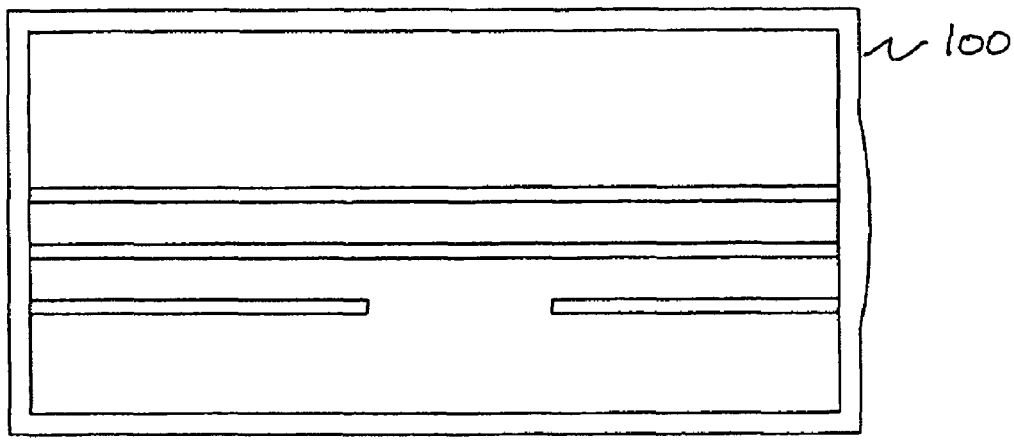
Figure 55:
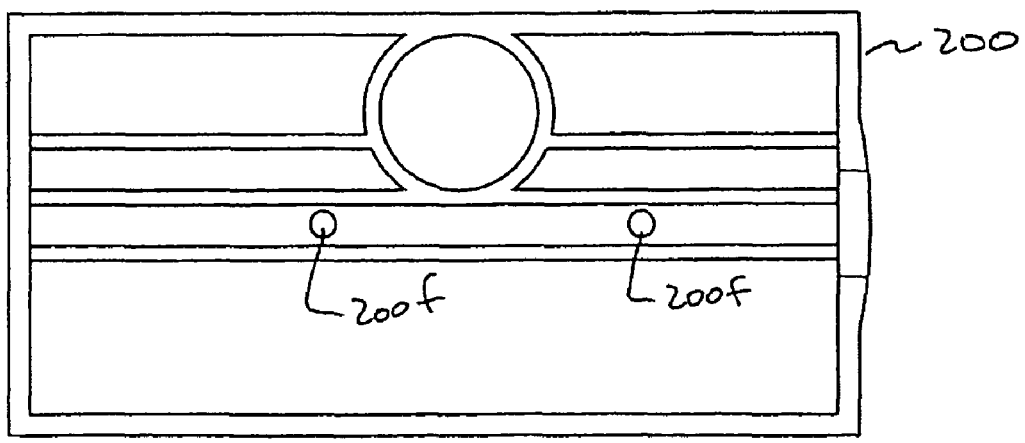
Figure 55:
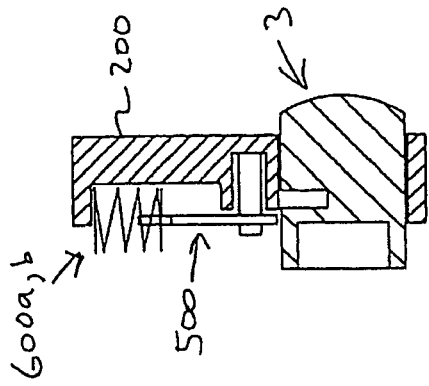
Figure 56:
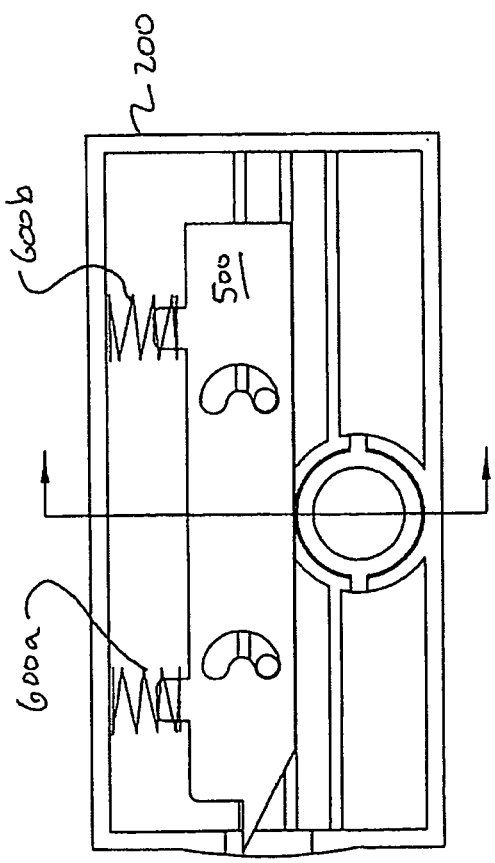
Figure 57:
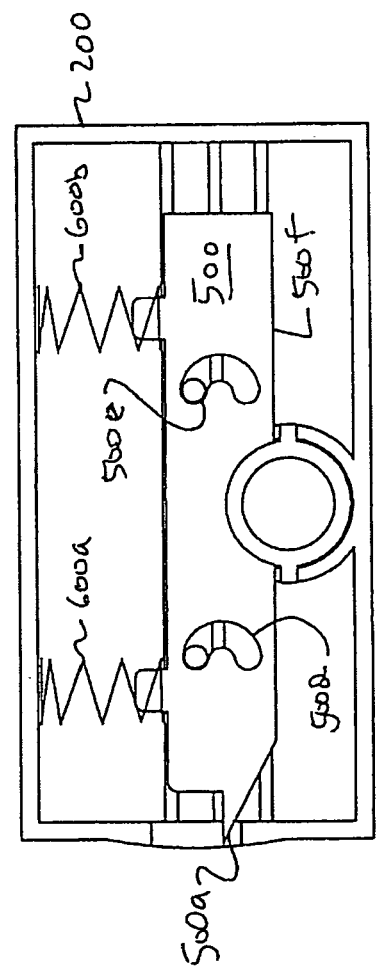
Figure 59:
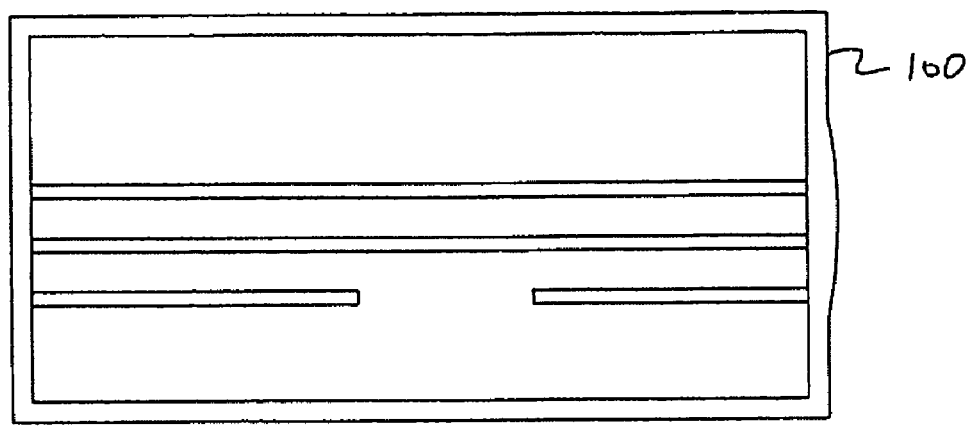
Figure 60:
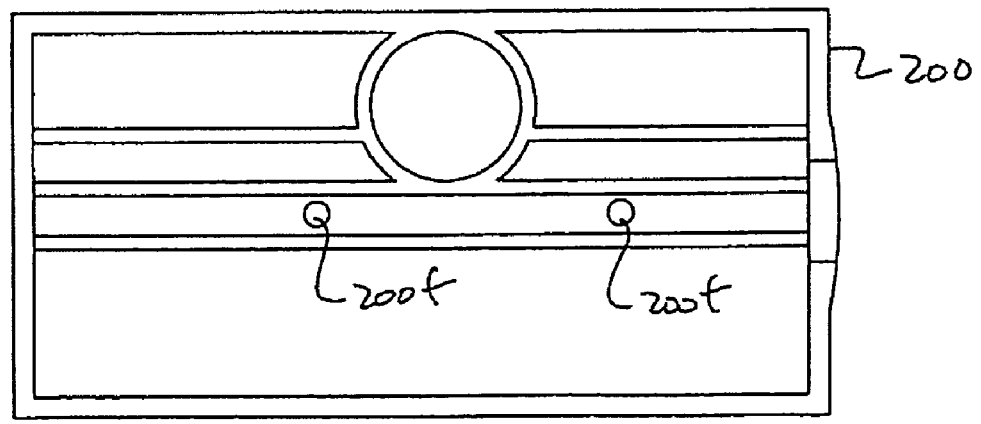
Figure 69:
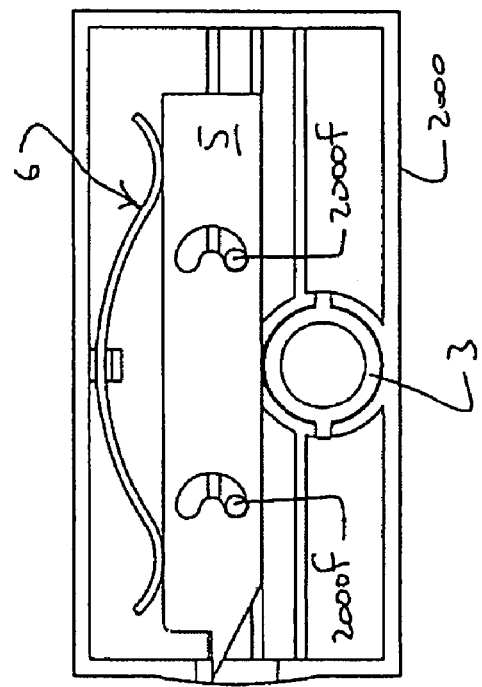
Figure 68:
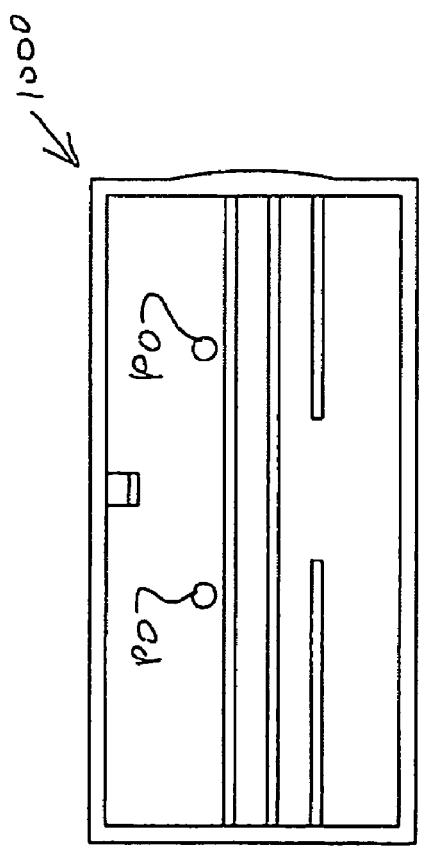
Figure 73:
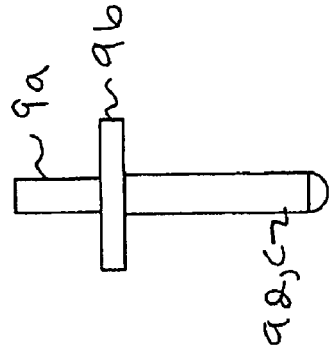
Figure 70:
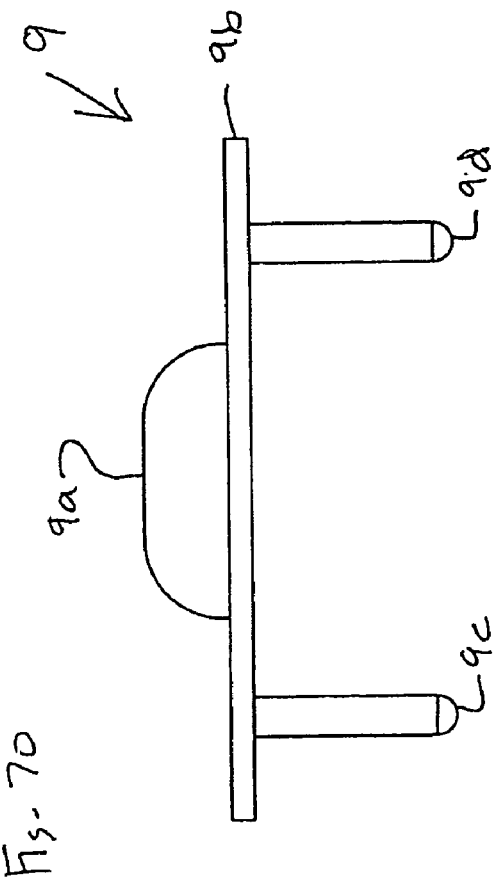
Figure 71:
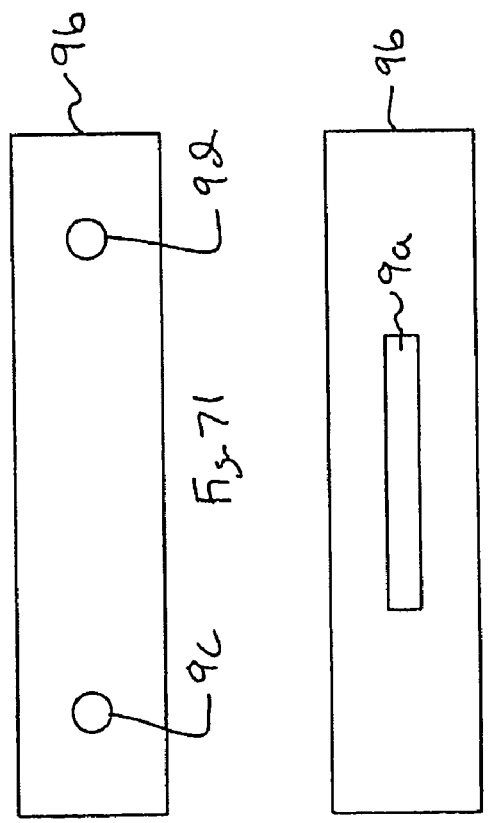
Figure 72:
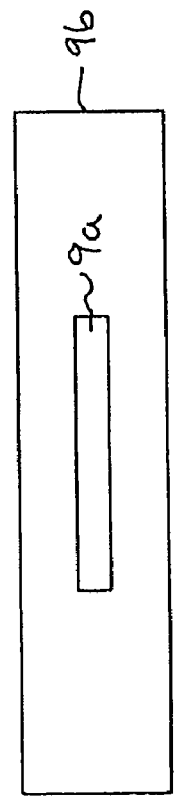
Figure 74:
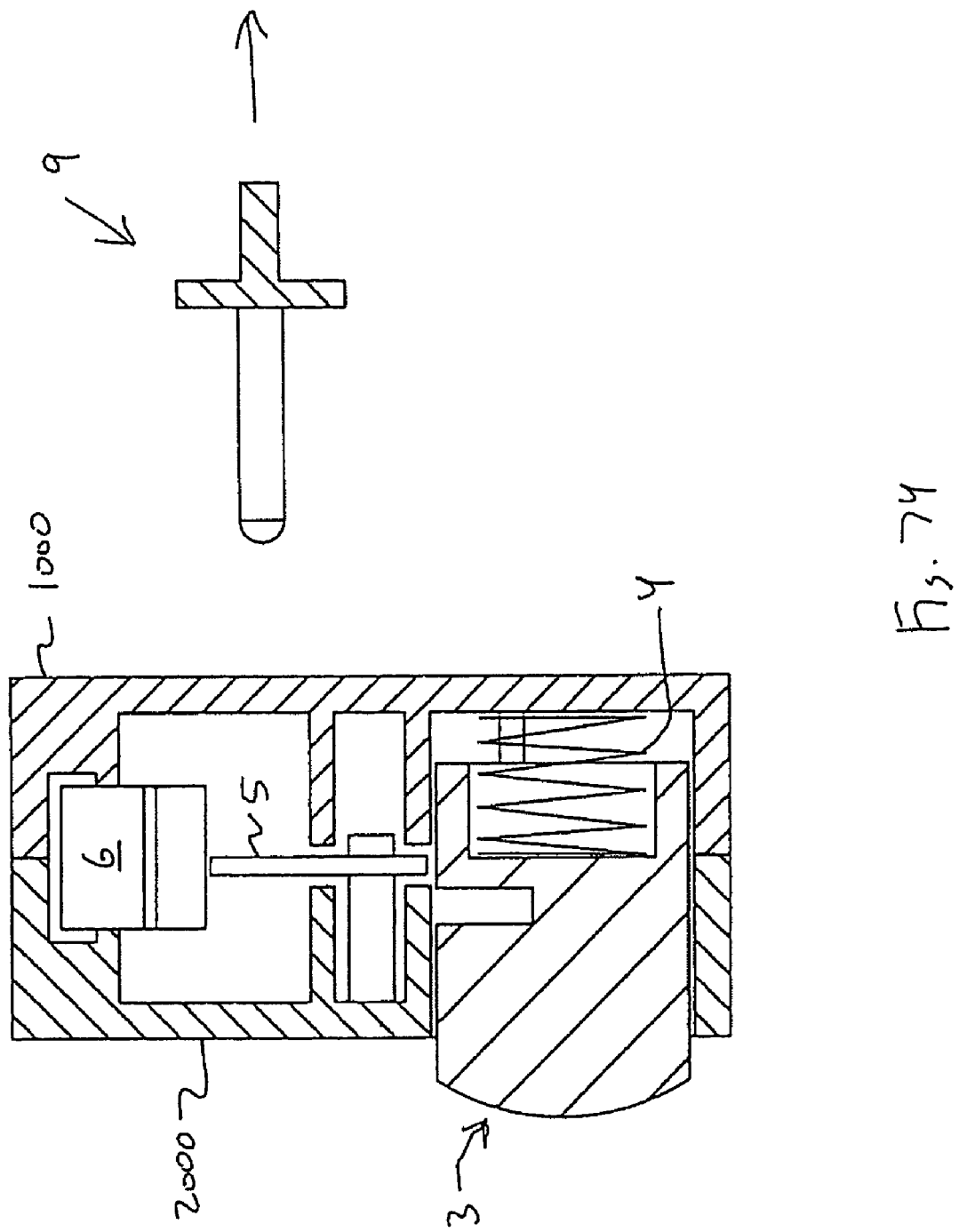
Figure 75:
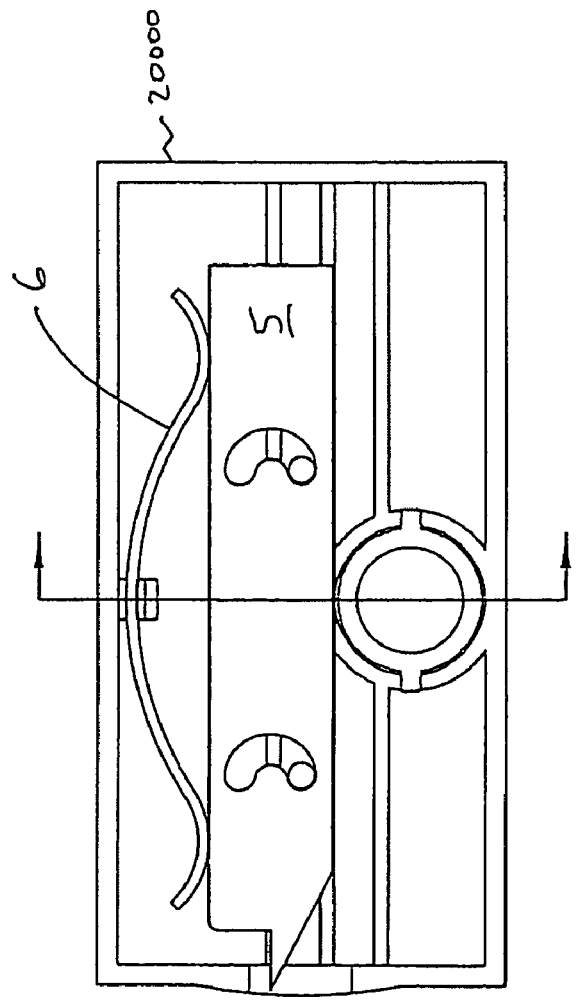
Figure 76:
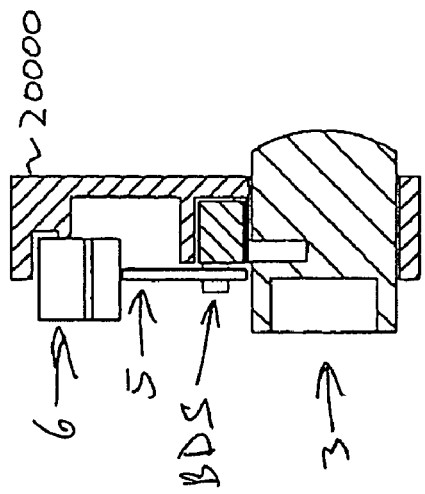
Figure 77:
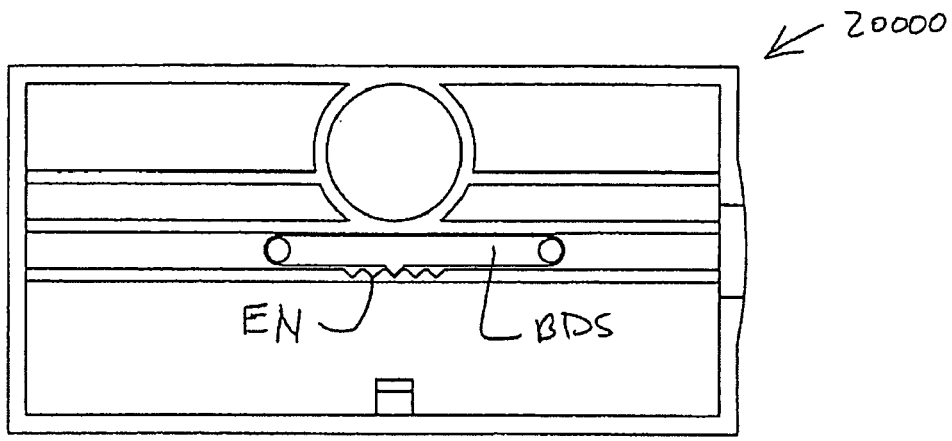
Figure 78:
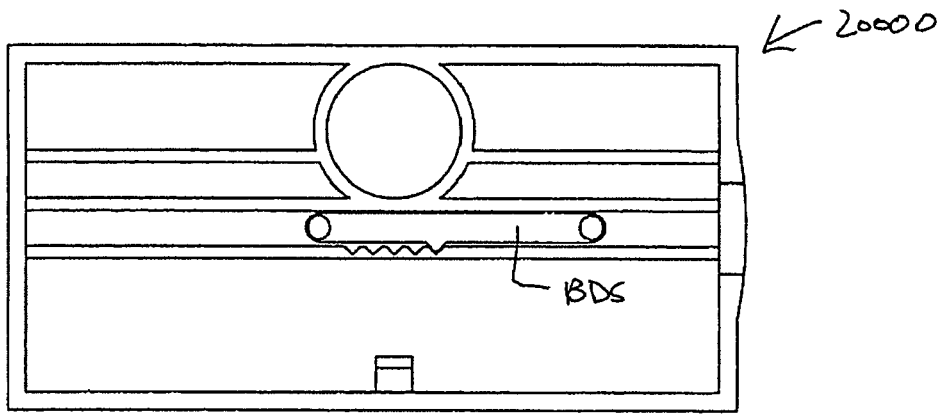
Figure 79:
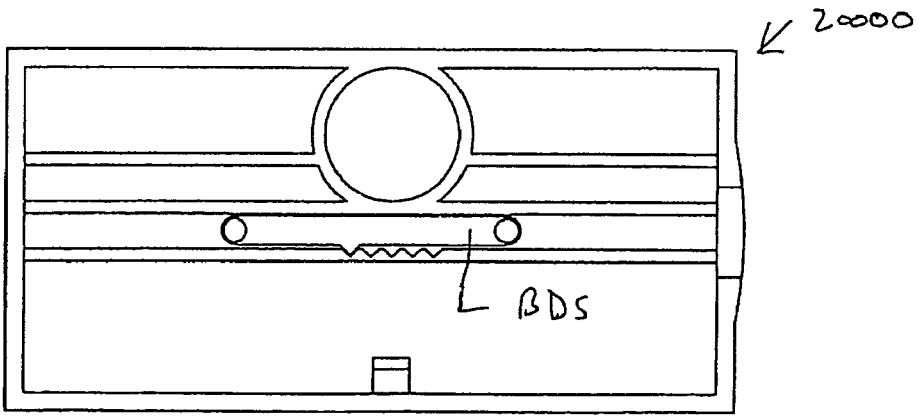
Figure 80:
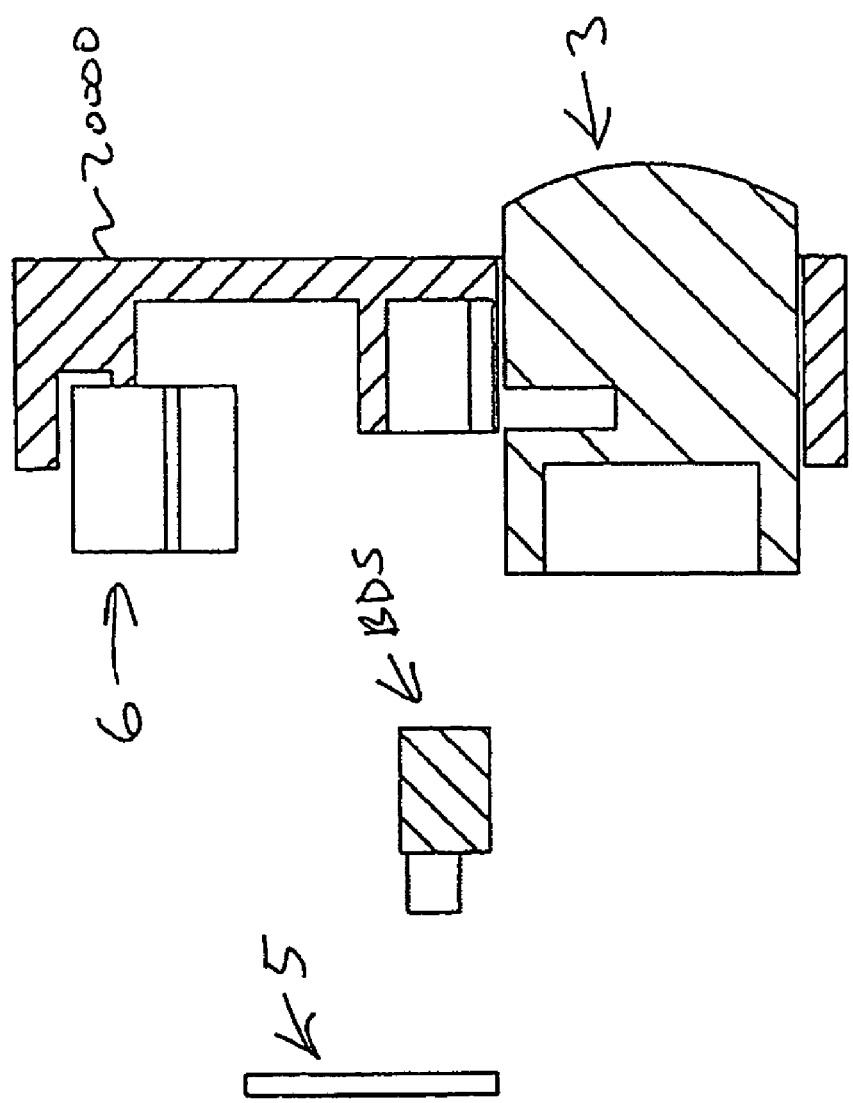
Figure 85:
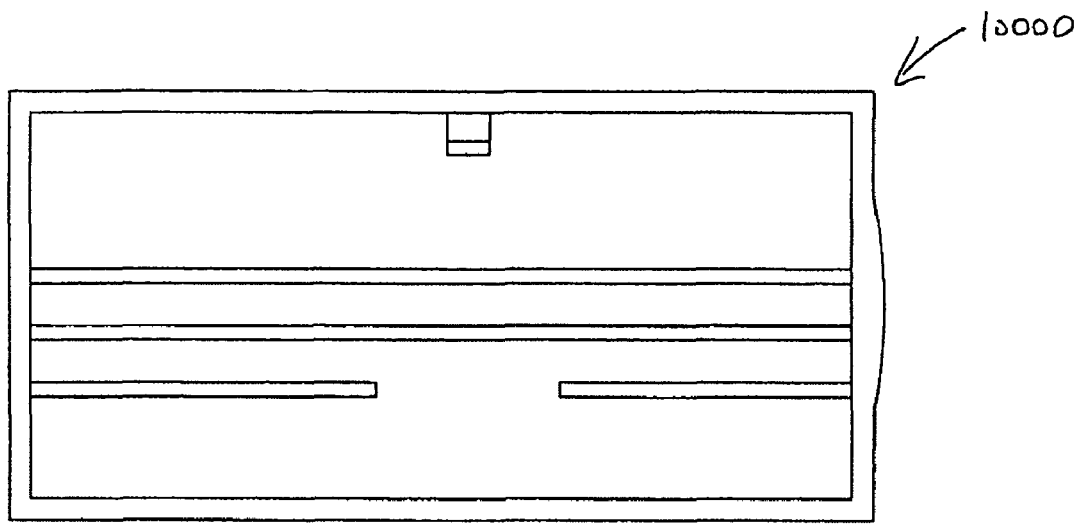
Figure 86:
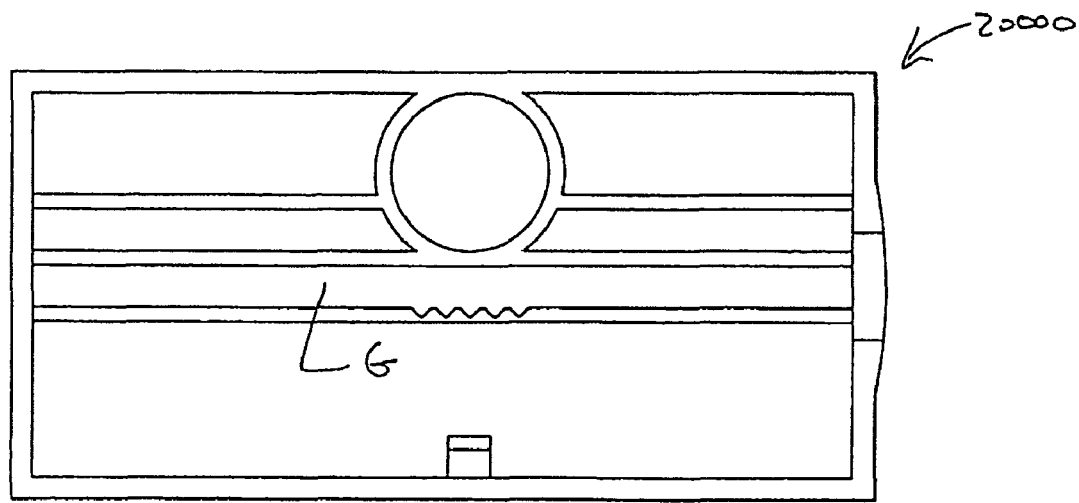
Figure 87:
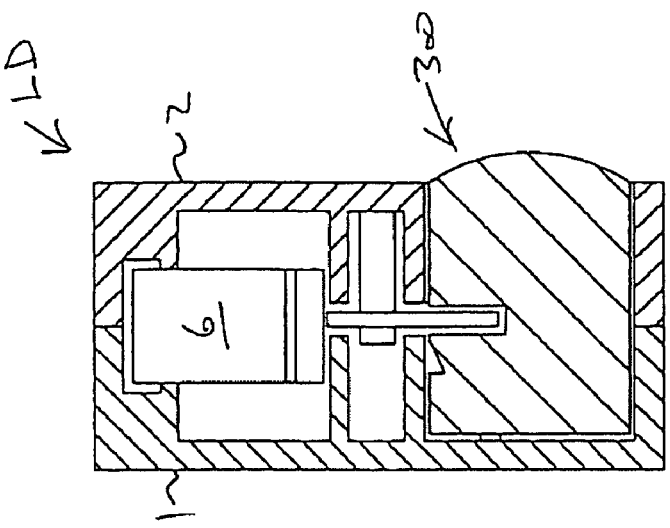
Figure 88:
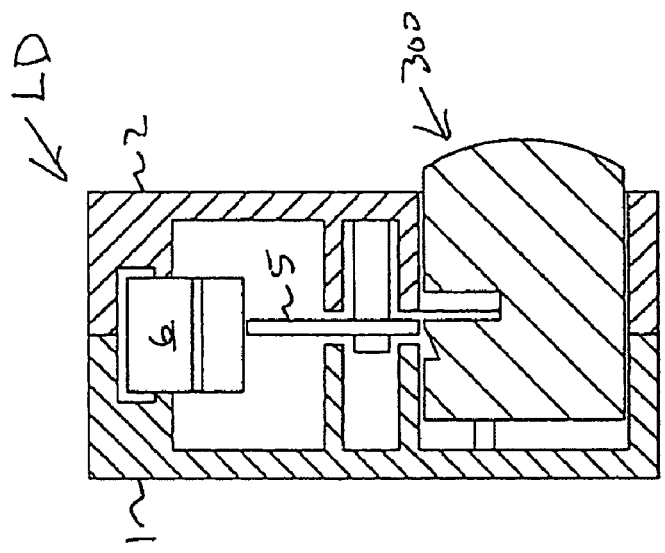
Figure 89:
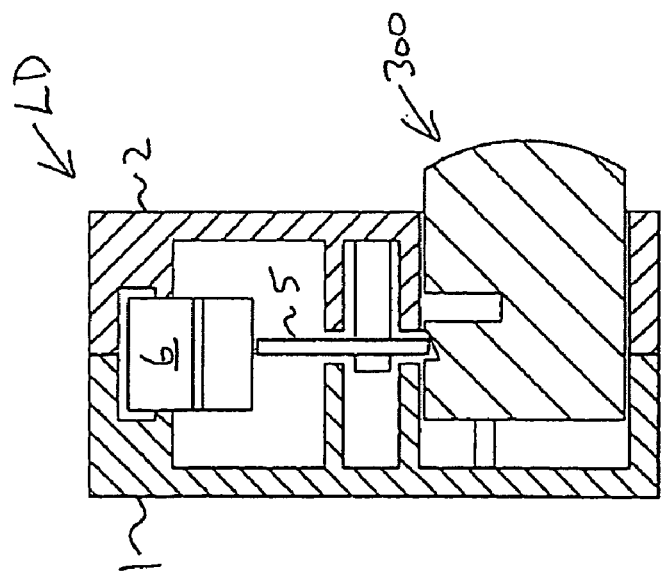
Figure 90C:
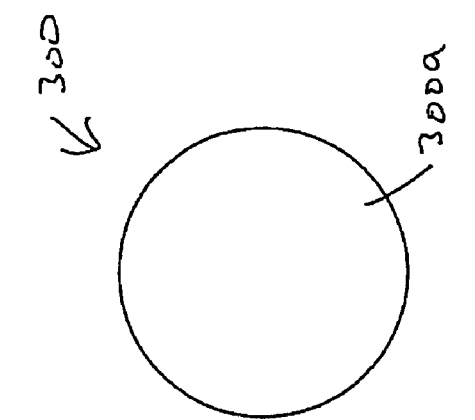
Figure 90B:
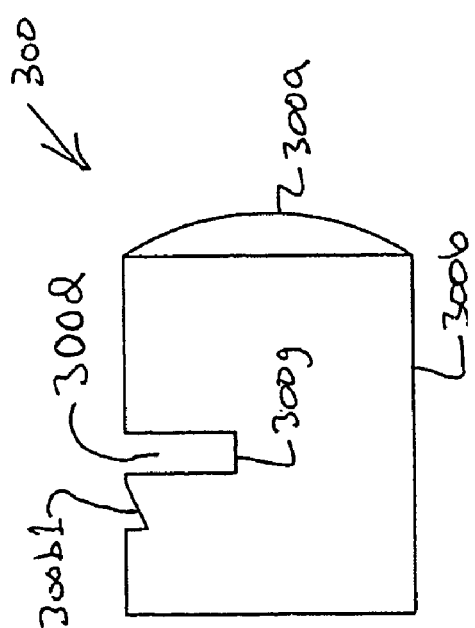
Figure 90A:
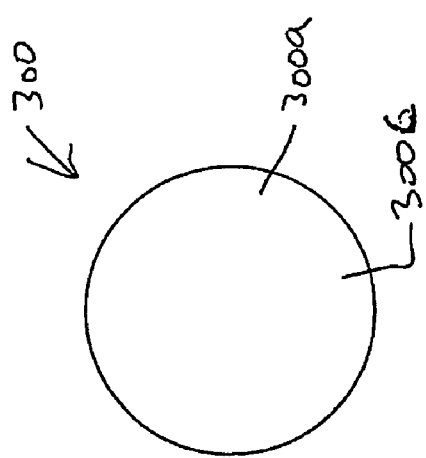
Figure 91:
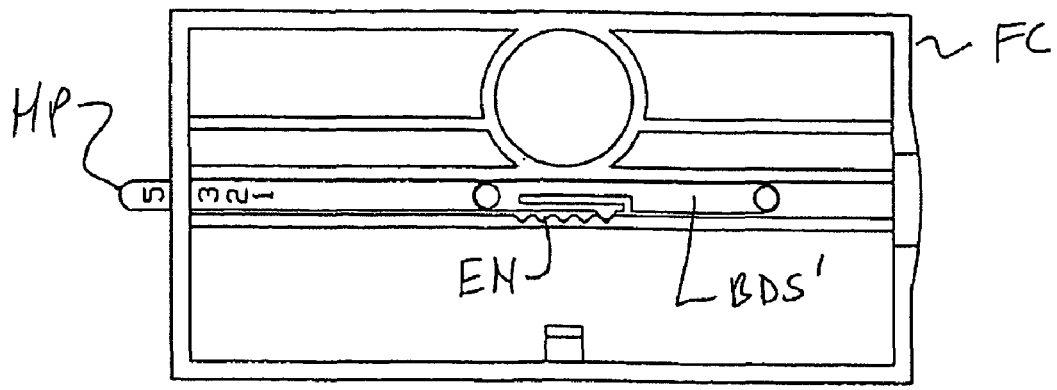
Figure 92:
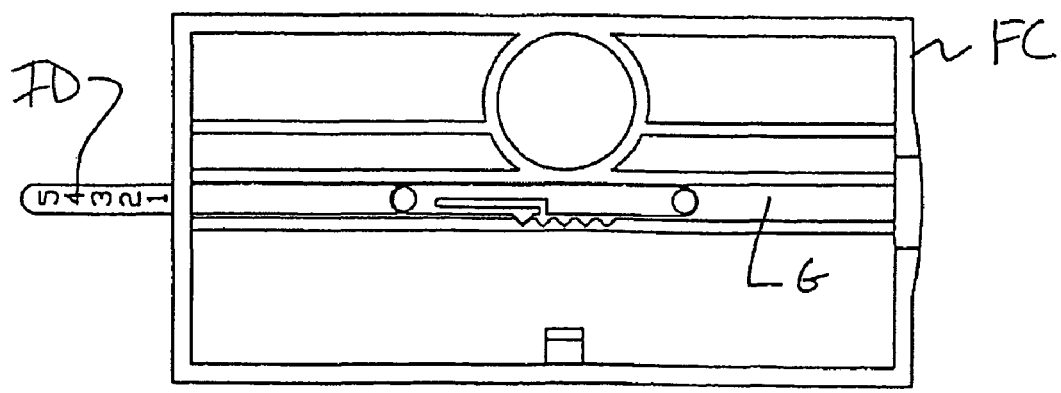
Figure 99:
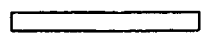
Figure 98:
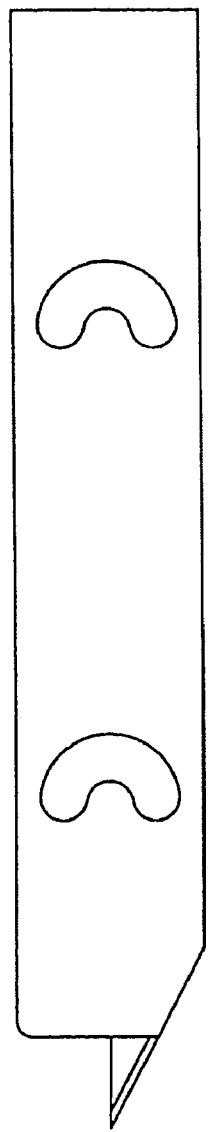
Figure 97:
Figure 102:
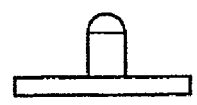
Figure 101:
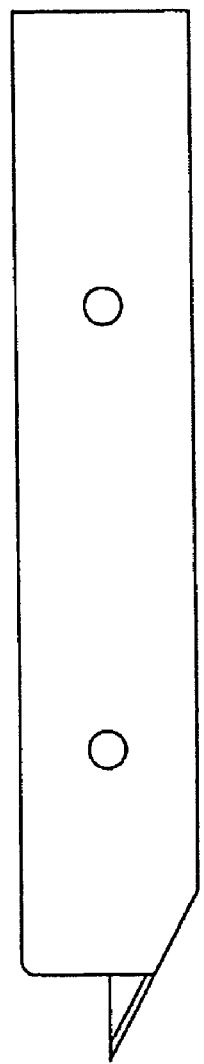
Figure 100:
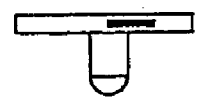
Figure 104:
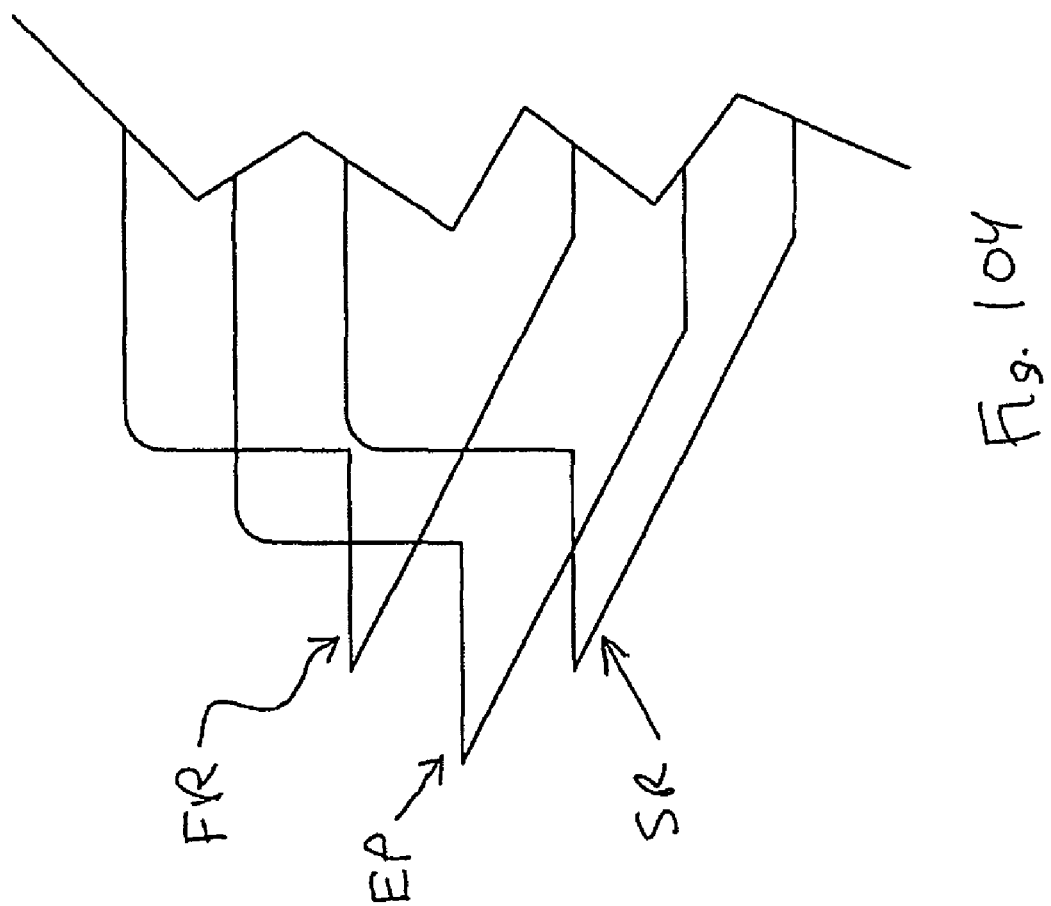
Figure 103:
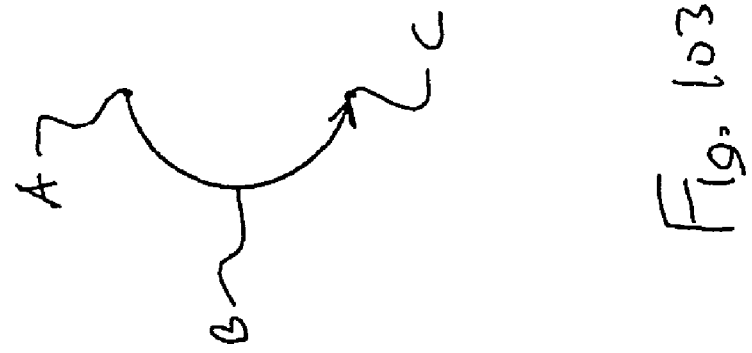
Figure 105:
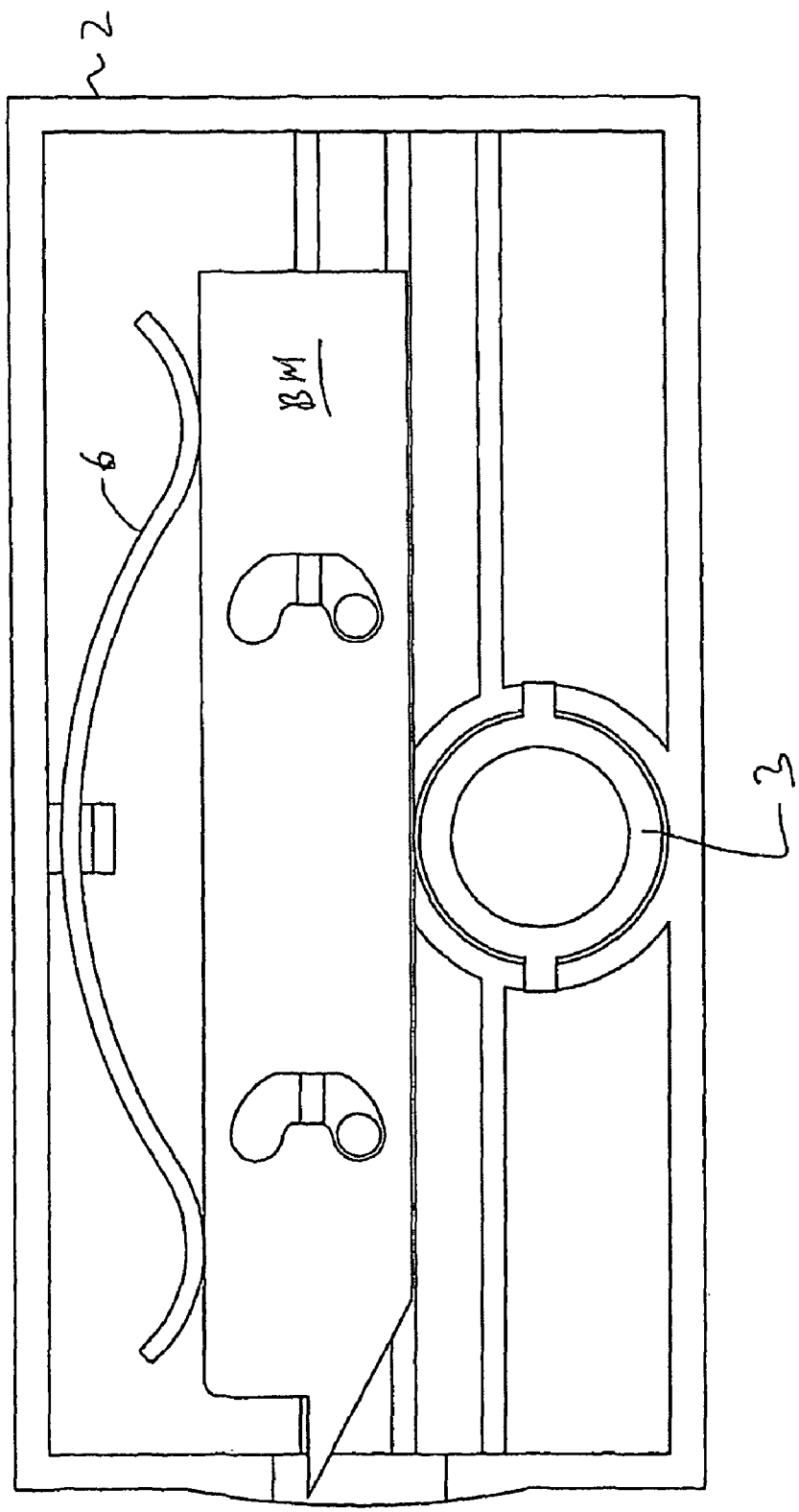
Figure 107:
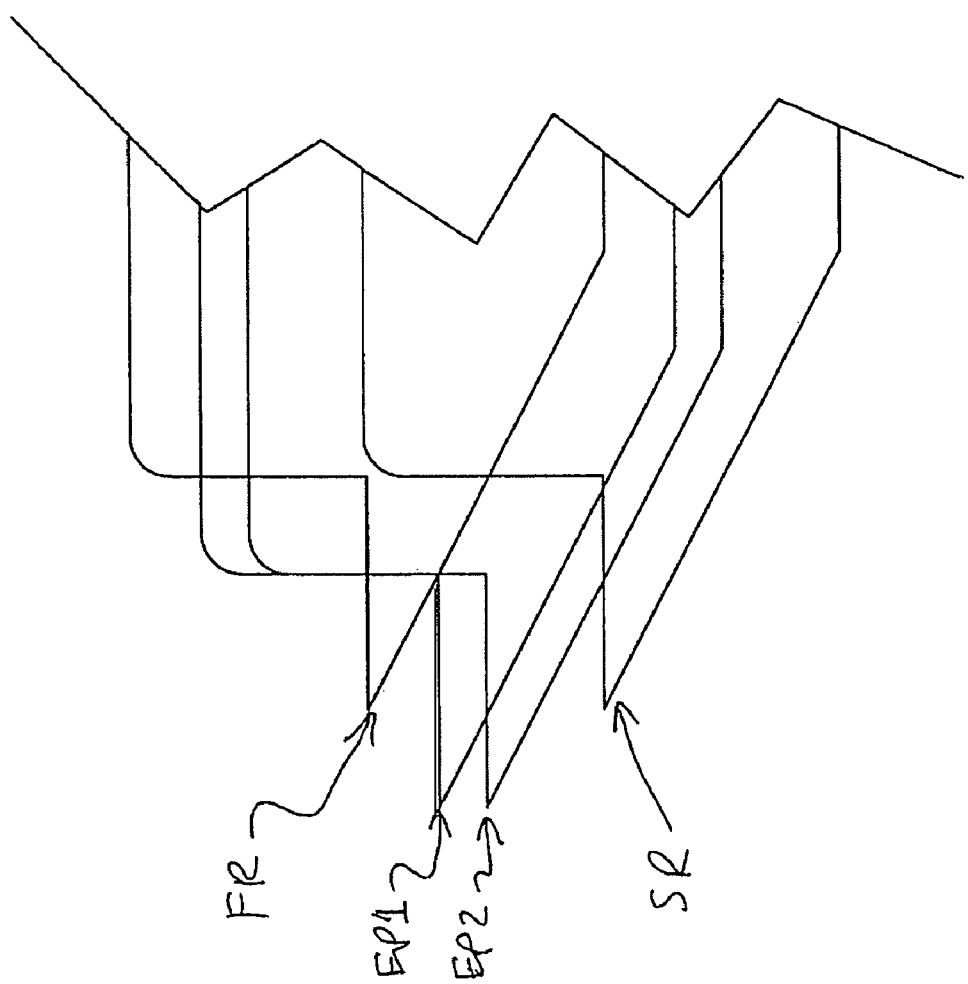
Figure 106:
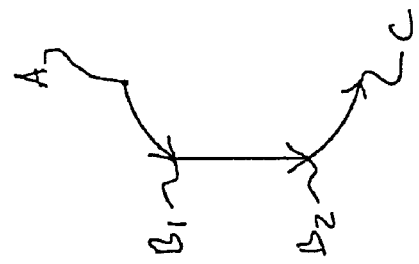
Figure 108:
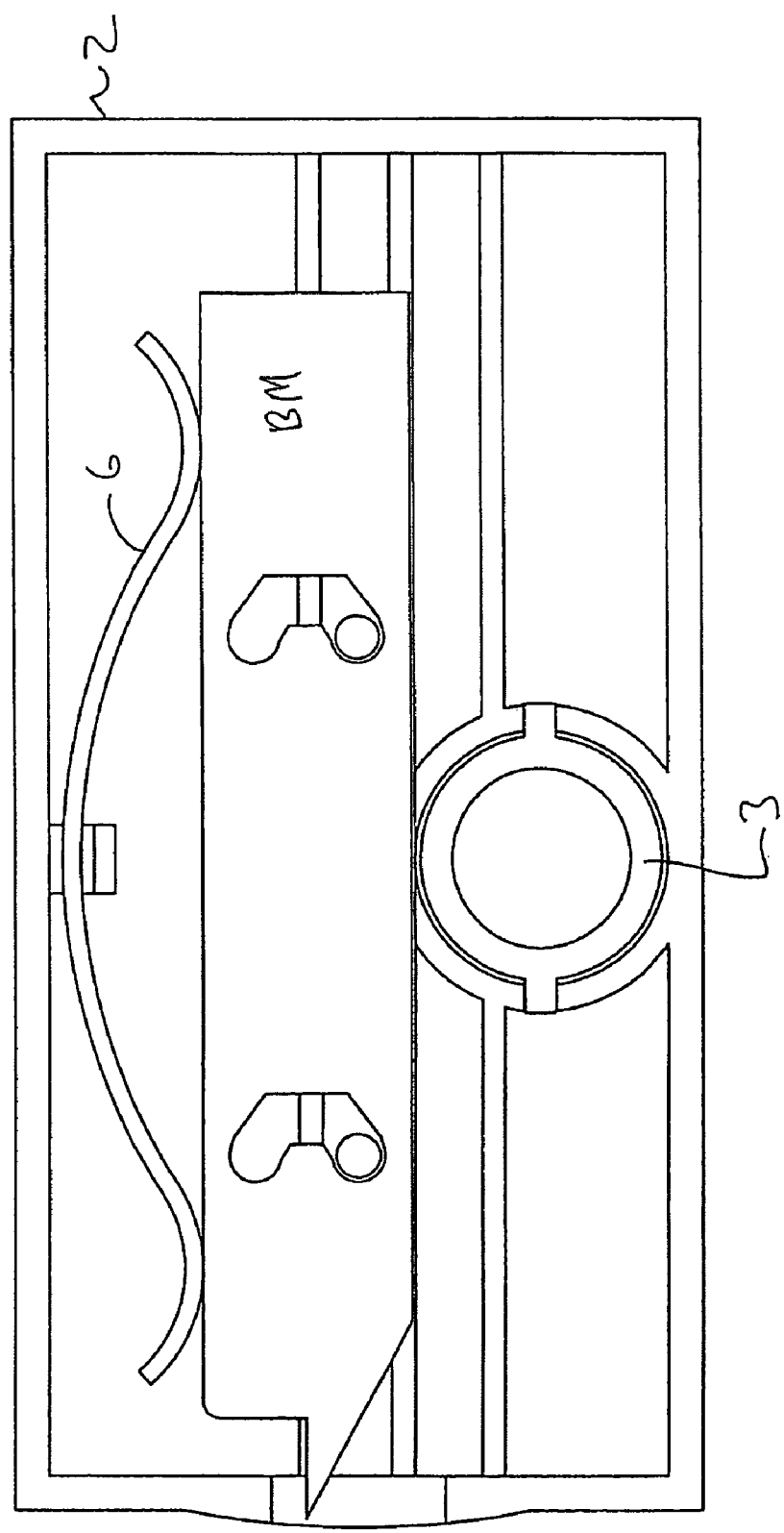
Figure 109:
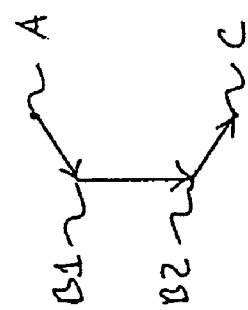
Figure 110:
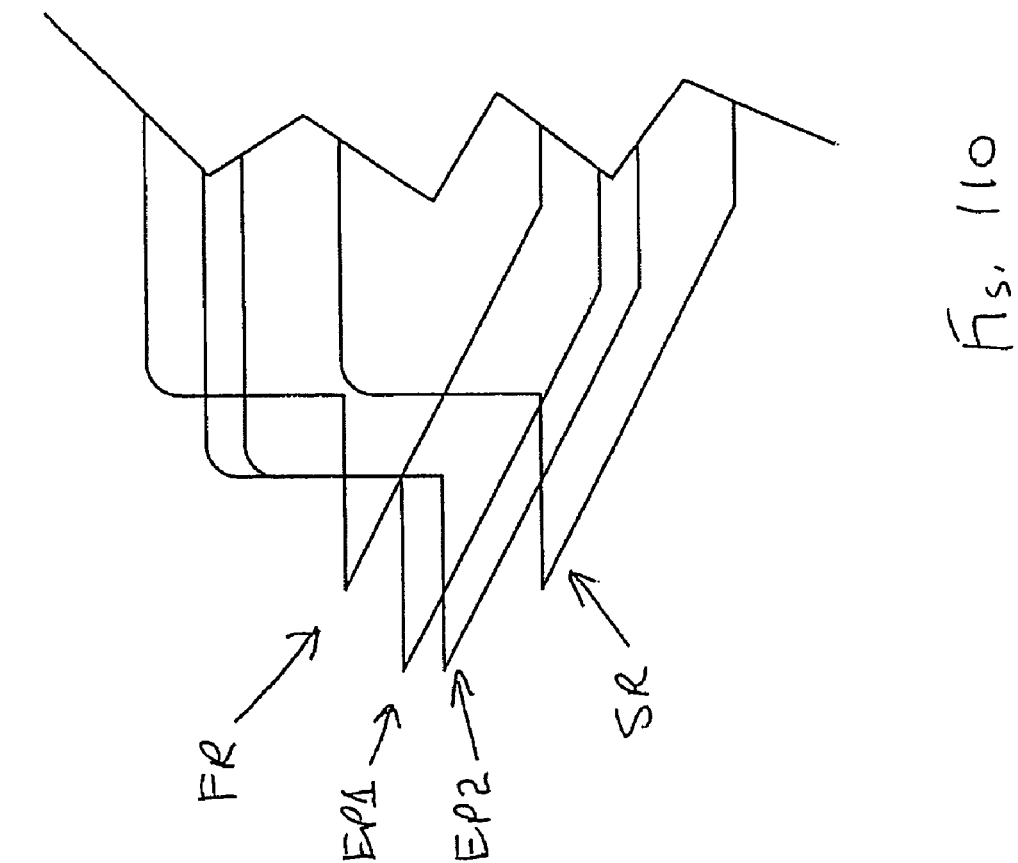
Figure 111:
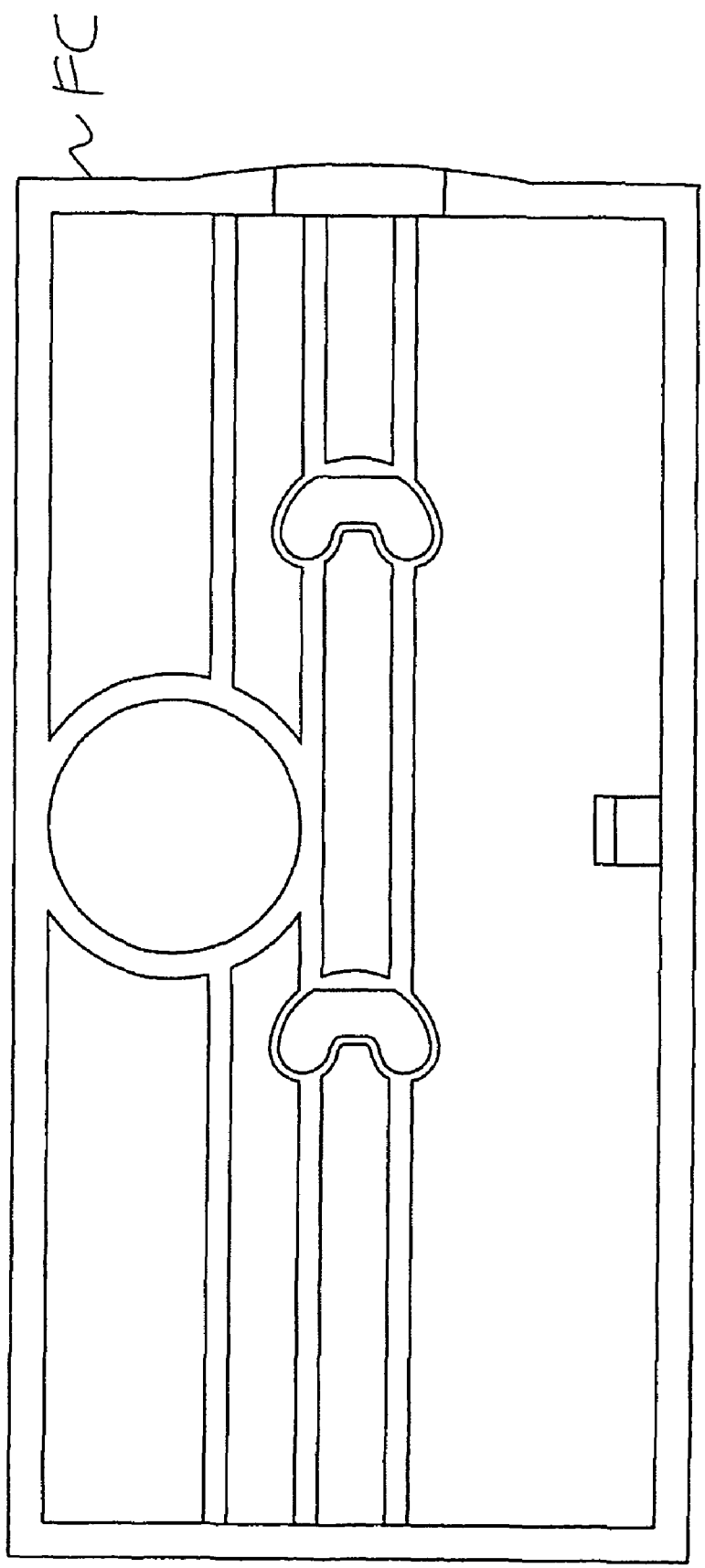
Figure 112:
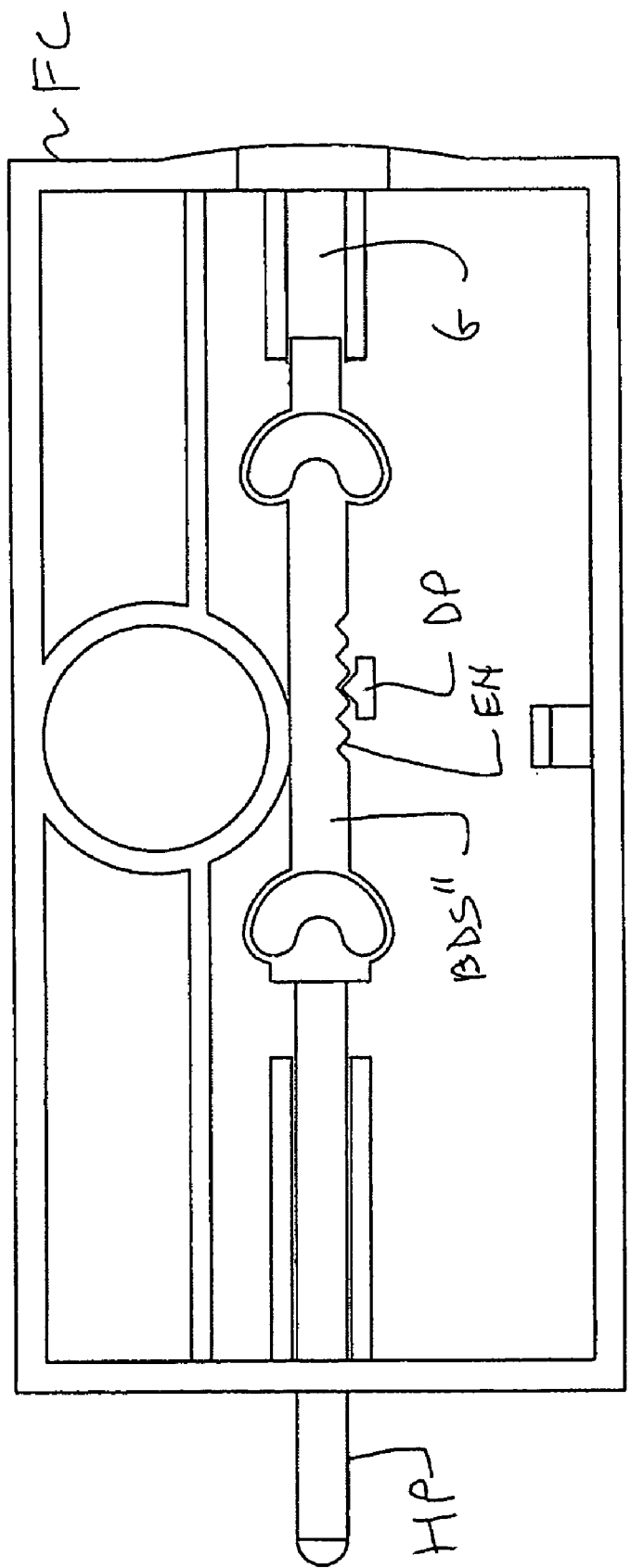

24 with the spring member, blade member and trigger button positioned therein. The arrangement/position of the spring member, blade member and trigger button are in the position shown in FIG. 31;

FIG. 35 shows a cross-section of FIG. 34;

FIG. 36 shows the lancet device of FIG. 24 with the rear cover portion removed. The figure thus shows an inside view of the front cover portion of the embodiment shown in FIG. 24 with the spring member, blade member and trigger button positioned therein. The arrangement/position of the spring member, blade member and trigger button are in the position shown in FIG. 32;

FIG. 37 shows a cross-section of FIG. 36;

FIG. 38 shows the lancet device of FIG. 24 with the rear cover portion removed. The figure thus shows an inside view of the front cover portion of the embodiment shown in FIG. 24 with the spring member, blade member and trigger button positioned therein. The arrangement/position of the spring member, blade member and trigger button are in the position shown in FIG. 33;

FIG. 39 shows a cross-section of FIG. 38;

FIG. 40 shows an inside view of the rear cover portion of the embodiment shown in FIG. 24;

FIG. 41 shows an inside view of the front cover portion of the embodiment shown in FIG. 24;

FIG. 42 shows a side view of the spring member used in the embodiment of FIG. 24;

FIG. 43 shows an end view of the spring member of FIG. 42;

FIG. 44 shows a side view of the blade member used in the embodiment of FIG. 24;

FIG. 45 shows a rear end view of the blade member of FIG. 44;

FIG. 46 shows a front view of another embodiment of the single-use blade lancet device;

FIG. 47 shows a side view of the embodiment shown in FIG. 46;

FIG. 48 shows the lancet device of FIG. 46 with the rear cover portion removed. The figure thus shows an inside view of the front cover portion of the embodiment shown in FIG. 46 with the spring member, blade member and trigger button positioned therein. The spring member, blade member and trigger button are of the type used in the embodiment of FIG. 1;

FIG. 49 shows an inside view of the rear cover portion of the embodiment shown in FIG. 46;

FIG. 50 shows an inside view of the front cover portion of the embodiment shown in FIG. 46;

FIG. 51 shows another embodiment of a lancet device with the rear cover portion removed. The device is generally similar to that of FIG. 1 except that the spring member used in the embodiment of FIG. 1 is replaced with two horizontally oriented coil springs and two horizontally movable sliding wedges. The figure shows an inside view of the front cover portion with the spring system, blade member and trigger button positioned therein. The arrangement/position of the spring member, blade member and trigger button are in a trigger-set/retracted position;

FIG. 52 shows the embodiment of FIG. 51 with the spring member, blade member and trigger button being the fully triggered/expanded position;

FIG. 53 shows a cross-section of FIG. 51;

FIG. 54 shows an inside view of the rear cover portion of the embodiment shown in FIG. 51;

FIG. 55 shows an inside view of the front cover portion of the embodiment shown in FIG. 51;

FIG. 56 shows another embodiment of a lancet device with the rear cover portion removed. The device is generally similar to that of FIG. 1 except that the spring member used in the embodiment of FIG. 1 is replaced with two vertically oriented coil springs and the blade member includes two vertically oriented projections which penetrate partially into the springs. The figure shows an inside view of the front cover portion with the spring system, blade member and trigger button positioned therein. The arrangement/position of the spring member, blade member and trigger button are in a trigger-set/retracted position;

FIG. 57 shows the embodiment of FIG. 56 with the spring member, blade member and trigger button being the fully triggered/expanded position;

FIG. 58 shows a cross-section of FIG. 56;

FIG. 59 shows an inside view of the rear cover portion of the embodiment shown in FIG. 56;

FIG. 60 shows an inside view of the front cover portion of the embodiment shown in FIG. 56;

FIGS. 61 and 62 show side and front views of another embodiment of a lancet device. The device is generally similar to that of FIG. 1 except that a removable locking device is used to lock the blade member in the trigger-set/retracted position;

FIG. 63 shows a front view of the embodiment shown in FIGS. 61-62 with the locking device in the installed/inserted position;

FIG. 64 shows a rear side view of the embodiment shown in FIGS. 61-62 with the locking device in the installed/inserted position;

FIG. 65 shows a cross-section view through arrows in FIG. 64;

FIG. 66 shows a front side view of the embodiment shown in FIGS. 61-62;

FIG. 67 shows a cross-section view through arrows in FIG. 66;

FIG. 68 shows an inside view of the rear cover portion of the embodiment shown in FIGS. 61-62;

FIG. 69 shows the lancet device of FIGS. 61-62 with the rear cover portion removed. The figure thus shows an inside view of the front cover portion of the embodiment shown in FIG. 61-62 with the spring member, blade member and trigger button positioned therein. The arrangement/position of the spring member, blade member and trigger button are in the trigger-set/retracted position;

FIG. 70 shows a side view of the locking device used in the embodiment of FIGS. 61-62;

FIG. 71 shows a bottom view of the locking device of FIG. 70;

FIG. 72 shows a top view of the locking device of FIG. 70;

FIG. 73 shows an end view of the locking device of FIG. 70;

FIG. 74 shows the locking device removed from the lancet device of FIGS. 61-62;

FIG. 75 shows another embodiment of a lancet device with the rear cover portion removed. The device is generally similar to that of FIG. 1 except that the front cover uses an adjustable blade setting device. The figure shows an inside view of the front cover portion with the spring member, blade member and trigger button positioned therein. The arrangement/position of the spring member, blade member and trigger button are in a trigger-set/retracted position;

FIG. 76 shows a cross-section view through arrows in FIG. 75;

FIG. 77 shows an inside view of the front cover portion used in the lancet device of FIG. 75. The adjustable blade setting device is shown in a horizontal groove and is positioned in an intermediate adjustment position;

FIG. 78 shows an inside view of the front cover portion used in the lancet device of FIG. 75. The adjustable blade setting device is shown in a horizontal groove and is positioned in an adjustment position which causes the blade to penetrate a maximum amount into the skin of a user;

FIG. 79 shows an inside view of the front cover portion used in the lancet device of FIG. 75. The adjustable blade setting device is shown in a horizontal groove and is positioned in an adjustment position which causes the blade to penetrate the least amount into the skin of a user;

FIG. 80 shows the cross-section of FIG. 76 in a partially dis-assembled state. The blade member and the adjustable blade setting device are shown removed/dis-assembled from the front cover portion;

FIG. 81 shows a side view of the adjustable blade setting device used in the embodiment of FIG. 75;

FIG. 82 shows a top view of the adjustable blade setting device of FIG. 81;

FIG. 83 shows an end view of the adjustable blade setting device of FIG. 81;

FIG. 84 shows a rotated end view of FIG. 83;

FIG. 85 shows an inside view of the rear cover portion of the embodiment shown in FIG. 75;

FIG. 86 shows an inside view of the front cover portion of the embodiment shown in FIG. 75;

FIG. 87 shows a cross-section view through an embodiment similar to that of FIG. 1 and illustrating the blade in a trigger-set/retracted position. This embodiment differs from that of FIG. 1 by utilizing a different trigger button and by not utilizing a spring for the trigger button;

FIG. 88 shows the cross-section view of FIG. 87 and illustrating the blade member in an intermediate position as it moves from the initial position shown in FIG. 87 to the final position shown in FIG. 89;

FIG. 89 shows the cross-section view of FIG. 87 and illustrating the blade member in triggered/expanded position;

FIG. 90a shows a rear view of the trigger button used in the embodiment of FIGS. 87-89;

FIG. 90b shows a side view of the trigger button used in the embodiment of FIGS. 87-89;

FIG. 90c shows a front view of the trigger button used in the embodiment of FIGS. 87-89;

FIG. 91 shows another embodiment of a lancet device with the rear cover portion, blade member, spring member, and trigger button removed. The device is generally similar to that of FIG. 1 except that the front cover uses an adjustable blade setting device whose handle portion includes indicia and extends through an opening in a rear wall of the front cover portion. The adjustable blade setting device is shown in a horizontal groove and is positioned in an adjustment position which causes the blade to penetrate a maximum amount into the skin of a user;

FIG. 92 shows an inside view of the front cover portion used in the lancet device of FIG. 91. The adjustable blade setting device is shown in a horizontal groove and is positioned in an adjustment position which causes the blade to penetrate the least amount into the skin of a user;

FIG. 93 shows a side view of the adjustable blade setting device used in the embodiment of FIG. 91;

FIG. 94 shows a top view of the adjustable blade setting device of FIG. 93;

FIG. 95 shows an end view of the adjustable blade setting device of FIG. 93;

FIG. 96 shows an end view of the adjustable blade setting device of FIG. 94;

FIG. 97 shows a front end view of an alternative blade member which can be used in the embodiments of FIGS. 1, 46, 51, 56, 61, 75, 87 and 91;

FIG. 98 shows a side view of the blade member of FIG. 97;

FIG. 99 shows a rear end view of the blade member of FIG. 97;

FIG. 100 shows a front end view of an alternative blade member which can be used in the embodiment of FIG. 24;

FIG. 101 shows a side view of the blade member of FIG. 100;

FIG. 102 shows a rear end view of the blade member of FIG. 100;

FIG. 103 illustrates the arcuate movement of the blade member in the embodiments shown in FIGS. 1-102 from an initial retracted position A, to a maximum depth/extended position B and to a final retracted position C;

FIG. 104 illustrates the three positions (superimposed on one another) of the tip of the blade member in the positions shown in FIG. 103. The tip positions are a first retracted position FR, an extended position EP, and a second retracted position SR;

FIG. 105 shows another embodiment of a lancet device with the rear cover portion removed. The device is generally similar to that of FIG. 1 except that the blade member (which uses arc-shaped recesses) used in the embodiment of FIG. 1 is replaced with a blade member having non-continuously curved and/or interrupted cam recesses. The figure shows an inside view of the front cover portion with the spring member, blade member and trigger button positioned therein. The arrangement/position of the spring member, blade member and trigger button are in a trigger-set/retracted position;

FIG. 106 illustrates the semi-arcuate/straight movement of the blade member in the embodiment shown in FIG. 105 from an initial retracted position A, to a maximum depth/extended cutting path B1 to B2, and to a final retracted position C;

FIG. 107 illustrates the four positions (superimposed on one another) of the tip of the blade member in the positions shown in FIG. 106. The tip positions are a first retracted position FR, a straight cutting path position from points EP1 to EP2, and a second retracted position SR;

FIG. 108 shows another embodiment of a lancet device with the rear cover portion removed. The device is generally similar to that of FIG. 1 except that the blade member (which uses arc-shaped recesses) used in the embodiment of FIG. 1 is replaced with a blade member having non-curved cam recesses. The figure shows an inside view of the front cover portion with the spring member, blade member and trigger button positioned therein. The arrangement/position of the spring member, blade member and trigger button are in a trigger-set/retracted position;

FIG. 109 illustrates the three straight movements of the blade member in the embodiment shown in FIG. 108 from an initial retracted position A, to a maximum depth/extended straight cutting path B1 to B2, and to a final retracted position C;

FIG. 110 illustrates the four positions (superimposed on one another) of the tip of the blade member in the positions shown in FIG. 109. The tip positions are a first retracted position FR, a straight cutting path position from points EP1 to EP2, and a second retracted position SR;

FIG. 111 shows another embodiment of a lancet device with the rear cover portion, the spring member, the blade member, and the trigger button removed. The lancet device embodiment is formed by replacing the front cover portion of the embodiment shown in FIG. 24 with the one shown in FIG. 111; and FIG. 112 shows still another embodiment of a lancet device with the rear cover portion, the spring member, the blade member, and the trigger button removed. The lancet device embodiment is formed by replacing the front cover portion of the embodiment shown in FIG. 24 with the one shown in FIG. 112. The device is generally similar to that of FIG. 24 except that the front cover uses an adjustable blade setting device whose handle portion may includes indicia and extends through an opening in a rear wall of the front cover portion. The adjustable blade setting device is shown in an interrupted horizontal groove and is positioned in an intermediate adjustment position which causes the blade to penetrate a medium amount into the skin of a user.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-23 show a first non-limiting embodiment of a single-use and/or disposable blade lancet device LD. Lancet device LD has a lancet body made up of an upper or front body portion 2 and a lower or rear body portion 1. These parts 1 and 2 are connected to each other, e.g., using adhesives and/or fasteners and/or welding and/or snap-together holding mechanisms (not shown), when the lancet device LD is initially assembled. A blade member 5 is movably disposed within the body parts 1, 2 (see FIGS. 9-10). Although not shown, a front end cover can also be removably connected or attached to a front portion of the body parts 1, 2 as is exemplified in the embodiment described in copending U.S. patent application Ser. No. 10/441,065 filed on May 20, 2003, the entire disclosure of which is hereby expressly incorporated by reference in its entirety.

As with many lancet devices, the lancet device defines a plane or surface SCS which is, e.g., configured to contact (i.e., be positioned against) a user's skin. However, unlike known lancet devices, the instant embodiment may utilize an outwardly curved skin engaging surface SCS beyond which the tip portion 5a of the lancet blade member 5 can extend and/or project. Of course, the invention also contemplates using a planar front skin engaging surface SCS, e.g., of the type described in U.S. Pat. No. 6,258,112, the disclosure of which is hereby expressly incorporated by reference in its entirety. Although not preferred for use as a blade lancing device, the device of the invention can also possibly be used without contacting the skin of a user.

As can be seen in FIGS. 1-4, the lancet body can have a generally rectangular shape and can preferably also have an ergonomic shape to facilitate comfortable gripping/holding. Of course, the invention contemplates other shapes provided that they result in a relatively inexpensive design and/or which is economical to produce. As explained above, the front end of the lancet device includes an outwardly curved skin engaging surface SCS which is defined by outer front outwardly curved surfaces of both cover parts 1, 2. A lancet blade opening BO extends through one or both of the front walls F of the cover parts 1, 2 and serves to allow the lancet blade member 5 to penetrate beyond the surface SCS (see FIG. 16). A trigger, preferably in the form of a trigger button 3 is movably mounted to the lancet body. In the instant embodiment, the trigger button 3 is circularly/cylindrically-shaped for reasons of aesthetic design. However, the invention contemplates other shapes for the trigger button 3 such as, e.g., oval, triangular, square, polygonal, etc. In the instant embodiment, the trigger button 3 is generally centrally mounted, relative to walls F and R, to a lower area of the front cover 2. However, the invention contemplates other locations and/or positions for the trigger button 3, provided such locations allow the lancet device to function properly. Other ways of associating the trigger button on the housing are expressly contemplated, such as, e.g., being integral with the housing and acting as a living hinge or spring. The trigger button 3 is seated in a trigger opening 2d formed in the front cover 2 and is sized to slide within the opening 2d in a smooth low-friction manner. The trigger button 3 has a finger engaging (e.g. push button) portion 3a (see FIGS. 8a-8c) that can be pushed into the lancet body (see FIGS. 9-11). The trigger button 3 is biased towards an extended position (see FIG. 9) via a coil compression spring 4. This biasing force can be overcome, of course, when the trigger button 3 is pushed into the lancet body (see FIGS. 10 and 11) by applying a force to the finger engaging portion 3a. However, because the trigger button 3 includes a slot 3d, once the blade member 5 enters the slot 3d (see FIGS. 10 and 11), and engages the bottom surface 3g of the slot 3d under the biasing force of the leaf spring 6, the trigger button 3 is prevented from moving back by the blade member 5 under the action of the spring 4 to the position shown in FIG. 9. Thus, once triggered, the lancet device is automatically rendered unusable again—thereby rendering the device a single-use device.

Although not shown, the lancet body can preferably includes a viewing opening or be made of a transparent/translucent material so that the user will easily note that the device is properly set and/or has not be used. The opening or window can be formed in the front cover 2 and can be arranged in a convenient area which allows the user to see the position of the blade member 5. The opening or window, of course, can have any desired shape or configuration and can be located at any desired location provided that the user is able to discern the setting position of the blade member 5.

Figure 8C:
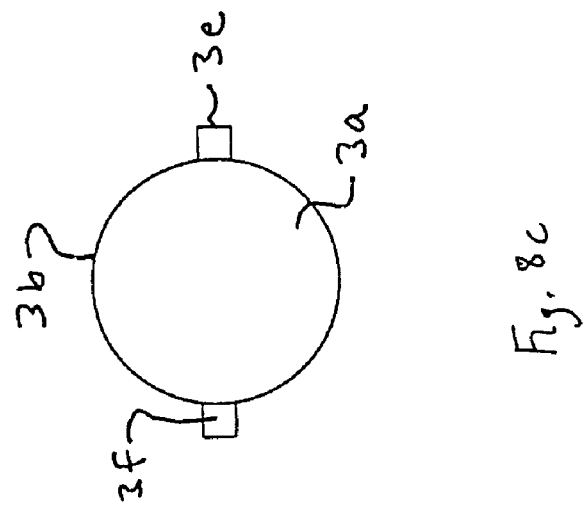
FIG. 8c shows a front view of the trigger button used in the embodiment of FIG. 1.
Figure 8B:
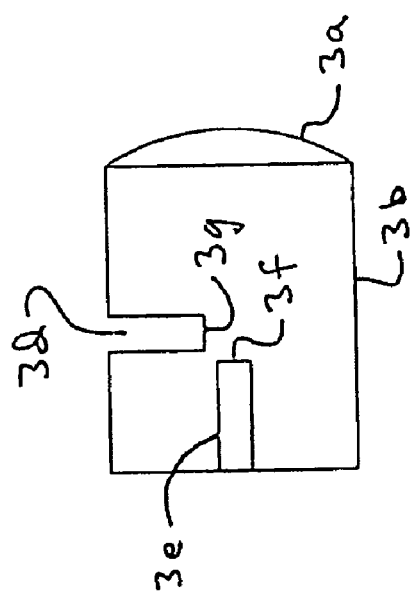
FIG. 8b shows a side view of the trigger button used in the embodiment of FIG. 1.
Figure 8A:
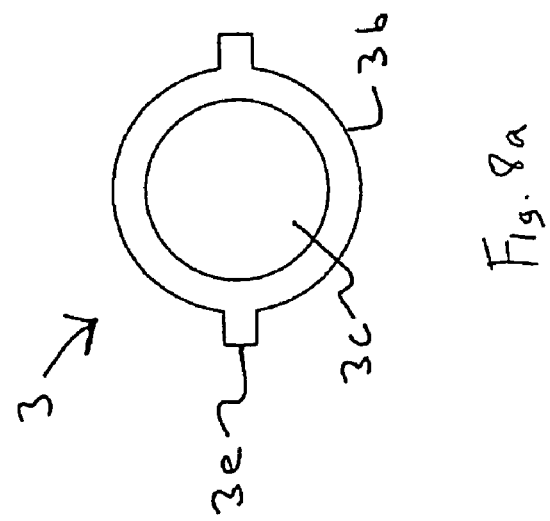
FIG. 8a shows a rear view of the trigger button used in the embodiment of FIG. 1.

FIGS. 8a-8c show rear, side and front views of the trigger button 3. The trigger button 3 can preferably be made as one-piece structure by e.g., injection molding. In this regard, it is preferably made of a plastic or synthetic resin such as, e.g., ABS plastic. The trigger button 3 may also be made of ABS-Red and have a finish designated as SPI-A2. Of course, other materials and/or finishes may be utilized, without leaving the scope of the invention. Additionally, by way of non-limiting example, the trigger button 3 may have an overall length that is approximately ½" (i.e., measured horizontally across FIG. 8b). Moreover, the trigger button 3 may even be made of a plurality of sections of parts which are joined together to form the complete trigger button 3, without leaving the scope of the invention, although it is preferred that it be formed a one-piece member. It would be even more preferable if the trigger button 3 were integrally formed with the lancet body, and in particular, integrally formed with the upper body part 2 and connected thereto with a living hinge (not shown).

With reference to FIGS. 22 and 23, the lancet blade member 5 can be a stainless steel one-piece stamped member whose tip portion 5a is shaped with an angled sharpened edge 5b. The blade member 5 also includes a front edge portion 5c and a generally rectangular-shaped body portion which is formed with two spaced-apart arc-shaped through cam slots 5d and 5e. Alternatively, the blade member 5 can be of a multi-piece structure (see e.g., FIGS. 97-99) in which a stainless steel tip portion (see e.g., FIGS. 97-99) is mounted to a body portion which can be made of, e.g., synthetic resin or polymer material. By way of non-limiting example, the blade member 5 can have a thickness of between approximately 0.010" to approximately 0.050".

Figure 5:
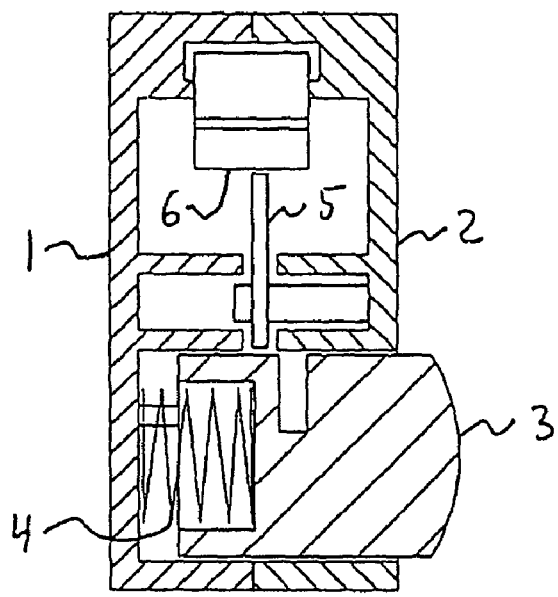
FIG. 5 shows a cross-section view through the arrows in FIG. 4.
Figure 6:
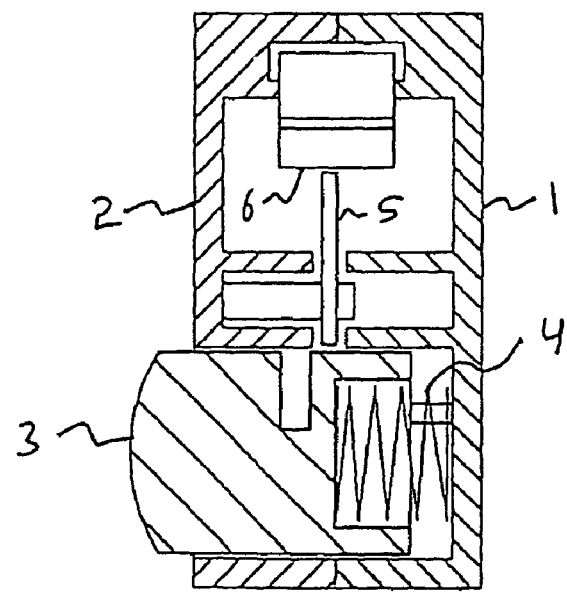
FIG. 6 shows a cross-section view through the arrows in FIG. 3.

As can be seen in FIGS. 5-7, the lancet device LD uses a coil compression spring 4 mounted therein. In this regard, the spring 4, which can be made of spring steel and which can have the form of a helical coil spring, is arranged between an inner wall of the rear cover 1 and extends into an opening 3c of the trigger button 3. This spring 4 causes (and/or biases) the trigger button 3 to move towards an extended position, i.e., an initial prior-use position before the trigger 3 is activated. As discussed above, the trigger button 3 includes a cylindrical 3b portion that slides within the opening 2d of the lancet body and is mounted to the upper or front body part 2.

Figure 11:
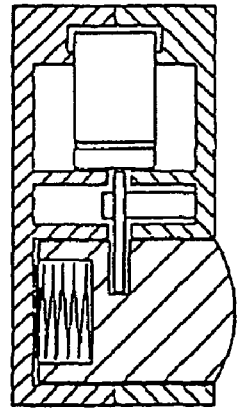
FIG. 11 shows a cross-section view through the arrows in FIG. 4 and illustrating the blade member in triggered/expanded position.
Figure 16:
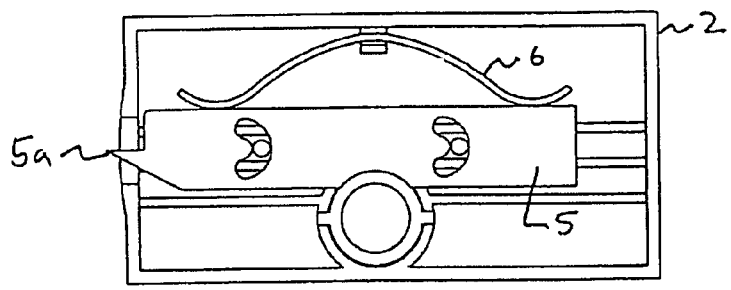
FIG. 16 shows the lancet device of FIG. 1 with the rear cover portion removed. The figure thus shows an inside view of the front cover portion of the embodiment shown in FIG. 1 with the spring member, blade member and trigger button positioned therein. The arrangement/position of the spring member, blade member and trigger button are in the position shown in FIG. 10.
Figure 17:
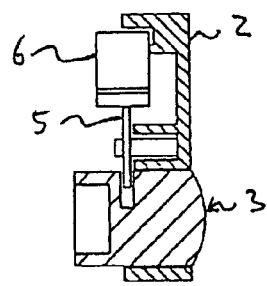
FIG. 17 shows a cross-section of FIG. 16.
Figure 18:
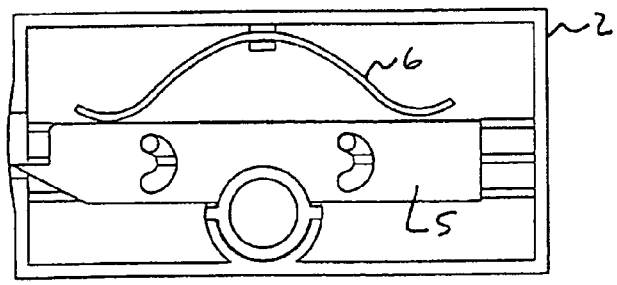
FIG. 18 shows the lancet device of FIG. 1 with the rear cover portion removed. The figure thus shows an inside view of the front cover portion of the embodiment shown in FIG. 1 with the spring member, blade member and trigger button positioned therein. The arrangement/position of the spring member, blade member and trigger button are in the position shown in FIG. 11.
Figure 19:
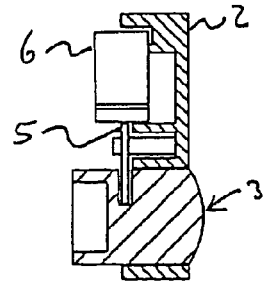
FIG. 19 shows a cross-section of FIG. 18.

As noted above, the leaf spring 6, which can be a stamped spring steel member, is utilized to bias and/or move the blade member 5 from an initial retracted/pre-use position (see FIGS. 5, 6, 9, 14 and 15) to an extended/second retracted position (see FIGS. 11, 18 and 19). The spring 6 has a central curved portion 6a (see FIG. 20) which is secured to the lancet body between opposing grooves formed by L-shaped projecting portions 1a and 2a (see FIG. 7) and two generally symmetrical curved end portions 6b and 6c (see FIG. 20) which contact and/or engage the blade member 5 (see FIGS. 14-18). The leaf spring 6 is thus compressed in the position shown in FIG. 14 and expanded in the position shown in FIG. 18. By way of non-limiting example, the leaf spring 6 can have a thickness of between approximately 0.015" to approximately 0.030".

The spring 6 causes (and/or biases) the blade member 5 to move towards an intermediate position (see FIG. 16) and then to an expanded/second retracted (see FIG. 18) after the trigger button 3 is pressed into the lancet device LD (see FIGS. 17 and 19). In this way, once triggered, the lancet blade member 5 is caused to move automatically from the position shown in FIG. 14, to the position shown in FIG. 16 wherein the tip of the blade punctures/cuts-into the skin of a user, and finally to a position wherein the tip of the blade member 5 is caused to again retract into the lancet body (see FIG. 18). Throughout the movement, a center horizontal axis of the blade member 5 remains generally parallel to a center axis of the lancet body and/or to the ribs 1b, 1c, 1d, 2b, 2c and 2e. Of course, these movements occur in a fraction of a second.

In the embodiment shown in FIGS. 1-23, the lancet device is designed to be procured and/or purchased in a pre-loaded arrangement (see FIGS. 5, 6, 9, 14 and 15). In order to used the lancet device a single time, a user need only press the trigger button 3 to use it. Once triggered, however, the user will be unable to use the device again owing to the fact that this embodiment contains no mechanism for forcing or moving the blade member 5 from the position shown in FIG. 18 to the armed or retracted position shown in FIGS. 5, 6, 9, 14 and 15. Moreover, because the spring 6 maintains the blade member 5 in the position shown in FIG. 18, the lancet blade member 5, and particularly the tip portion 5a, is kept safely within the lancet body. Additionally, because the blade member 5 extends into the slot 3d of the trigger button 3, the user will be unable to use the device again also owing to the fact that this embodiment the blade member 5 prevents the trigger button 3 from moving back to the armed or retracted position shown in FIGS. 5, 6, 9, 14 and 15.

By way of non-limiting example, the armed position of the blade member 5, trigger button 3, and springs 4 and 6, shown in FIGS. 5, 6, 9, 14 and 15 can be set when the lancet device is manufactured and/or assembled, i.e., in a factory setting. FIGS. 9-11 and 14-19 thus show the various positions of the blade member 5, trigger button 3 and springs 4 and 6.

Figure 12:
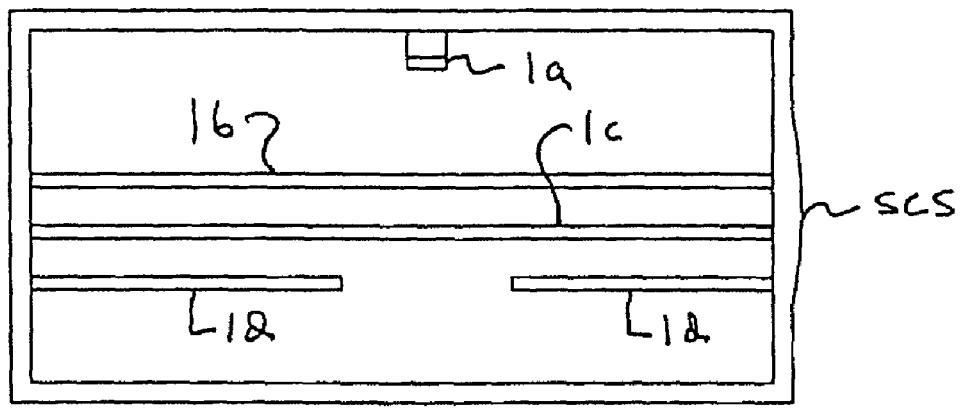
FIG. 12 shows an inside view of the rear cover portion of the embodiment shown in FIG. 1.

With reference to FIG. 12 it can be seen that the rear body part 1 can preferably be made as one-piece structure by e.g., injection molding. In this regard, it is preferably made of a plastic or synthetic resin such as, e.g., ABS plastic. The lower body part 1 may also be made of ABS-Metallic Silver and have a finish designated as SPI-A2. Of course, other materials and/or finishes may be utilized, without leaving the scope of the invention. Additionally, the lower body part 1 may have an overall length (measured horizontally across FIG. 12) that is between approximately 1.5" and approximately 3". Although undesirable for reasons of cost, the lower body part 1 may even be made of a plurality of sections of parts which are joined together to form the complete lower body part 1, without leaving the scope of the invention.

The lower body part 1 preferably has a front wall which includes a circular and/or curved center wall section/surface SCS. The lower body part 1 also preferably has a generally planar inner surface which extends between the generally straight side walls. This surface also extends from the rear wall to the front wall containing the surface SCS. The lower body part 1 additionally preferably includes four plate-like projections 1b, 1c and d which are generally centrally disposed relative to side walls. The purpose of these projections 1b, 1c and 1d is (with the aid of spaced-apart plate-like projections 2b, 2c and 2e) to help guide the blade member 5 along a generally linear path (see FIGS. 9-11). A centrally disposed L-shaped projecting wall 1a extends inwardly from the upper side wall of the lower body 1. As explained above, this wall 1a, together with wall 2a, retains/secures/traps the central portion 6a of the leaf spring 6 in the lancet device LD. In order to allow the blade member 5 to move freely and linearly (without also significant rocking) within the lancet device and without being obstructed by the ribs 1b, 1c and 1d and 2b, 2c and 2e, a spacing (see FIGS. 9-11) is provided between the ribs 1b, 1c and 1d and 2b, 2c and 2e. This spacing is preferably slightly larger/greater than a thickness of the blade member 5 to allow it to move freely and generally linearly within the lancet device LD.

Figure 13:
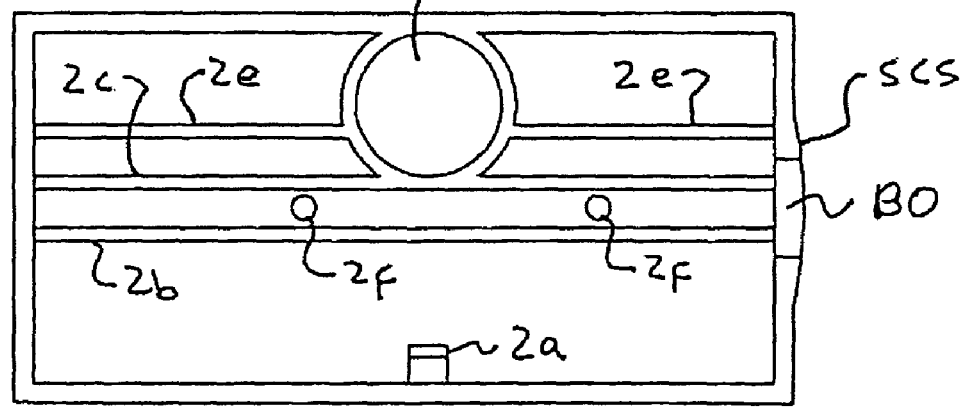
FIG. 13 shows an inside view of the front cover portion of the embodiment shown in FIG. 1.

FIG. 13 shows an inside view of the upper or front body part 2. As was the case with the lower body part 1, the upper body part 2 can preferably be made as one-piece structure by e.g., injection molding. In this regard, it is preferably made of a plastic or synthetic resin such as, e.g., ABS plastic. The upper body part 2 may also be made of ABS-Metallic Silver and have a finish designated as SPI-A2. Of course, other materials and/or finishes may be utilized, without leaving the scope of the invention. Additionally, the upper body part 2 may have an overall length that corresponds to the lower body part 1 and that is between approximately 1.5" and approximately 3" (i.e., between the front and rear walls). Although undesirable for economic reasons, the upper body part 2 may even be made of a plurality of sections of parts which are joined together to form the complete upper body part 2, without leaving the scope of the invention.

As was the case with the lower body part 1, the upper body part 2 preferably has a front straight wall which includes a circular and/or outwardly curved surface SCS. The radius of this surface SCS should correspond to the corresponding surface of the lower body part 1. Arranged on the front wall is a generally rectangular-shaped through opening/slot/groove BO. This opening BO is sized and configured to allow the tip 5a of the blade member 5 to pass there through. The body part 2 also includes a circular opening 2d which is sized to receive the cylindrical portion 3b of the trigger 3 (see FIG. 7). Of course, the opening 2d can have any desired size, shape or configuration provided it allows a user access to the trigger button 3 and provided that it generally corresponds to the size, shape and configuration of the trigger button 3. The opening 2d is formed in the bottom wall of the body part 2 and extends to the plate-like ribs 2e and 2c. The inner edge of the wall forming the opening 2d is also designed to be engaged and/or contacted by the surfaces 3f of the oppositely arranged projections 3e of the trigger button 3 when the trigger button 3 is in the position shown in FIGS. 5, 6, 9, 14 and 15.

The upper or front body part 2 additionally preferably includes four plate-like projections 2b, 2c and 2e which are generally centrally disposed relative to side walls. As explained above, the purpose of these projections 2b, 2c and 2e is (with the aid of spaced-apart plate-like projections 1b, 1c and 1d) to help guide the blade member 5 along a generally linear path (see FIGS. 9-11). A centrally disposed L-shaped projecting wall 2a extends inwardly from the upper side wall of the upper body 2. As explained above, this wall 2a, together with wall 1a, retains/secures/traps the central portion 6a of the leaf spring 6 in the lancet device LD. In order to allow the blade member 5 to move freely and linearly (without also significant rocking) within the lancet device and without being obstructed by the ribs 1b, 1c and 1d and 2b, 2c and 2e, a spacing (see FIGS. 9-11) is provided between the ribs 1b, 1c and 1d and 2b, 2c and 2e. This spacing is preferably slightly larger/greater than a thickness of the blade member 5 to allow it to move freely and generally linearly within the lancet device LD. Two generally cylindrical spaced-apart projections 2f also extend from the bottom wall of the body part 2. The projections 2f act to guide the movement of the blade member 5 within the lancet device LD by extending into and engaging with two spaced-apart cam slots/grooves/recesses 5d, 5e formed in the blade member 5.

As explained above, and as noted in FIGS. 14-19, the lancet device LD utilizes a cam system 5d, 5e and 2f to adjust the penetration depth of the lancet blade member 5. In the position shown in FIG. 14, it can be seen that the blade member 5 is positioned so that bottom edge of the cam slots 5d, 5e engage the projections 2f. However, in the position shown in FIG. 16, it can be seen that the blade member 5 is positioned and/or has moved to a position wherein the central curved portion of the cam slots 5d, 5e engage the projections 2f. Finally, in the position shown in FIG. 18, it can be seen that the blade member 5 is positioned and/or has moved to a position wherein the upper edge portion of the cam slots 5d, 5e engage the projections 2f. As the blade member 5 is guided by the interaction between the projections 2f and the cam slots 5d, 5e, it can be seen that the blade member 5 moves from an initial first retracted position (FIGS. 14-15) wherein the tip 5a of the blade member 5 is safely disposed with the lancet body to an intermediate position (FIGS. 16-17) wherein the tip 5a of the blade member 5 projects through the opening BO and past the surface SCS, and finally to a second retracted position (FIGS. 18-19) wherein the tip 5a of the blade member 5 is again safely disposed with the lancet body. Throughout this movement, which occurs in a fraction of a second under the action of the spring 6, the blade member 5 is kept from rocking and forced to move in a generally downward linear path by the projections 1b, 1c, 1d, 2b, 2c, and 2d, and while being guided by projections 2f and cam slots 5d, 5e.

Figure 9:
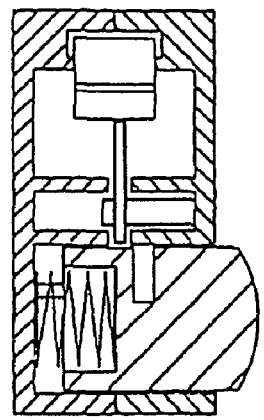
FIG. 9 shows a cross-section view through the arrows in FIG. 4 and illustrating the blade in a trigger-set/retracted position.
Figure 10:
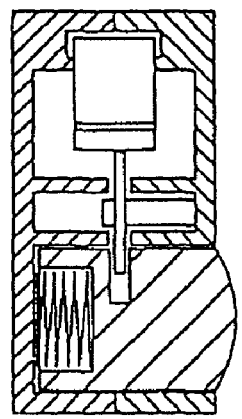
FIG. 10 shows a cross-section view through the arrows in FIG. 4 and illustrating the blade member in an intermediate position as it moves from the initial position shown in FIG. 9 to the final position shown in FIG. 11.
Figure 14:
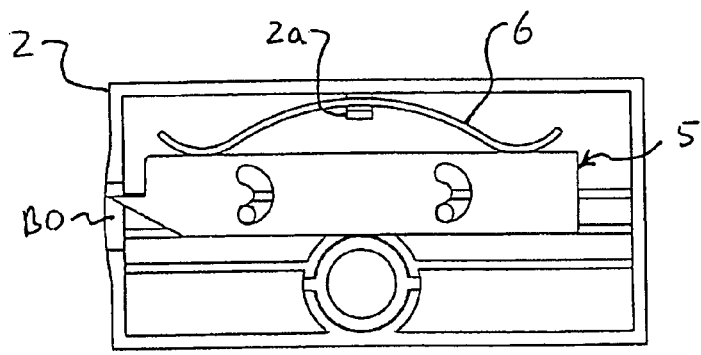
FIG. 14 shows the lancet device of FIG. 1 with the rear cover portion removed. The figure thus shows an inside view of the front cover portion of the embodiment shown in FIG. 1 with the spring member, blade member and trigger button positioned therein. The arrangement/position of the spring member, blade member and trigger button are in the position shown in FIG. 9.
Figure 15:
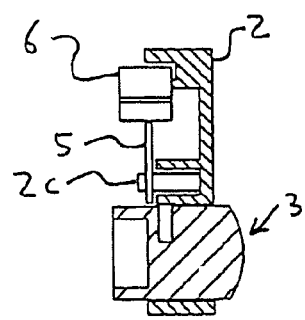
FIG. 15 shows a cross-section of FIG. 14.

The operation of the device shown in FIGS. 1-23 will now be explained with reference to FIGS. 9-11 and 14-19. FIGS. 9, 14 and 15 shows the lancet device LD with the blade member 5 in the loaded position, i.e., ready to move to an extended and second retracted position when the trigger button 3 is pressed. The blade member 5 retains the loaded position of FIGS. 9, 14 and 15 as a result of engagement between the bottom surface 5f of the blade member 5 with the cylindrical surface 3b of the trigger button 3. On the other hand, FIGS. 10, 16 and 17 shows what initially happens when the trigger button 3 is pressed, i.e., the trigger button 3 is caused to move/slide inwardly against the biasing force of the spring 4, which becomes compressed. As soon as the trigger button 3 moves to a position wherein the slot 3d is positioned below the edge 5f of the blade member 5, the biasing force of the spring 6 causes the blade member to move downwards and into the slot 3d in a fraction of a second. However, because this movement is controlled by guiding engagement between the projections 2f and cam recesses 5d and 5e, the blade member 5 also simultaneously moves horizontally. The combined downward/horizontal movement has the shape of a curved path (see FIGS. 103-104). Thus, when the blade member 5 is released from the loaded position of FIGS. 9, 14 and 15, it is caused to move along the curved path dictated by the guiding system 2f, 5d and 5e. This occurs because the trigger button 3 allows the blade member 5 to enter the slot 3d. As discussed above, this movement is caused by the expansion (in the downward direction) of the spring 6. The blade member 5 thus moves towards and past the surface SCS and then back again until the projections 2f contact or engage the inner edges of the cam slots 5d and 5e and/or until the surface 5f of the blade member 5 engages with the surface 3g of the slot 3d. Once the trigger button 3 is released (once a user stops pressing on the trigger 3), the trigger button 3 is automatically prevented from moving back to the armed state shown in FIGS. 9, 14 and 15. Thus, unlike known prior art devices, the lancet device contains no mechanism for reloading and/or moving the blade member 5 and/or trigger button 3 back into the position shown in FIGS. 9, 14 and 15, i.e., the lancet device LD cannot then be placed back into the position shown in FIG. 9 because the device contains no mechanism for placing the surface 5f back into engagement with the surface 3b. Indeed, the spring 4, by being arranged/trapped between an inner surface of the body and the trigger button 3, and by virtue of the blade member 5 entering the slot 3d, maintains a compressed state shown in FIG. 11, while the spring 6 maintains an expanded state. This ensures that the blade member 5 cannot be re-armed, and ensures that the blade member 5 (along with the tip portion 5a) is safely retained within the body after a one-time use.

FIGS. 24-45 show a second non-limiting embodiment of a single-use and/or disposable blade lancet device LD. Lancet device LD has a lancet body made up of an upper or front body portion 20 and a lower or rear body portion 10. These parts 10 and 20 are connected to each other, e.g., using adhesives and/or fasteners and/or welding and/or snap-together holding mechanisms (not shown), when the lancet device LD is initially assembled. A blade member 50 is movably disposed within the body parts 10, 20 (see FIGS. 31-33). Although not shown, a front end cover can also be removably connected or attached to a front portion of the body parts 10, 20 as is exemplified in the embodiment described in copending U.S. patent application Ser. No. 10/441,065 filed on May 20, 2003, the entire disclosure of which is hereby expressly incorporated by reference in its entirety.

As with many lancet devices, the lancet device defines a plane or surface SCS which is configured to contact (i.e., be positioned against) a user's skin. However, unlike known lancet devices, the instant embodiment may utilize an outwardly curved skin engaging surface SCS beyond which the tip portion 50a of the lancet blade member 50 can extend and/or project. Of course, the invention also contemplates using a planar front skin engaging surface SCS, e.g., of the type described in U.S. Pat. No. 6,258,112, the disclosure of which is hereby expressly incorporated by reference in its entirety.

As can be seen in FIGS. 24-27, the lancet body can have a generally rectangular shape and can preferably also have an ergonomic shape to facilitate comfortable gripping/holding. Of course, as was the case with the first embodiment, the invention contemplates other shapes provided that they result in a relatively inexpensive design and/or which is economical to produce. As explained above, the front end of the lancet device includes an outwardly curved skin engaging surface SCS which is defined by outer front outwardly curved surfaces of both cover parts 10, 20. A lancet blade opening BO extends through one or both of the front walls F of the cover parts 10, 20 and serves to allow the lancet blade member 50 to penetrate beyond the surface SCS (see FIG. 36). As with the first embodiment, a trigger button 30 is movably mounted to the lancet body. In the instant embodiment, the trigger button 30 is circularly/cylindrically-shaped for reasons of aesthetic design. However, the invention contemplates other shapes for the trigger button 30 such as, e.g., oval, triangular, square, polygonal, etc. In the instant embodiment, the trigger button 30 is generally centrally mounted, relative to walls F and R, to a lower area of the front cover 20. However, the invention contemplates other locations and/or positions for the trigger button 30, provided such locations allow the lancet device to function properly. The trigger button 30 is seated in a trigger opening 20d formed in the front cover 20 and is sized to slide within the opening 20d in a smooth low-friction manner. The trigger button 30 has a finger engaging (e.g. push button) portion 30a (just as was the case in the trigger button 3 shown in FIGS. 8a-8c) that can be pushed into the lancet body (see FIGS. 31-33). The trigger button 30 is biased towards an extended position (see FIG. 31) via a coil compression spring 40. This biasing force can be overcome, of course, when the trigger button 30 is pushed into the lancet body (see FIGS. 32 and 33) by applying a force to the finger engaging portion 30a. However, because the trigger button 30 includes a slot 30d, once the blade member 50 enters the slot 30d (see FIGS. 32 and 33), and engages the bottom surface 30g of the slot 30d under the biasing force of the leaf spring 60, the trigger button 30 is prevented from moving back by the blade member 50 under the action of the spring 40 to the position shown in FIG. 31. Thus, once triggered, the lancet device is automatically rendered unusable again—thereby rendering the device a single-use device.

Although not shown, the lancet body can preferably includes a viewing opening or be made of a transparent/translucent material so that the user will easily note that the device is properly set and/or has not be used. The opening or window can be formed in the front cover 20 and can be arranged in a convenient area which allows the user to see the position of the blade member 50. The opening or window, of course, can have any desired shape or configuration and can be located at any desired location provided that the user is able to discern the setting position of the blade member 50.

The trigger button 30 can have the same configuration as was the case with the trigger button 3 shown in FIGS. 8a-8c and was used in the first embodiment. Thus, the trigger button 30 can preferably be made as one-piece structure by e.g., injection molding. In this regard, it is preferably made of a plastic or synthetic resin such as, e.g., ABS plastic. The trigger button 30 may also be made of ABS-Red and have a finish designated as SPI-A2. Of course, other materials and/or finishes may be utilized, without leaving the scope of the invention. Additionally, by way of non-limiting example, the trigger button 30 may have an overall length that is approximately ½" (i.e., measured horizontally across FIG. 30). Moreover, the trigger button 30 may even be made of a plurality of sections of parts which are joined together to form the complete trigger button 30, without leaving the scope of the invention, although it is preferred that it be formed a one-piece member. It would be even more preferable if the trigger button 30 were integrally formed with the lancet body, and in particular, integrally formed with the upper body part 20 and connected thereto with a living hinge (not shown).

With reference to FIGS. 44 and 45, the lancet blade member 50 can be a stainless steel member whose tip portion 50a is shaped with an angled sharpened edge 50b. The blade member 50 also includes a front edge portion 50c and a generally rectangular-shaped body portion. Two spaced-apart cylindrical projections 50d and 50e can be secured/connected/fixed to the body portion via, e.g., press fit, welding, or a bonded connection. As will be described later on, these projections 50d and 50e are sized to slidingly engage two arc-shaped cam grooves 20f (see FIG. 41). Alternatively, the blade member 50 can be of a multi-piece structure (see e.g., FIGS. 100-102) in which a stainless steel tip portion is mounted to a body portion which can be made of, e.g., synthetic resin or polymer material. By way of non-limiting example, the blade member 50 can have a thickness of between approximately 0.010" to approximately 0.050".

Figure 28:
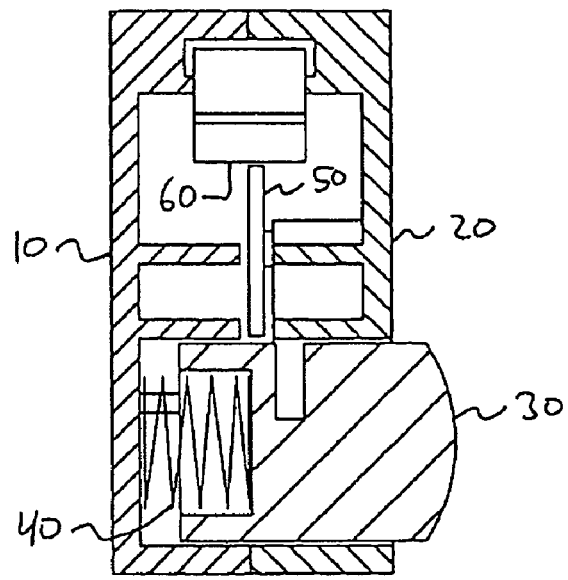
FIG. 28 shows a cross-section view through the arrows in FIG. 27.
Figure 29:
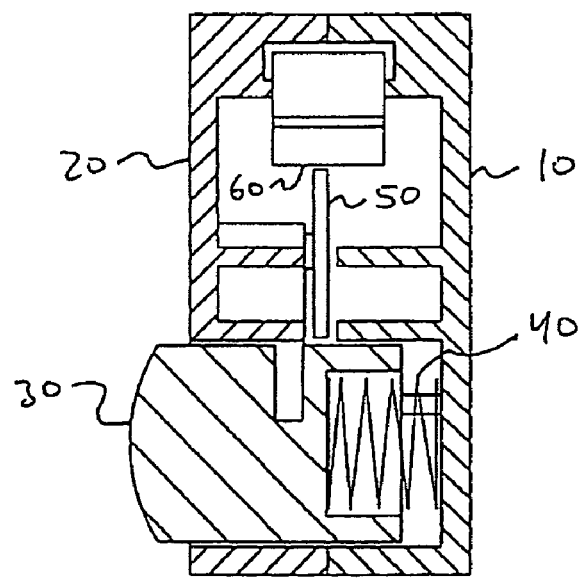
FIG. 29 shows a cross-section view through the arrows in FIG. 25.
Figure 30:
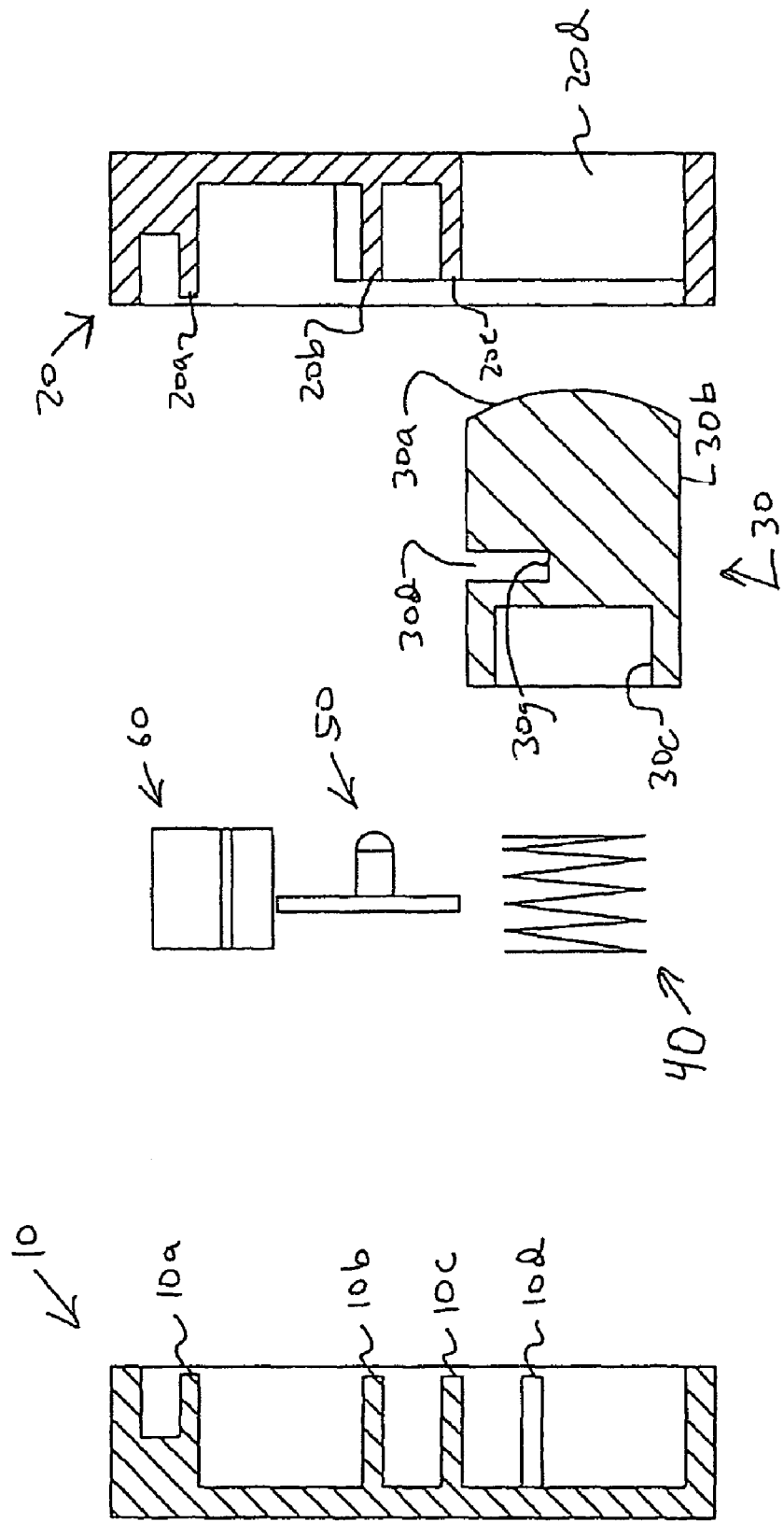
FIG. 30 shows the cross-section of FIG. 28 in a dis-assembled arrangement.

As can be seen in FIGS. 28-30, the lancet device LD uses a coil compression spring 40 mounted therein. In this regard, the spring 40, which can be made of spring steel and which can have the form of a helical coil spring, is arranged between an inner wall of the rear cover 10 and extends into an opening 30c of the trigger button 30. This spring 40 causes (and/or biases) the trigger button 30 to move towards an extended position, i.e., an initial prior-use position before the trigger 30 is activated. As discussed above, the trigger button 30 includes a cylindrical 30b portion that slides within the opening 20d of the lancet body and is mounted to the upper or front body part 20. The spring 40 can be of the same type and configuration as was used in the first embodiment.

Figure 32:
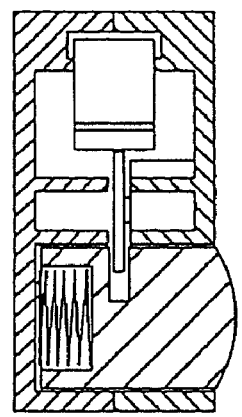
FIG. 32 shows a cross-section view through the arrows in FIG. 27 and illustrating the blade member in an intermediate position as it moves from the initial position shown in FIG. 31 to the final position shown in FIG. 33.
Figure 33:
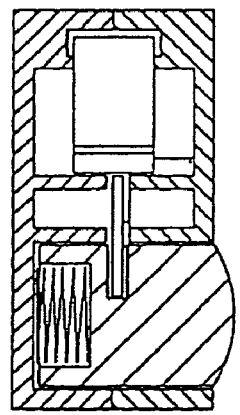
FIG. 33 shows a cross-section view through the arrows in FIG. 27 and illustrating the blade member in triggered/expanded position.

As noted above, the leaf spring 60, which can be a stamped spring steel member, is utilized to bias and/or move the blade member 50 from an initial retracted/pre-use position (see FIGS. 28, 29, 31, 34 and 35) to an extended/second retracted position (see FIGS. 33, 38 and 39). The spring 60 has a central curved portion 60a (see FIG. 42) which is secured to the lancet body between opposing grooves formed by L-shaped projecting portions 10a and 20a (see FIG. 30) and two generally symmetrical curved end portions 60b and 60c (see FIG. 42) which contact and/or engage the blade member 50 (see FIGS. 31-39). The leaf spring 60 is thus compressed in the position shown in FIGS. 31 and 34 and expanded in the position shown in FIGS. 33 and 38. By way of non-limiting example, the leaf spring 60 can have a thickness of between approximately 0.015" to approximately 0.030".

The spring 60 causes (and/or biases) the blade member 50 to move towards an intermediate position (see FIG. 36) and then to an expanded/second retracted (see FIG. 38) after the trigger button 30 is pressed into the lancet device LD (see FIGS. 37 and 39). In this way, once triggered, the lancet blade member 50 is caused to move automatically from the position shown in FIG. 34, to the position shown in FIG. 36 wherein the tip of the blade punctures/cuts-into the skin of a user, and finally to a position wherein the tip of the blade member 50 is caused to again retract into the lancet body (see FIG. 38). Throughout the movement, a center horizontal axis of the blade member 50 remains generally parallel to a center axis of the lancet body and/or to the ribs 10*b*, 10*c*, 10*d*, 20*b*, 20*c* and 20*e*. Of course, these movements occur in a fraction of a second.

In the embodiment shown in FIGS. 24-45, the lancet device is designed to be procured and/or purchased in a pre-loaded arrangement (see FIGS. 28, 29, 31, 34 and 35). In order to used the lancet device a single time, a user need only press the trigger button 30 to use it. Once triggered, however, the user will be unable to use the device again owing to the fact that this embodiment contains no mechanism for forcing or moving the blade member 50 from the position shown in FIG. 38 to the armed or retracted position shown in FIGS. 28, 29, 31, 34 and 35. Moreover, because the spring 60 maintains the blade member 50 in the position shown in FIG. 38, the lancet blade member 50, and particularly the tip portion 50*a*, is kept safely within the lancet body. Additionally, because the blade member 50 extends into the slot 30*d* of the trigger button 30, the user will be unable to use the device again also owing to the fact that this embodiment the blade member 50 prevents the trigger button 30 from moving back to the armed or retracted position shown in FIGS. 28, 29, 31, 34 and 35.

By way of non-limiting example, the armed position of the blade member 50, trigger button 30, and springs 40 and 60, shown in FIGS. 28, 29, 31, 34 and 35 can be set when the lancet device is manufactured and/or assembled, i.e., in a factory setting. FIGS. 31-33 and 34-39 thus show the various positions of the blade member 50, trigger button 30 and springs 40 and 60.

With reference to FIG. 40 it can be seen that the rear body part 10 can preferably be made as one-piece structure by e.g., injection molding. In this regard, it is preferably made of a plastic or synthetic resin such as, e.g., ABS plastic. The lower body part 10 may also be made of ABS-Metallic Silver and have a finish designated as SPI-A2. Of course, other materials and/or finishes may be utilized, without leaving the scope of the invention. Additionally, the lower body part 10 may have an overall length (measured horizontally across FIG. 40) that is between approximately 1.5" and approximately 3". Although undesirable for reasons of cost, the lower body part 10 may even be made of a plurality of sections of parts which are joined together to form the complete lower body part 10, without leaving the scope of the invention.

The lower body part 10 preferably has a front wall which includes a circular and/or curved center wall section/surface SCS. The lower body part 10 also preferably has a generally planar inner surface which extends between the generally straight side walls. This surface also extends from the rear wall to the front wall containing the surface SCS. The lower body part 10 additionally preferably includes four plate-like projections 10*b*, 10*c* and 10*d* which are generally centrally disposed relative to side walls. The purpose of these projections 10*b*, 10*c* and 10*d* is (with the aid of spaced-apart plate-like projections 20*b*, 20*c* and 20*e*) to help guide the blade member 50 along a generally linear path (see FIGS. 31-33). A centrally disposed L-shaped projecting wall 10*a* extends inwardly from the upper side wall of the lower body 10. As explained above, this wall 10*a*, together with wall 20*a*, retains/secures/traps the central portion 60*a* of the leaf spring 60 in the lancet device LD. In order to allow the blade member 50 to move freely and linearly (without also significant rocking) within the lancet device and without being obstructed by the ribs 10*b*, 10*c* and 10*d* and 20*b*, 20*c* and 20*e*, a spacing (see FIGS. 31-33) is provided between the ribs 10*b*, 10*c* and 10*d* and 20*b*, 20*c* and 20*e*. This spacing is preferably slightly larger/greater than a thickness of the blade member 50 to allow it to move freely and generally linearly within the lancet device LD.

FIG. 41 shows an inside view of the upper or front body part 20. As was the case with the lower body part 10, the upper body part 20 can preferably be made as one-piece structure by e.g., injection molding. In this regard, it is preferably made of a plastic or synthetic resin such as, e.g., ABS plastic. The upper body part 20 may also be made of ABS-Metallic Silver and have a finish designated as SPI-A2. Of course, other materials and/or finishes may be utilized, without leaving the scope of the invention. Additionally, the upper body part 20 may have an overall length that corresponds to the lower body part 10 and that is between approximately 1.5" and approximately 3" (i.e., between the front and rear walls). Although undesirable for economic reasons, the upper body part 20 may even be made of a plurality of sections of parts which are joined together to form the complete upper body part 20, without leaving the scope of the invention.

As was the case with the lower body part 10, the upper body part 20 preferably has a front straight wall which includes a circular and/or outwardly curved surface SCS. The radius of this surface SCS should correspond to the corresponding surface of the lower body part 10. Arranged on the front wall is a generally rectangular-shaped through opening/slot/groove BO. This opening BO is sized and configured to allow the tip 50*a* of the blade member 50 to pass there through. The body part 20 also includes a circular opening 20*d* which is sized to receive the cylindrical portion 30*b* of the trigger 30 (see FIG. 30). Of course, the opening 20*d* can have any desired size, shape or configuration provided it allows a user access to the trigger button 30 and provided that it generally corresponds to the size, shape and configuration of the trigger button 30. The opening 20*d* is formed in the bottom wall of the body part 20 and extends to the plate-like ribs 20*e* and 20*c*. The inner edge of the wall forming the opening 20*d* is also designed to be engaged and/or contacted by the surfaces (similar to surfaces 3*f* of FIG. 8*b*) of the oppositely arranged projections (similar to projections 3*e* of FIG. 8*a-c*) of the trigger button 30 when the trigger button 30 is in the position shown in FIGS. 28, 29, 31, 34 and 35.

The upper or front body part 20 additionally preferably includes four plate-like projections 20*b*, 20*c* and 20*e* which are generally centrally disposed relative to side walls. As explained above, the purpose of these projections 20*b*, 20*c* and 20*e* is (with the aid of spaced-apart plate-like projections 10*b*, 10*c* and 10*d*) to help guide the blade member 50 along a generally linear path (see FIGS. 31-33). A centrally disposed L-shaped projecting wall 20*a* extends inwardly from the upper side wall of the upper body 20. As explained above, this projecting wall 20*a*, together with projecting wall 10*a*, retains/secures/traps the central portion 60*a* of the leaf spring 60 in the lancet device LD. In order to allow the blade member 50 to move freely and linearly (without also significant rocking) within the lancet device and without being obstructed by the ribs 10*b*, 10*c* and 10*d* and 20*b*, 20*c* and 20*e*, a spacing (see FIGS. 31-33) is provided between the ribs 10*b*, 10*c* and 10*d* and 20*b*, 20*c* and 20*e*. This spacing is preferably slightly larger/greater than a thickness of the blade member 50 to allow it to move freely and generally linearly within the lancet device LD. Two generally arc-shaped cam grooves 20*f* also extend from the bottom wall of the body part 20. The grooves 20*f* act to guide the movement of the blade member 50 within the lancet device LD by receiving therein and engaging with two spaced-apart projections 50*d*, 50*e* arranged on the blade member 50.

As explained above, and as noted in FIGS. 34-39, the lancet device LD utilizes a cam system 50d, 50e and 20f to adjust the penetration depth of the lancet blade member 50. In the position shown in FIG. 34, it can be envisioned that the blade member 50 is positioned so that upper edges of the cam grooves 20f engage the projections 50d, 50e. However, in the position shown in FIG. 36, it should be apparent that the blade member 50 is positioned and/or has moved to a position wherein the central curved portion of the cam grooves 20f engage the projections 50d, 50e. Finally, in the position shown in FIG. 38, it can be seen that the blade member 50 is positioned and/or has moved to a position wherein the lower edge portion of the cam grooves 20f engage the projections 50d, 50e. As the blade member 50 is guided by the interaction between the projections 50d, 50e and the cam grooves 20f, it can be acknowledged that the blade member 50 moves from an initial first retracted position (FIGS. 34-35) wherein the tip 50a of the blade member 50 is safely disposed with the lancet body to an intermediate position (FIGS. 36-37) wherein the tip 50a of the blade member 50 projects through the opening BO and past the surface SCS, and finally to a second retracted position (FIGS. 38-39) wherein the tip 50a of the blade member 50 is again safely disposed with the lancet body. Throughout this movement, which occurs in a fraction of a second under the action of the spring 60, the blade member 50 is kept from rocking and forced to move in a generally downward curva-linear path by the projections 10b, 10c, 10d, 20b, 20c, and 20d, and while being guided by projections 50d, 50e and cam grooves 20f.

Figure 31:
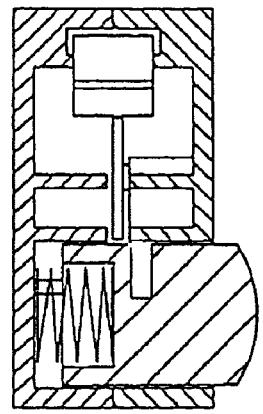
FIG. 31 shows a cross-section view through the arrows in FIG. 27 and illustrating the blade in a trigger-set/retracted position.

The operation of the device shown in FIGS. 24-45 will now be explained with reference to FIGS. 31-33 and 34-39. FIGS. 31, 34 and 35 shows the lancet device LD with the blade member 50 in the loaded position, i.e., ready to move to an extended and second retracted position when the trigger button 30 is pressed. The blade member 50 retains the loaded position of FIGS. 31, 34 and 35 as a result of engagement between the bottom surface 50f of the blade member 50 with the cylindrical surface 30b of the trigger button 30. On the other hand, FIGS. 32, 36 and 37 shows what initially happens when the trigger button 30 is pressed, i.e., the trigger button 30 is caused to move/slide inwardly against the biasing force of the spring 40, which becomes compressed. As soon as the trigger button 30 moves to a position wherein the slot 30d is positioned below the edge 50f of the blade member 50, the biasing force of the spring 60 causes the blade member 50 to move downwards and into the slot 30d in a fraction of a second. However, because this movement is controlled by guiding engagement between the projections 50d, 50e and cam grooves 20f, the blade member 5 also simultaneously moves in a curva-linear horizontal direction. The combined downward/horizontal movement has the shape of a curved path (see FIGS. 103-104). Thus, when the blade member 50 is released from the loaded position of FIGS. 31, 34 and 35, it is caused to move along the curved path dictated by the guiding system 20f, 50d and 50e. This occurs because the trigger button 30 allows the blade member 50 to enter the slot 30d. As discussed above, this movement is caused by the expansion (in the downward direction) of the spring 60. The blade member 50 thus moves towards and past the surface SCS and then back again until the projections 50d, 50e contact or engage the inner edges of the cam grooves 20f and/or until the surface 50f of the blade member 50 engages with the surface 30g of the slot 30d. Once the trigger button 30 is released (once a user stops pressing on the trigger 3), the trigger button 30 is automatically prevented from moving back to the armed state shown in FIGS. 31, 34 and 35. Thus, unlike known prior art devices, the lancet device contains no mechanism for reloading and/or moving the blade member 50 and/or trigger button 30 back into the position shown in FIGS. 31, 34 and 35, i.e., the lancet device LD cannot then be placed back into the position shown in FIG. 31 because the device contains no mechanism for placing the surface 50f back into engagement with the surface 30b. Indeed, the spring 40, by being arranged/trapped between an inner surface of the body and the trigger button 30, and by virtue of the blade member 50 entering the slot 3d, maintains a compressed state shown in FIG. 33, while the spring 60 maintains an expanded state. This ensures that the blade member 50 cannot be re-armed, and ensures that the blade member 50 (along with the tip portion 50a) is safely retained within the body after a one-time use of the lancet device LD.

FIGS. 46-50 show a front and side views of another embodiment of the single-use blade lancet device, as well as a view with the rear cover portion removed. The body is similar to that of the embodiment shown in FIGS. 1-23 except that the front portion of the device uses angled/tapered surfaces which extend between the front wall and the side walls. The internal parts of the device shown in FIGS. 1-23 can thus be used in this more ergonomic body. With some require internal modifications, this external body shape can also be used in any of the embodiments disclosed herein in order to provide for a more ergonomic shape and/or so that a user can more easily determine which end to place against the surface of the skin.

FIGS. 51-55 show another embodiment of a lancet device. The device is similar to that of FIGS. 1-23 except that the rear and front covers 1 and 2 are replaced by rear and front covers 100 and 200 which are similar that the rear and front covers 1 and 2, but which do not utilize/include the L-shaped projections 1a and 2a. The remaining parts which similar to that of FIGS. 1-23 use corresponding reference numbers. This embodiment also differs from the embodiment shown in FIGS. 1-23 in that the leaf spring 6 is replaced by a system of sliding wedges 8a, 8a and oppositely arranged compression springs 7a and 7b. As is evident from the figures, the two horizontally oriented coil springs and two horizontally movable sliding wedges cause the blade member 5 to move in generally the same curva-linear manner as the leaf spring 6 of the embodiment shown in FIGS. 1-23. The upper wedge 8b has an upper planar surface which engages an inside surface of the wall of the lancet body whereas the lower wedge 8a has a lower planar surface which engages an upper edge of the blade member 5. The wedges 8a, 8b also have angled/tapered surfaces which slidingly engage each other. These surfaces may be smooth so that to minimize sliding friction. FIG. 51 shows the device in the armed position and FIG. 52 shows the spring members 7a, 7b, blade member 5 and trigger button 3 being the fully triggered/expanded position. FIG. 54 shows an inside view of the rear cover portion 100 of the embodiment shown in FIG. 51 and FIG. 55 shows an inside view of the front cover portion 200 of the embodiment shown in FIG. 51. The springs 7a, 7b can be of the same material as spring 4 and the wedges 8a, 8b can be made of, e.g., synthetic resin and can be made of the same material as the body portions 100, 200 or trigger button 3. Of course, the invention contemplates using this biasing arrangement 7a-b, 8a-b in the device shown in FIGS. 23-45 with similar modifications to the lancet body parts 10, 20.

The operation of the device shown in FIGS. 51-55 will now be explained with reference to FIGS. 51-53. FIGS. 51 and 53 shows the lancet device LD with the blade member 5 in the loaded position, i.e., ready to move to an extended and second retracted position (see FIG. 52) when the trigger button 3 is pressed. The blade member 5 retains the loaded position of FIGS. 51 and 53 as a result of engagement between the bottom surface 5f of the blade member 5 with the cylindrical surface 3b of the trigger button 3. On the other hand, e.g., FIGS. 10, 16 and 17 shows what initially happens when the trigger button 3 is pressed, i.e., the trigger button 3 is caused to move/slide inwardly against the biasing force of the spring 4, which becomes compressed. As soon as the trigger button 3 moves to a position wherein the slot 3d is positioned below the edge 5f of the blade member 5, the biasing force of the biasing system 7a-b and 8a-b causes the blade member 5 to move downwards and into the slot 3d in a fraction of a second. However, because this movement is controlled by guiding engagement between the projections 200f and cam recesses 5d and 5e, the blade member 5 also simultaneously moves horizontally. The combined downward/horizontal movement has the shape of a curved path (see FIGS. 103-104). Thus, when the blade member 5 is released from the loaded position of FIGS. 51 and 53, it is caused to move along the curved path dictated by the guiding system 200f, 5d and 5e. This occurs because the trigger button 3 allows the blade member 5 to enter the slot 3d. As discussed above, this movement is caused by the expansion (in the downward direction) of the biasing system 7a-b and 8a-b. The blade member 5 thus moves towards and past the surface SCS and then back again until the projections 200f contact or engage the inner edges of the cam slots 5d and 5e and/or until the surface 5f of the blade member 5 engages with the surface 3g of the slot 3d. Once the trigger button 3 is released (once a user stops pressing on the trigger 3), the trigger button 3 is automatically prevented from moving back to the armed state shown in FIGS. 51 and 53 in the same way that was described with regard to the embodiment shown in FIGS. 1-23. Thus, unlike known prior art devices, the lancet device contains no mechanism for reloading and/or moving the blade member 5 and/or trigger button 3 back into the position shown in FIGS. 51 and 53, i.e., the lancet device LD cannot then be placed back into the position shown in FIG. 51 because the device contains no mechanism for placing the surface 5f back into engagement with the surface 3b. Indeed, the spring 4, by being arranged/trapped between an inner surface of the body and the trigger button 3, and by virtue of the blade member 5 entering the slot 3d, maintains a compressed state shown in FIG. 11, while the biasing system 7a-b and 8a-b maintains an expanded state shown in FIG. 52. This ensures that the blade member 5 cannot be re-aimed, and ensures that the blade member 5 (along with the tip portion 5a) is safely retained within the body after a one-time use.

FIGS. 56-60 show another embodiment of a lancet device. The device is similar to that of FIGS. 1-23 except that the rear and front covers 1 and 2 are replaced by rear and front covers 100 and 200 which are similar that the rear and front covers 1 and 2, but which do not utilize/include the L-shaped projections 1a and 2a. The remaining parts which similar to that of FIGS. 1-23 use corresponding reference numbers. This embodiment also differs from the embodiment shown in FIGS. 1-23 in that the leaf spring 6 is replaced by a system of springs 600a and 600b which are maintained in position by upper extending projecting portions of the blade member 500. As is evident from the figures, the two vertically oriented coil springs cause the blade member 500 to move in generally the same curva-linear manner as the leaf spring 6 of the embodiment of FIGS. 1-23. Each spring 600a and 600b is arranged between an inside surface of the wall of the lancet body and slides over one of the upwardly extending projecting portions of the blade member 500. FIG. 56 shows the device in the armed position and FIG. 57 shows the springs 600a, 600b, blade member 500 and trigger button 3 being the fully triggered/expanded position. FIG. 59 shows an inside view of the rear cover portion 100 of the embodiment shown in FIG. 56 and FIG. 60 shows an inside view of the front cover portion 200 of the embodiment shown in FIG. 56. The springs 600a, 600b can be of the same material as spring 4. Of course, the invention also contemplates using this biasing arrangement 600a, 600b in the device shown in FIGS. 23-45 with similar modifications to the lancet body parts 10, 20.

The operation of the device shown in FIGS. 56-60 will now be explained with reference to FIGS. 56-58. FIGS. 56 and 58 shows the lancet device LD with the blade member 500 in the loaded position, i.e., ready to move to an extended and second retracted position (see FIG. 57) when the trigger button 3 is pressed. The blade member 500 retains the loaded position of FIGS. 56 and 58 as a result of engagement between the bottom surface 500f of the blade member 500 with the cylindrical surface 3b of the trigger button 3. On the other hand, e.g., FIGS. 10, 16 and 17 shows what initially happens when the trigger button 3 is pressed, i.e., the trigger button 3 is caused to move/slide inwardly against the biasing force of the spring 4, which becomes compressed. As soon as the trigger button 3 moves to a position wherein the slot 3d is positioned below the edge 500f of the blade member 500, the biasing force of the biasing system 600a, 600b causes the blade member 500 to move downwards and into the slot 3d in a fraction of a second. However, because this movement is controlled by guiding engagement between the projections 200f and cam recesses 500d and 500e, the blade member 500 also simultaneously moves horizontally. The combined downward/horizontal movement has the shape of a curved path (see FIGS. 103-104). Thus, when the blade member 500 is released from the loaded position of FIGS. 56 and 58, it is caused to move along the curved path dictated by the guiding system 200f, 500d and 500e. This occurs because the trigger button 3 allows the blade member 500 to enter the slot 3d. As discussed above, this movement is caused by the expansion (in the downward direction) of the biasing system 600a, 600b. The blade member 500 thus moves towards and past the surface SCS and then back again until the projections 200f contact or engage the inner edges of the cam slots 500d and 500e and/or until the surface 500f of the blade member 500 engages with the surface 3g of the slot 3d. Once the trigger button 3 is released (once a user stops pressing on the trigger 3), the trigger button 3 is automatically prevented from moving back to the armed state shown in FIGS. 56 and 58 in the same way that was described with regard to the embodiment shown in FIGS. 1-23. Thus, unlike known prior art devices, the lancet device contains no mechanism for reloading and/or moving the blade member 500 and/or trigger button 3 back into the position shown in FIGS. 56 and 58, i.e., the lancet device LD cannot then be placed back into the position shown in FIG. 56 because the device contains no mechanism for placing the surface 500f back into engagement with the surface 3b. Indeed, the spring 4, by being arranged/trapped between an inner surface of the body and the trigger button 3, and by virtue of the blade member 500 entering the slot 3d, maintains a compressed state shown in FIG. 11, while the biasing system 600a, 600b maintains an expanded state shown in FIG. 57. This ensures that the blade member 500 cannot be re-armed, and ensures that the blade member 500 (along with the tip portion 500a) is safely retained within the body after a one-time use.

FIGS. 61-74 show another embodiment of a lancet device. The device is similar to that of FIGS. 1-23 except that it additionally utilizes a removable locking device 9. The locking device 9 is used to lock the blade member 5 in the trigger-set/retracted position so that the device cannot be unintentionally triggered. The rear and front covers 1 and 2 are replaced by rear and front covers 1000 and 2000 which are similar that the rear and front covers 1 and 2, except that rear cover 1000 additionally includes two through openings PO which are sized to receive therein the two pin portions 9c, 9d of the locking device 9. The remaining parts which similar to that of FIGS. 1-23 use corresponding reference numbers. FIGS. 63-67, 68 and 74 show the device in the armed position and FIGS. 62 and 74 shows the locking device 9 removed from the lancet device and ready for use. FIG. 68 shows an inside view of the rear cover portion 1000 of the embodiment shown in FIGS. 61-67 and FIG. 69 shows an inside view of the front cover portion 2000 of the embodiment shown in FIGS. 61-67. The locking device can be a one-piece member and can be made of the same material as the trigger 3. As can be seen in FIGS. 70-73, the locking device 9 includes a tab portion or gripping portion 9a which can be centrally disposed on a flange portion 9b. Two generally cylindrical projecting pins 9c, 9d extend from an opposite side of the flange portion 9b. The flange 9b can have a generally rectangular shape. Of course, the invention contemplates using the locking device 9 in any of the other embodiments disclosed in this application.

The operation of the device shown in FIGS. 61-74 will now be explained. FIGS. 65 and 67 shows the lancet device LD with the blade member 5 in the loaded position, i.e., ready to move to an extended and second retracted position when the trigger button 3 is pressed. The blade member 5 retains the loaded position of FIGS. 65 and 67 as a result of engagement between the bottom surface 5f of the blade member 5 with the cylindrical surface 3b of the trigger button 3 and/or because the pin portions 9c and 9c engage with the arc-shaped recesses 5d, 5e of the blade member 5. On the other hand, e.g., FIGS. 62 and 74 shows how the locking device can be removed from the lancet device LD. Thereafter, when the trigger button 3 is pressed, i.e., the trigger button 3 is caused to move/slide inwardly against the biasing force of the spring 4, which becomes compressed. As soon as the trigger button 3 moves to a position wherein the slot 3d is positioned below the edge 5f of the blade member 5, the biasing force of the biasing member 6 causes the blade member 5 to move downwards and into the slot 3d in a fraction of a second. However, because this movement is controlled by guiding engagement between the projections 2000f and cam recesses 5d and 5e, the blade member 5 also simultaneously moves horizontally. The combined downward/horizontal movement has the shape of a curved path (see FIGS. 103-104). Thus, when the blade member 5 is released from the loaded position of FIGS. 69 and 74, it is caused to move along the curved path dictated by the guiding system 2000f, 5d and 5e. This occurs because the trigger button 3 allows the blade member 5 to enter the slot 3d. As discussed above, this movement is caused by the expansion (in the downward direction) of the biasing member 6b. The blade member 5 thus moves towards and past the surface SCS and then back again until the projections 2000f contact or engage the inner edges of the cam slots 5d and 5e and/or until the surface 5f of the blade member 5 engages with the surface 3g of the slot 3d. Once the trigger button 3 is released (once a user stops pressing on the trigger 3), the trigger button 3 is automatically prevented from moving back to the armed state shown in FIG. 69 in the same way that was described with regard to the embodiment shown in FIGS. 1-23. Thus, unlike known prior art devices, the lancet device contains no mechanism for reloading and/or moving the blade member 5 and/or trigger button 3 back into the position shown in FIG. 69, i.e., the lancet device LD cannot then be placed back into the position shown in FIG. 69 because the device contains no mechanism for placing the surface 5f back into engagement with the surface 3b. Indeed, the spring 4, by being arranged/ trapped between an inner surface of the body and the trigger button 3, and by virtue of the blade member 5 entering the slot 3d, maintains a compressed state shown in FIG. 11, while the biasing member 6 maintains an expanded state shown in FIG. 18. This ensures that the blade member 5 cannot be re-armed, and ensures that the blade member 5 (along with the tip portion 5a) is safely retained within the body after a one-time use.

FIGS. 75-86 show another embodiment of a lancet device. The device is similar to that of FIGS. 1-23 except that it utilizes a removable and/or adjustable movable blade depth adjusting arrangement. The rear and front covers 1 and 2 are replaced by rear and front covers 10000 and 20000 which are similar that the rear and front covers 1 and 2, except that front cover 20000 and a member BDS are separate parts. The remaining parts which similar to that of FIGS. 1-23 use corresponding reference numbers. The arrangement includes a movable blade depth setting member BDS which can move within a groove G (see FIG. 86) of the front cover 20000. The member BDS includes two projecting pins 2000f which correspond and function in the same way as the pins 2f of the embodiment shown in FIGS. 1-23. However, unlike the embodiment shown in FIGS. 1-23, in this embodiment the member BDS is not formed integrally with the front cover 20000, and is instead form as a separate member (see FIG. 80). As can be seen in FIGS. 77-79 and 81-84, the member BDS also includes an engaging projection EP which engages with a plurality of engaging notches EN. Depending on the position, the member BDS can be moved towards to the blade opening BO (see FIG. 78), to one or more intermediate positions (see FIG. 77) or to a position away from the blade opening BO (see FIG. 79). The desired position of the member BDS can preferably be set in a factory setting. Of course, the invention contemplates using the separate member BDS in any of the other embodiments disclosed in this application. The device otherwise functions in the same way as that described with regard to FIGS. 1-23.

FIGS. 87-90c show still another non-limiting embodiment of a single-use and/or disposable blade lancet device LD. Lancet device LD is similar to the embodiment shown in FIGS. 1-23 except that the trigger button is replaced with a different trigger button 300 (see FIGS. 90a-c) and no trigger coil spring 4 is utilized. Instead, the trigger button 300 includes a receiving notch 300b1 and dispenses with the oppositely arranged projections 3e. As with the embodiment shown in FIGS. 1-23, the trigger button 300 is seated in a trigger opening 2d formed in the front cover 2 and is sized to slide within the opening 2d in a smooth low-friction manner. The trigger button 300 has a finger engaging (e.g. push button) portion 300a (see FIGS. 90a-c) that can be pushed into the lancet body (see FIGS. 87-89). Unlike the embodiment shown in FIGS. 1-23, however, the trigger button 300 is not biased towards an extended position (see FIG. 87) via a coil compression spring. Instead, the blade member 5 is biased into a notch 300b1 by the spring 6. This biasing force can be overcome, of course, when the trigger button 300 is pushed into the lancet body (see FIGS. 88 and 89) by applying a force to the finger engaging portion 300a. However, because the trigger button 300 includes a slot 300d, once the blade member 5 enters the slot 300d (see FIG. 89), and engages the bottom surface 300g of the slot 300d under the biasing force of the leaf spring 6, the trigger button 300 is prevented from moving back by the blade member 5 to the position shown in FIG. 87. Thus, once triggered, the lancet device is automatically rendered unusable again—thereby rendering the device a single-use device.

FIGS. 90a-90c show rear, side and front views of the trigger button 300. The trigger button 300 can preferably be made as one-piece structure by e.g., injection molding. In this regard, it is preferably made of a plastic or synthetic resin such as, e.g., ABS plastic. The trigger button 300 may also be made of ABS-Red and have a finish designated as SPI-A2. Of course, other materials and/or finishes may be utilized, without leaving the scope of the invention. Additionally, by way of non-limiting example, the trigger button 300 may have an overall length that is approximately ½" (i.e., measured horizontally across FIG. 90b). Moreover, the trigger button 300 may even be made of a plurality of sections of parts which are joined together to form the complete trigger button 300, without leaving the scope of the invention, although it is preferred that it be formed a one-piece member. It would be even more preferable if the trigger button 300 were integrally formed with the lancet body, and in particular, integrally formed with the upper body part 2 and connected thereto with a living hinge (not shown).

The operation of the device shown in FIGS. 87-90c will now be explained with reference to FIGS. 87-89. FIG. 87 shows the lancet device LD with the blade member 5 in the loaded position, i.e., ready to move to an extended and second retracted position when the trigger button 300 is pressed. The blade member 5 retains the loaded position of FIG. 87 as a result of engagement between the bottom surface 5f of the blade member 5 with the notch 300b1 of the trigger button 300. On the other hand, FIG. 88 shows what initially happens when the trigger button 300 is pressed, i.e., the trigger button 300 is caused to move/slide inwardly against the biasing force of the spring 6, which becomes compressed by a slight upward movement of the blade member 5 which moves due to engagement with the angled/ramped surface of the notch 300b1. As soon as the trigger button 300 moves to a position wherein the slot 300d is positioned below the edge 5f of the blade member 5 (see FIG. 89), the biasing force of the spring 6 causes the blade member 5 to move downwards and into the slot 300d in a fraction of a second. However, because this movement is controlled by guiding engagement between the projections 2f and cam recesses 5d and 5e, the blade member 5 also simultaneously moves horizontally. The combined downward/horizontal movement has the shape of a curved path (see FIGS. 103-104). Thus, when the blade member 5 is released from the loaded position of FIG. 87, it is caused to move along the curved path dictated by the guiding system 2f, 5d and 5e. This occurs because the trigger button 300 allows the blade member 5 to enter the slot 300d. As discussed above, this movement is caused by the expansion (in the downward direction) of the spring 6. The blade member 5 thus moves towards and past the surface SCS and then back again until the projections 2f contact or engage the inner edges of the cam slots 5d and 5e and/or until the surface 5f of the blade member 5 engages with the surface 300g of the slot 300d. Once the trigger button 300 is released (once a user stops pressing on the trigger 300), the trigger button 300 is automatically prevented from moving back to the armed state shown in FIG. 87. Thus, unlike known prior art devices, the lancet device contains no mechanism for reloading and/or moving the blade member 5 and/or trigger button 300 back into the position shown in FIG. 87, i.e., the lancet device LD cannot then be placed back into the position shown in FIG. 87 because the device contains no mechanism for placing the surface 5f back into engagement with the notch 300b1. Indeed, the spring 6, by biasing the blade member 5 downwards and the trigger button 300, and by virtue of the blade member 5 entering the slot 300d, maintains an expanded state. As with the previous embodiments, the trigger button 300 is prevented from moving back to the expanded/triggering position shown in FIG. 87. This ensures that the blade member 5 cannot be re-armed, and ensures that the blade member 5 (along with the tip portion 5a) is safely retained within the body after a one-time use.

FIGS. 91-94 show another embodiment of a lancet device. The device is similar to that of FIGS. 75-86 except that the removable and/or adjustably movable blade depth adjusting arrangement can be adjusted by a user. The rear and front covers 1 and 2 are replaced by rear and front covers which are similar that the rear and front covers 1 and 2, except that front cover FC and a member BDS' are separate parts. The remaining parts which similar to that of FIGS. 1-23 use corresponding reference numbers. The arrangement includes a movable blade depth setting member BDS' which can move within a groove G (see FIG. 92) of the front cover FC. The member BDS' includes two projecting pins which correspond and function in the same way as the pins 2f of the embodiment shown in FIGS. 1-23. However, unlike the embodiment shown in FIGS. 1-23, in this embodiment the member BDS' is not formed integrally with the front cover FC, and is instead form as a separate member. As can be seen in FIGS. 93-96, the member BDS' also includes an engaging projection EP which connected by a living hinge LH. The engaging projection EP engages with a plurality of engaging notches EN. Depending on the desired setting position, which can be noted by the indicia ID, the member BDS' can be moved towards to the blade opening BO (see FIG. 91), to one or more intermediate positions or to a position away from the blade opening BO (see FIG. 92). The desired position of the member BDS' can preferably be set between these positions by the user. Although not shown, the handle portion HP of the member BDS' extends through an opening in the front cover. Of course, the invention contemplates using the separate member BDS' in any of the other embodiments disclosed in this application. Once adjusted to a desired depth setting determined by the user, the device otherwise functions in the same way as that described with regard to FIGS. 1-23.

FIGS. 105-107 show another embodiment of a lancet device with the rear cover portion removed. The device is generally similar to that of FIGS. 1-23 except that the blade member (which uses arc-shaped recesses) in the embodiment of FIGS. 1-23 is replaced with a blade member BM having non-continuously curved and/or interrupted cam recesses, i.e., cam recesses which straight center portions. The figure shows an inside view of the front cover portion 2 with the spring member 6, blade member BM and trigger button 3 positioned therein. This blade member BM causes the blade tip to move with shown in FIGS. 106 and 107 instead of the path shown on FIGS. 103 and 104. The blade member BD can be alternatively used on any of the embodiments shown in FIGS. 1-23, 46-50, 51-55, 56-60, 61-74, 75-86, 87-90c, and 91-96. The arrangement/position of the spring member 6, blade member BM and trigger button 3 is in a trigger-set/retracted position.

FIGS. 108-110 show another embodiment of a lancet device with the rear cover portion removed. The device is generally similar to that of FIGS. 1-23 except that the blade member (which uses arc-shaped recesses) in the embodiment of FIGS. 1-23 is replaced with a blade member BM having angled and straight cam recesses, i.e., cam recesses which have angled beginning and ending portions and a straight center portion. The figure shows an inside view of the front cover portion 2 with the spring member 6, blade member BM and trigger button 3 positioned therein. This blade member BM causes the blade tip to move with shown in FIGS. 109 and 110 instead of the path shown on FIGS. 103 and 104 or FIGS.

106 and 107. The blade member BD can be alternatively used on any of the embodiments shown in FIGS. 1-23, 46-50, 51-55, 56-60, 61-74, 75-86, 87-90c, and 91-96. The arrangement/position of the spring member 6, blade member BM and trigger button 3 is in a trigger-set/retracted position.

FIG. 111 shows another embodiment of a lancet device with the rear cover portion, the spring member, the blade member, and the trigger button removed. The lancet device embodiment is formed by replacing the front cover portion of the embodiment shown in FIG. 24 with the one shown in FIG. 111. Using front cover FC shown in FIG. 111, with the cam grooves shaped like the cam recesses of FIG. 105 on the device shown in FIGS. 24-45 would produce the blade path shown in FIGS. 106 and 107.

FIG. 112 shows still another embodiment of a lancet device with the rear cover portion, the spring member, the blade member, and the trigger button removed. The lancet device embodiment is formed by replacing the front cover portion of the embodiment shown in FIGS. 24-45 with the one shown in FIG. 112. The device is generally similar to that of FIG. 24 except that the front cover uses an adjustable blade setting device BDS" whose handle portion HP may includes indicia and extends through an opening in a rear wall of the front cover portion FC. The adjustable blade setting device BDS" is shown in an interrupted horizontal groove G and is positioned in an intermediate adjustment position which would cause the blade to penetrate a medium amount into the skin of a user. The adjustment is made by engagement between a deflecting projection DP (which is connected to a bottom wall of the front cover FC via a living hinge and/or integrally formed with the front cover FC) whose projection engages with a plurality of engaging notches EN arranged on the setting device BDS".

All the parts of the lancet device, with the exception of the springs (which can be made of spring steel) and with the exception of the lancet blade member/blade tip, may be made from plastic materials and can be formed using conventional injection molding techniques or other known manufacturing methods. However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A single-use blade lancet device, comprising:
    a body comprising a rear end and a front end that includes a blade tip opening;
    a trigger at least one of associated with the body and mounted to the body;
    a blade member movably mounted within the body and comprising a front end and a rear end;
    the blade member being movable at least between a first retracted position, an extended position, and a second retracted position;
    a biasing arrangement that biases the blade member from the first retracted position towards the extended position and then towards the second retracted position; and
    a guiding arrangement which guides the blade member while the blade member moves from the first retracted position towards the extended position and then towards the second retracted position,
    wherein, during movement of the blade member, the guiding arrangement ensures that blade member maintains an orientation which is substantially parallel to an axis extending from the blade tip opening to the rear end of the body, and
    wherein, during the movement of the blade member, the blade member at least one of:
        has a side edge whose distance from the axis changes;
        has a side edge whose distance from the axis increases between the first and second retracted positions; and
        has a first side edge that moves toward the axis and a second side edge that moves away from the axis.

2. The device of claim 1, wherein the biasing arrangement comprises a spring.

3. The device of claim 1, wherein the biasing arrangement comprises at least one compression spring.

4. The device of claim 1, wherein the biasing arrangement comprises a leaf spring.

5. The device of claim 1, wherein the biasing member comprises two spaced apart compression springs.

6. The device of claim 1, wherein the trigger is movably mounted to the body.

7. The device of claim 1, wherein the body comprises a first housing part connected to a second housing part.

8. The device of claim 1, wherein the blade member comprises a body portion made of one material and a blade tip portion made of a different material.

9. The device of claim 1, wherein the guiding arrangement comprises two projections coupled to the blade member and two generally C-shaped cam recesses arranged within the body.

10. The device of claim 1, wherein the guiding arrangement comprises two projections coupled to the body and two generally C-shaped cam recesses arranged on the blade member.

11. The device of claim 1, wherein the guiding arrangement comprises two projections and two generally C-shaped cam recesses formed in the blade member.

12. The device of claim 1, wherein the guiding arrangement comprises a plurality of projections extending from one side of the blade member and a plurality of generally C-shaped cam recesses.

13. The device of claim 1, wherein the guiding arrangement comprises a plurality of non-movable projections and a corresponding plurality of generally C-shaped cam recesses, each generally C-shaped cam recess receiving therein one of the non-movable projections.

14. The device of claim 1, further comprising a trigger spring biasing the trigger towards an extended position.

15. The device of claim 1, wherein the trigger comprises a slot which receives therein a portion of the blade member when the blade member is in the second retracted position.

16. The device of claim 1, wherein the trigger comprises a slot which receives therein a portion of the blade member when the trigger moves from an extended position to a triggered position.

17. The device of claim 16, wherein the trigger comprises a cam surface which engages with the blade member when the blade member is in the first retracted position.

18. The device of claim 1, further comprising an adjusting system that adjusts a depth of penetration.

19. The device of claim 18, wherein the adjusting system comprises an engaging projection and a plurality of engaging recesses which are each configured to receive the engaging projection.

20. The device of claim 1, further comprising a removable safety device configured to prevent movement of the blade member.

21. The device of claim 1, wherein the body comprises a generally rectangular shape.

22. The device of claim 1, wherein the blade member comprises generally rectangular-shaped metal plate with a pointed blade tip defined by a tapered sharpened edge and a straight blunt edge.

23. The device of claim 1, wherein the guiding arrangement guides a blade tip of the blade member along a curved path.

24. The device of claim 1, wherein the guiding arrangement guides a blade tip of the blade member along a partially circular path.

25. The device of claim 1, wherein the body comprises oppositely arranged projecting ribs which movably guide the blade member.

26. The device of claim 1, wherein the blade member comprises at least one straight edge which remains substantially parallel to the axis throughout movement of the blade member.

27. The device of claim 1, wherein the blade member comprises a width, a thickness and a length, wherein the width is less than the length, and wherein the width is greater than the thickness by a factor of at least five.

28. The device of claim 1, wherein the blade member comprises a width, a thickness and a length, wherein the width is less than the length, and wherein the width is greater than the thickness by a factor of at least ten.

29. The device of claim 1, wherein the guiding arrangement comprises two spaced apart circular projections extending from an inner surface of the body and two spaced apart C-shaped cam recesses formed in or on the blade member.

30. The device of claim 1, wherein the body comprises at least one side opening through which a portion of the trigger protrudes.

31. The device of claim 1, wherein the body comprises an ergonomic shape to facilitate gripping.

32. The device of claim 1, wherein the front end of the body comprises an outwardly curved skin engaging surface.

33. The device of claim 1, wherein the body comprises a two-piece plastic body.

34. The device of claim 1, wherein the body comprises internal projecting fins which guide the movement of the blade member within the body.

35. The device of claim 1, wherein the blade tip opening is a rectangular-shaped opening.

36. The device of claim 1, wherein the blade tip opening is a rectangular-shaped slot.

37. A method of puncturing a surface of skin using the device of claim 1, the method comprising:
disposing the front end of the device against a user's skin;
triggering the trigger to cause a blade tip of the blade member to penetrate the user's skin; and
preventing the user from moving the blade member to the extended position and to the first retracted position.

38. A method of puncturing a surface of skin using the device of claim 1, the method comprising:
adjusting a set depth of penetration;
disposing the front end of the device against a user's skin;
triggering the trigger to cause a blade tip of the blade member to penetrate the user's skin; and
preventing the user from moving the blade member to the extended position and to the first retracted position.

39. A method of puncturing a surface of skin using the device of claim 1, the method comprising:
adjusting a set depth of penetration;
disposing the front end of the device against a user's skin;
triggering the trigger to cause a blade tip of the blade member to penetrate the user's skin; and
ensuring that the trigger remains in a triggered position.

40. A method of puncturing a surface of skin using the device of claim 1, the method comprising:
disposing the front end of the device against a user's skin;
triggering the trigger to cause a blade tip of the blade member to penetrate the user's skin; and
preventing the user from moving the trigger to an original armed or extended position.

41. A method of using the device of claim 1, the method comprising:
removing a removable safety device from the body;
disposing the front end of the device against a user's skin; and
triggering the trigger to cause movement of the blade member.

42. A method of using the device of claim 1, the method comprising:
moving an adjusting mechanism to a desired set position;
removing a removable safety device from the body;
disposing the front end of the device against a user's skin; and
triggering the trigger to cause movement of the blade member.

43. A method of using the device of claim 1, the method comprising:
removing a removable safety device from engagement with the blade member;
disposing the front end of the device against a user's skin; and
triggering the trigger to cause movement of the blade member.

44. A method of using the device of claim 1, the method comprising:
moving an adjusting mechanism to a desired set position;
removing a removable safety device from engagement with the blade member;
disposing the front end of the device against a user's skin; and
triggering the trigger to cause movement of the blade member.

45. A single-use blade lancet device, comprising:
a body comprising a rear end, a front end that includes a blade tip opening, and a sidewall arranged between the front end and the rear end;
a trigger;
a blade member movably mounted within the body and comprising a front end and a rear end;
the blade member being movable at least between a first retracted position, an extended position, and a second retracted position;
a biasing arrangement arranged on a side of the blade member and biasing the blade member from the first retracted position towards the extended position and then towards the second retracted position; and
a guiding arrangement which guides the blade member while the blade member moves from the first retracted position towards the extended position and then towards the second retracted position, wherein, during movement of the blade member, the guiding arrangement ensures that blade member maintains an orientation which is substantially parallel to an axis extending from the blade tip opening to the rear end of the body, and wherein, during the movement of the blade member, the blade member at least one of:
- has a side edge whose distance from the sidewall of the body changes;
- has a side edge whose distance relative to the axis is different in each of the first and second retracted positions; and
- has a first side edge that moves toward the axis and a second side edge that moves away from the axis.

46. The device of claim 45, wherein the biasing arrangement comprises a spring.

47. The device of claim 45, wherein the biasing arrangement comprises at least one compression spring.

48. The device of claim 45, wherein the biasing arrangement comprises a leaf spring.

49. The device of claim 45, wherein the guiding arrangement comprises projections and generally C-shaped cam recesses.

50. A single-use blade lancet device, comprising:

a body comprising a blade tip opening;

a trigger;

a blade member movably mounted within the body and comprising a front end and a rear end;

the blade member being movable at least between a first retracted position, an extended position, and a second retracted position;

a biasing arrangement arranged on a side of the blade member and biasing the blade member from the first retracted position towards the extended position and then towards the second retracted position; and a guiding arrangement which guides the blade member while the blade member moves from the first retracted position towards the extended position and then towards the second retracted position, wherein, during movement of the blade member, the guiding arrangement ensures that blade member maintains an orientation which is substantially parallel to an axis extending through the blade tip opening, and wherein, a distance between a side of the blade member and the axis is different in each of the first retracted position, the extended position, and the second retracted position.

51. The device of claim 50, wherein the guiding arrangement comprises projections engaging with generally C-shaped cam recesses.

* * * * *